(12) United States Patent
Stein et al.

(10) Patent No.: US 8,722,923 B2
(45) Date of Patent: *May 13, 2014

(54) CONJUGATES FOR TREATING NEURODEGENERATIVE DISEASES AND DISORDERS

(75) Inventors: Gideon Stein, Rosh HaAyin (IL); Abraham Nudelman, Rechovot (IL); Ada Rephaeli, Herzlia (IL); Irit Gil-Ad, Herzlia (IL); Abraham Weizman, Tel-Aviv (IL)

(73) Assignees: Ramot at Tel-Aviv University Ltd., Tel-Aviv (IL); Bar-Ilan University, Ramat-Gan (IL)

( * ) Notice: Subject to any disclaimer, the term of this patent is extended or adjusted under 35 U.S.C. 154(b) by 48 days.

This patent is subject to a terminal disclaimer.

(21) Appl. No.: 13/531,673

(22) Filed: Jun. 25, 2012

(65) Prior Publication Data

US 2012/0277310 A1    Nov. 1, 2012

Related U.S. Application Data

(63) Continuation of application No. 12/867,055, filed as application No. PCT/IL2009/000158 on Feb. 11, 2009, now Pat. No. 8,207,369.

(60) Provisional application No. 61/064,017, filed on Feb. 11, 2008.

(51) Int. Cl.
*C07C 261/00* (2006.01)
*C07C 229/00* (2006.01)
*A01N 37/12* (2006.01)

(52) U.S. Cl.
USPC ............ 560/160; 562/567; 514/538; 514/567

(58) Field of Classification Search
None
See application file for complete search history.

(56) References Cited

U.S. PATENT DOCUMENTS

| 2,914,528 | A | 11/1959 | Craig |
| 2,944,053 | A | 7/1960 | Edgerton |
| 2,969,358 | A | 1/1961 | Cusic |
| 3,227,708 | A | 1/1966 | Yale et al. |
| 3,956,493 | A | 5/1976 | Yale |
| 3,966,930 | A | 6/1976 | Buus et al. |
| 3,978,216 | A | 8/1976 | Fuxe |
| 4,153,694 | A | 5/1979 | Buus et al. |
| 4,629,691 | A | 12/1986 | Collins et al. |

(Continued)

FOREIGN PATENT DOCUMENTS

| CA | 2461663 | 4/2003 |
| CN | 1596141 | 3/2005 |

(Continued)

OTHER PUBLICATIONS

International Preliminary Report on Patentability Dated Sep. 7, 2012 From the International Bureau of WIPO Re. Application No. PCT/IB2011/000915.

(Continued)

*Primary Examiner* — Karl J Puttlitz

(57) ABSTRACT

A conjugate comprising L-DOPA covalently linked to at least one γ-aminobutyric acid (GABA) moiety, an ester and/or an addition salt thereof are disclosed, as well as uses thereof for treating a neurodegenerative disease or disorder.

34 Claims, 14 Drawing Sheets
(12 of 14 Drawing Sheet(s) Filed in Color)

(56) References Cited

U.S. PATENT DOCUMENTS

| | | | |
|---|---|---|---|
| 4,818,936 A | 4/1989 | Kemlo | |
| 5,051,448 A | 9/1991 | Shashoua | |
| 5,104,858 A | 4/1992 | Hait et al. | |
| 5,145,684 A | 9/1992 | Liversidge et al. | |
| 5,420,105 A | 5/1995 | Gustavson et al. | |
| 5,525,727 A | 6/1996 | Bodor et al. | |
| 5,828,405 A | 10/1998 | Vanier et al. | |
| 5,966,673 A | 10/1999 | Shannon | |
| 5,983,238 A | 11/1999 | Becker et al. | |
| 5,994,392 A | 11/1999 | Shashoua et al. | |
| 6,020,954 A | 2/2000 | Aggarwal | |
| 6,121,325 A | 9/2000 | Chen et al. | |
| 6,197,764 B1 | 3/2001 | Bradley et al. | |
| 6,239,867 B1 | 5/2001 | Aggarwal | |
| 6,294,562 B1 | 9/2001 | Stilz et al. | |
| 6,304,853 B1 | 10/2001 | Malnekoff | |
| 6,381,510 B1 | 4/2002 | Amidhozour et al. | |
| 6,569,853 B1 | 5/2003 | Borisy et al. | |
| 7,544,681 B2 | 6/2009 | Nudelman et al. | |
| 7,598,239 B2 | 10/2009 | Nudelman et al. | |
| 7,619,006 B2 | 11/2009 | Nudelman et al. | |
| 7,939,525 B2 | 5/2011 | Nudelman et al. | |
| 8,168,628 B2 | 5/2012 | Nudelman et al. | |
| 2001/0024532 A1 | 9/2001 | Malnekoff | |
| 2002/0010208 A1 | 1/2002 | Shashoua et al. | |
| 2002/0021439 A1 | 2/2002 | Priestley et al. | |
| 2002/0052170 A1 | 5/2002 | Holloway | |
| 2003/0065586 A1 | 4/2003 | Shaftel et al. | |
| 2003/0115079 A1 | 6/2003 | Rapaport | |
| 2004/0068417 A1 | 4/2004 | Sevdermish | |
| 2004/0092504 A1 | 5/2004 | Benja-Athon | |
| 2004/0103447 A1 | 5/2004 | Nawa et al. | |
| 2004/0242570 A1 | 12/2004 | Nudelman et al. | |
| 2005/0149369 A1 | 7/2005 | Sevdermish | |
| 2006/0046967 A1 | 3/2006 | Satyam | |
| 2006/0058219 A1 | 3/2006 | Miller | |
| 2006/0142181 A1 | 6/2006 | Miller | |
| 2007/0099977 A1 | 5/2007 | Nudelman et al. | |
| 2007/0197514 A1 | 8/2007 | Nudelman et al. | |
| 2007/0219181 A1 | 9/2007 | Kimura et al. | |
| 2008/0108606 A1 | 5/2008 | Nudelman et al. | |
| 2009/0215809 A1 | 8/2009 | Yao et al. | |
| 2009/0298814 A1 | 12/2009 | Nudelman et al. | |
| 2009/0304584 A1* | 12/2009 | Nudelman et al. | 424/1.65 |
| 2010/0063034 A1 | 3/2010 | Nudelman et al. | |
| 2010/0120755 A1 | 5/2010 | Nudelman et al. | |
| 2010/0204469 A1 | 8/2010 | Nudelman et al. | |
| 2011/0312948 A1 | 12/2011 | Nudelman et al. | |
| 2012/0309748 A1 | 12/2012 | Nudelman et al. | |
| 2013/0059910 A1 | 3/2013 | Nudelman et al. | |
| 2013/0150352 A1 | 6/2013 | Nudelman et al. | |
| 2013/0184347 A1 | 7/2013 | Nudelman et al. | |

FOREIGN PATENT DOCUMENTS

| | | |
|---|---|---|
| CN | 1997400 | 7/2007 |
| CN | 101247837 | 8/2008 |
| EP | 0361485 | 4/1990 |
| EP | 1429844 | 6/2004 |
| EP | 2272537 | 1/2011 |
| ES | 8707175 | 10/1987 |
| GB | 829246 | 3/1960 |
| GB | 1460713 | 5/1978 |
| GB | 1514312 | 6/1978 |
| GB | 2159636 | 12/1985 |
| GB | 2188630 | 10/1987 |
| GB | 2358541 | 7/2001 |
| IL | 161083 | 9/2002 |
| IL | 199877 | 9/2002 |
| JP | 50-025574 | 3/1975 |
| JP | 53-050185 | 5/1978 |
| JP | 62-501991 | 8/1987 |
| JP | 62-240660 | 10/1987 |
| JP | 02-128564 | 5/1990 |
| JP | 02-188527 | 7/1990 |
| JP | 03-017076 | 2/1991 |
| JP | 06-072868 | 3/1994 |
| JP | 10-059948 | 3/1998 |
| JP | 11-506723 | 6/1999 |
| JP | 2000-020681 | 1/2000 |
| JP | 2001-501965 | 2/2001 |
| JP | 2001-201454 | 7/2001 |
| JP | 2001-519754 | 10/2001 |
| JP | 2003-515564 | 5/2003 |
| JP | 2005-503423 | 2/2005 |
| JP | 2005-097120 | 4/2005 |
| JP | 2005-517669 | 6/2005 |
| JP | 4521187 | 8/2010 |
| WO | WO 86/04991 | 8/1986 |
| WO | WO 93/12496 | 6/1993 |
| WO | WO 96/40687 | 12/1996 |
| WO | WO 97/02819 | 1/1997 |
| WO | WO 97/44063 | 11/1997 |
| WO | WO 98/17678 | 4/1998 |
| WO | WO 98/52898 | 11/1998 |
| WO | WO 99/26661 | 6/1999 |
| WO | WO 01/39779 | 6/2001 |
| WO | WO 01/91011 | 11/2001 |
| WO | WO 02/28881 | 4/2002 |
| WO | WO 02/43652 | 6/2002 |
| WO | WO 03/026563 | 4/2003 |
| WO | WO 03/055424 | 7/2003 |
| WO | WO 03/061656 | 7/2003 |
| WO | WO 03/062942 | 7/2003 |
| WO | WO 2005/032474 | 4/2005 |
| WO | WO 2005/092392 | 10/2005 |
| WO | WO 2006/027711 | 3/2006 |
| WO | WO 2006/058219 | 6/2006 |
| WO | WO 2006/131923 | 12/2006 |
| WO | WO 2007/050318 | 5/2007 |
| WO | WO 2007/139818 | 12/2007 |
| WO | WO 2008/010222 | 1/2008 |
| WO | WO 2008/010223 | 1/2008 |
| WO | WO 2009/101616 | 8/2009 |
| WO | WO 2011/104637 | 9/2011 |
| WO | WO 2012/038963 | 3/2012 |

OTHER PUBLICATIONS

Office Action Dated Aug. 15, 2012 From the Israel Patent Office Re. Application No. 202291 and Its Translation Into English.

Requisition by the Examiner Dated Aug. 31, 2012 From the Canadian Intellectual Property Office Re. Application No. 2,610,838.

Translation of Notice of Reason for Rejection Dated Nov. 9, 2012 From the Japanese Patent Office Re. Application No. 2011-20274.

Office Action Dated Aug. 9, 2012 From the Israel Patent Office Re. Application No. 196538 and Its Translation Into English.

Translation of Notice of Reason for Rejection Dated Aug. 7, 2012 From the Japanese Patent Office Re. Application No. 2010-008725.

Advisory Action Before the Filing of an Appeal Brief Dated Aug. 17, 2012 From the US Patent and Trademark Office Re. U.S. Appl. No. 11/921,578.

"New Edition of Pharmaceutics", People's Hygiene Publishing House, 14: 178, 1998. Abstract in Chinese Only!

Advisory Action Before the Filing of an Appeal Brief Dated Jan. 10, 2012 From the US Patent and Trademark Office Re. U.S. Appl. No. 12/656,048.

Advisory Action Before the Filing of an Appeal Brief Dated Oct. 25, 2011 From the US Patent and Trademark Office Re. U.S. Appl. No. 12/764,124.

Applicant-Initiated Interview Summary Dated Apr. 19, 2012 From the US Patent and Trademark Office Re. U.S. Appl. No. 12/656,048.

Communication Pursuant to Article 94(3) Dated Apr. 2, 2008 From the European Patent Office Re.: Application No. 06756205.8.

Communication Pursuant to Article 94(3) EPC Dated Apr. 11, 2011 From the European Patent Office Re. Application No. 09711260.1.

Communication Pursuant to Article 94(3) EPC Dated Dec. 16, 2010 From the European Patent Office Re. Application No. 02772790.8.

Communication Pursuant to Article 94(3) EPC Dated Nov. 24, 2010 From the European Patent Office Re. Application No. 07789958.1.

(56) References Cited

OTHER PUBLICATIONS

Communication Pursuant to Article 94(3) EPC Dated Jan. 26, 2012 From the European Patent Office Re. Application No. 10182948.9.
Communication Pursuant to Article 96(2) EPC Dated Nov. 24, 2006 From the European Patent Office Re.: Application No. 02772790.8.
Communication Pursuant to Rules 70(2) and 70a(2) EPC Dated Jan. 31, 2011 From the European Patent Office Re. Application No. 10182948.9.
Communication Relating to the Results of the Partial International Search Dated May 10, 2007 From the International Searching Authority Re.: Application No. PCT/IL2006/000666.
Communication Relating to the Results of the Partial International Search Dated Jun. 13, 2006 From the International Searching Authority Re.: Application No. PCT/IL2005/000341.
Communication Relating to the Results of the Partial International Search Dated Nov. 20, 2007 From the International Searching Authority Re.: Application No. PCT/IL2007/000902.
Communication Relating to the Results of the Partial International Search Dated Nov. 27, 2007 From the International Searching Authority Re.: Application No. PCT/IL2007/000903.
Communication Under Rule 112 EPC Dated Oct. 2, 2007 From the European Patent Office Re.: Application No. 05718914.4.
Communication Under Rule 71(3) EPC Dated May 7, 2012 From the European Patent Office Re.: Application No. 06756205.8.
Communication Under Rule 71(3) EPC Dated Feb. 20, 2012 From the European Patent Office Re. Application No. 09711260.1.
Communication Under Rule 71(3) EPC Dated Sep. 21, 2011 From the European Patent Office Re. Application No. 02772790.8.
Communication Under Rule 71(3) EPC Dated Nov. 28, 2011 From the European Patent Office Re. Application No. 07789958.1.
Communication Under Rule 71(3) EPC Dated Jul. 30, 2012 From the European Patent Office Re. Application No. 10182948.9.
Decision to Grant a European Patent Pursuant to Article 97(1) EPC Dated Aug. 2, 2012 From the European Patent Office Re. Application No. 07789958.1.
English Summary of Examination Report Dated Sep. 4, 2007 From the Instituto Mexicano de la Propriedad Industrial Re. Application No. PA/a/2004/002912.
European Search Report and the European Search Opinion Dated Dec. 30, 2010 From the European Patent Office Re. Application No. 10182948.9.
Examination Report Dated Dec. 5, 2011 From the Instituto Mexican de la Propriedad Industrial Re. Application No. MX/a/2009/000641 and Its Summary in English.
Examination Report Dated Jun. 8, 2011 From the Instituto Mexican de la Propriedad Industrial Re. Application No. MX/a/2007/015511 and Its Summary Into English.
Examination Report Dated Jun. 16, 2011 From the Instituto Mexicano de la Propriedad Industrial Re. Application No. PA/a/2006/010924 and Its Summary in English.
Examination Report Dated Jan. 19, 2012 From the Instituto Mexicano de la Propriedad Industrial Re. Application No. MX/a/2007/015511 and Its Translation Into English.
Examination Report Dated Sep. 20, 2010 From the Instituto Mexican der la Propriedad industrial Re. Application No. MX/a/2007/015511 and its Translation Into English.
Examination Report Dated Aug. 25, 2010 From the Instituto Mexican de la Propriedad Industrial Re. Application No. PA/a/2004/002912 and Its Summary in English.
Examination Report Dated May 30, 2011 From the Instituto Mcxicano dc la Propriedad Industrial Re. Application No. PA/a/2004/002912 and Its Summary in English.
Examiner's Report Dated May 23, 2007 From the Government of India Patent Office Re.: Application No. 642/CHENP/2004-SPS.
Examiner's Report Dated May 2, 2007 From the Australian Government, IP Australia Re.: Application No. 2004201240.
Examiner's Report Dated Jun. 7, 2012 From the Australian Government, IP Australia Re. Application No. 2006256369.
Examiner's Report Dated Oct. 7, 2011 From the Australian Government, IP Australia Re. Application No. 2007274583.
Examiner's Report Dated Jan. 19, 2012 From the Australian Government, IP Australia Re. Application No. 2006256369.
Examiner's Report Dated Oct. 21, 2010 From the Australian Government, TP Australia Re. Application No. 2006256369.
Examiner's Report Dated Feb. 24, 2010 From the Australian Government, IP Australia Re.: Application No. 2008243147.
International Preliminary Report on Patentability Dated Dec. 3, 2007 From the International Preliminary Examining Authority Re.: Application No. PCT/IL2006/000666.
International Preliminary Report on Patentability Dated Oct. 12, 2006 From the International Bureau of WIPO Re.: Application No. PCT/IL2005/000341.
International Preliminary Report on Patentability Dated Oct. 17, 2007 From the International Preliminary Examining Authority Re.: Application No. PCT/IL2006/000666.
International Preliminary Report on Patentability Dated Jun. 12, 2012 From the International Bureau of WIPO Re. Application No. PCT/IL2010/01041.
International Preliminary Report on Patentability Dated Aug. 26, 2010 From the International Bureau of WIPO Re. Re. Application No. PCT/IL2009/000158.
International Preliminary Report on Patentability Dated Jan. 29, 2009 From the International Bureau of WIPO Re.: Application No. PCT/IL2007/000902.
International Preliminary Report on Patentability Dated Jan. 29, 2009 From the International Bureau of WIPO Re.: Application No. PCT/IL2007/000903.
international Search Report and the Written Opinion Dated Dec. 1, 2011 From the International Searching Authority Re. Application No. PCT/IB2011/000915.
International Search Report and the Written Opinion Dated Dec. 3, 2007 From the International Searching Authority Re.: Application No. PCT/IL2006/000666.
International Search Report and the Written Opinion Dated Feb. 8, 2012 From the international Searching Authority Re.: Application No. PCT/IL2011/000752.
International Search Report and the Written Opinion Dated Feb. 12, 2008 From the International Searching Authority Re.: Application No. PCT/IL2007/000903.
International Search Report and the Written Opinion Dated Feb. 13, 2008 From the International Searching Authority Re.: Application No. PCT/IL2007/000902.
International Search Report and the Written Opinion Dated Aug. 23, 2006 From the International Searching Authority Re.: Application No. PCT/IL2005/000341.
International Search Report and the Written Opinion Dated Jun. 25, 2009 From the International Searching Authority Re. Application No. PCT/IL2009/000158.
International Search Report and the Written Opinion Dated Mar. 30, 2011 From the International Searching Authority Re. Application No. PCT/IL2010/01041.
International Search Report Dated Jul. 11, 2003 From the International Searching Authority Re.: Application No. PCT/IL02/00795.
Interview Summary Dated May 6, 2011 From the US Patent and Trademark Office Re. U.S. Appl. No. 12/656,048.
interview Summary Dated Jan. 27, 2011 From the US Patent and Trademark Office Re.: U.S. Appl. No. 12/585,021.
Invitation to Pay Additional Fees Dated Jun. 13, 2006 From the International Searching Authority Re.: Application No. PCT/IL2005/000341.
Invitation to Pay Additional Fees Dated Nov. 20, 2007 From the International Searching Authority Re.: Application No. PCT/IL2007/000902.
Invitation to Pay Additional Fees Dated Nov. 27, 2007 From the International Searching Authority Re.: Application No. PCT/IL2007/000903.
Notice of Allowance Dated Dec. 1, 2011 From the US Patent and Trademark Office Re. U.S. Appl. No. 12/764,124.
Notice of Allowance Dated Jul. 10, 2009 From the US Patent and Trademark Office Re.: U.S. Appl. No. 11/636,599.
Notice of Allowance Dated Mar. 11, 2008 From the US Patent and Trademark Office Re.: U.S. Appl. No. 10/808,541.

(56) References Cited

OTHER PUBLICATIONS

Notice of Allowance Dated Apr. 12, 2012 From the US Patent and Trademark Office Re. U.S. Appl. No. 12/373,542.
Notice of Allowance Dated May 17, 2012 From the US Patent and Trademark Office Re. U.S. Appl. No. 12/656,048.
Notice of Allowance Dated Mar. 21, 2011 From the US Patent and Trademark Office Re.: U.S. Appl. No. 12/585,021.
Notice of Allowance Dated Feb. 23, 2012 From the US Patent and Trademark Office Re. U.S. Appl. No. 12/867,055.
Notice of Allowance Dated May 29, 2009 From the US Patent and Trademark Office Re.: U.S. Appl. No. 12/005,342.
Notice of Allowance Dated May 30, 2012 From the US Patent and Trademark Office Re. U.S. Appl. No. 12/309,361.
Notice of the Reason for Rejection Dated Mar. 26, 2010 From the Korean Intellectual Property Office Re.: Application No. 2004-7004581. Korean Only.
Office Action Dated Mar. 2, 2011 From the Israel Patent Office Re. Application No. 196538 and its Translation Into English.
Office Action Dated Mar. 2, 2011 From the Israeli Patent Office Re. Application No. 196538.
Office Action Dated Jun. 6, 2010 From the Israeli Patent Office Re.: Application No. 161083 and Its Translation Into English.
Office Action Dated Aug. 8, 2008 From the Patent Office of the People's Republic of China Re.: Application No. 02823600.9.
Office Action Dated Sep. 9, 2005 From the Patent Office of the People's Republic of China Re.: Application No. 02823600.9 and Its Translation Into English.
Office Action Dated Dec. 12, 2011 From the Israel Patent Office Re.: Application No. 187892 and Its Translation Into English.
Office Action Dated Feb. 14, 2008 From the Government of India Patent Office Re.: Application No. 642/CHENP/2004-SPS.
Office Action Dated Feb. 15, 2009 From the Israeli Patent Office Re.: Application No. 161083 and Its Translation Into English.
Office Action Dated May 15, 2008 From the Government of India Patent Office Re.: Application No. 642/CHENP/2004-SPS.
Office Action Dated May 17, 2011 From the Israel Patent Office Re.: Application No. 187892 and Its Translation Into English.
Office Action Dated Aug. 23, 2010 From the Israel Patent Office Re. Application No. 203058 and Its Translation Into English.
Office Action Dated Jun. 24, 2011 From the State Intellectual Property Office of the People's Republic of China Re. Application No. 200780033294.6 and Its Translation Into English.
Office Action Dated Apr. 25, 2010 From the Israel Patent Office Re.: Application No. 187892 and Its Translation Into English.
Office Action Dated Feb. 27, 2009 From the Israeli Patent Office Re.: Application No. 161083 and Its Translation Into English.
Office Action Dated Jul. 27, 2010 From the Israel Patent Office Re.: Application No. 199877 and Its Translation Into English.
Official Action Dated Feb. 1, 2007 From the US Patent and Trademark Office Re.: U.S. Appl. No. 10/808,541.
Official Action Dated Nov. 1, 2011 From the US Patent and Trademark Office Re. U.S. Appl. No. 11/921,578.
Official Action Dated Feb. 2, 2012 From the US Patent and Trademark Office Re. U.S. Appl. No. 12/656,048.
Official Action Dated May 3, 2012 From the US Patent and Trademark Office Re. U.S. Appl. No. 11/921,578.
Official Action Dated Aug. 5, 2011 From the US Patent and Trademark Office Re. U.S. Appl. No. 12/764,124.
Official Action Dated Jan. 6, 2011 From the US Patent and Trademark Office Re. U.S. Appl. No. 12/656,048.
Official Action Dated May 9, 2008 From the US Patent and Trademark Office Re.: U.S. Appl. No. 11/636,599.
Official Action Dated Jul. 12, 2011 From the US Patent and Trademark Office Re. U.S. Appl. No. 11/921,578.
Official Action Dated Dec. 14, 2010 From the US Patent and Trademark Office Re.: U.S. Appl. No. 12/585,021.
Official Action Dated Mar. 14, 2011 From the US Patent and Trademark Office Re. U.S. Appl. No. 12/764,124.
Official Action Dated Feb. 16, 2010 From the US Patent and Trademark Office Re.: U.S. Appl. No. 12/585,021.
Official Action Dated May 16, 2008 From the US Patent and Trademark Office Re.: U.S. Appl. No. 11/636,594.
Official Action Dated Sep. 16, 2008 From the US Patent and Trademark Office Re.: U.S. Appl. No. 12/005,342.
Official Action Dated Apr. 17, 2008 From the US Patent and Trademark Office Re.: U.S. Appl. No. 11/636,594.
Official Action Dated Feb. 17, 2009 From the US Patent and Trademark Office Re.: U.S. Appl. No. 11/636,599.
Official Action Dated Jun. 17, 2010 From the US Patent and Trademark Office Re.: U.S. Appl. No. 12/585,021.
Official Action Dated May 17, 2012 From the US Patent and Trademark Office Re. U.S. Appl. No. 13/034,453.
Official Action Dated Jun. 19, 2008 From the US Patent and Trademark Office Re.: U.S. Appl. No. 11/636,599.
Official Action Dated Oct. 21, 2011 From the US Patent and Trademark Office Re. U.S. Appl. No. 12/373,542.
Official Action Dated Nov. 22, 2011 From the US Patent and Trademark Office Re. U.S. Appl. No. 12/309,361.
Official Action Dated Jun. 23, 2011 From the US Patent and Trademark Office Re. U.S. Appl. No. 12/373,542.
Official Action Dated Aug. 25, 2010 From the US Patent and Trademark Office Re. U.S. Appl. No. 12/764,124.
Official Action Dated Aug. 25, 2011 From the US Patent and Trademark Office Re. U.S. Appl. No. 12/656,048.
Official Action Dated Jul. 25, 2006 From the US Patent and Trademark Office Re.: U.S. Appl. No. 10/808,541.
Official Action Dated Mar. 30, 2006 From the US Patent and Trademark Office Re.: U.S. Appl. No. 10/808,541.
Official Action Dated Jan. 31, 2012 From the US Patent and Trademark Office Re. U.S. Appl. No. 12/309,361.
Official Action Dated Jan. 31, 2012 From the US Patent and Trademark Office Re. U.S. Appl. No. 13/034,453.
Official Action Dated Oct. 31, 2008 From the US Patent and Trademark Office Re.: U.S. Appl. No. 12/005,342.
Patent Examination Report Dated Jul. 31, 2012 From the Australian Government, IP Australia Re. Application No. 2007274583.
Requisition by the Examiner Dated Aug. 2, 2011 From the Canadian Intellectual Property Office Re. Application No. 2,461,663.
Requisition by the Examiner Dated Aug. 2, 2011 From the Canadian Intellectual Property Office Re. Application No. 2,560,905.
Requisition by the Examiner Dated Nov. 8, 2010 From the Canadian Intellectual Property Office Re. Application No. 2,461,663.
Requisition by the Examiner Dated Apr. 13, 2012 From the Canadian Intellectual Property Office Re. Application No. 2,461,663.
Requisition by the Examiner Dated May 16, 2012 From the Canadian Intellectual Property Office Re. Application No. 2,560,905.
Response Dated May 1, 2006 to Official Action of Mar. 30, 2006 From the US Patent and Trademark Office Re.: U.S. Appl. No. 10/808,541.
Response Dated Sep. 1, 2010 to Office Action of Apr. 25, 2010 From the Israel Patent Office Re.: Application No. 187892.
Response Dated Aug. 2, 2011 to Office Action of Mar. 2, 2011 From the Israeli Patent Office Re. Application No. 196538.
Response Dated Dec. 3, 2007 to Official Action of Feb. 1, 2007 From the US Patent and Trademark Office Re.: U.S. Appl. No. 10/808,541.
Response Dated Mar. 3, 2010 to Official Action of Feb. 16, 2010 From the US Patent and Trademark Office Re.: U.S. Appl. No. 12/585,021.
Response Dated Oct. 3, 2011 to Examination Report of Jun. 8, 2011 From the Instituto Mexican de la Propriedad Industrial Re. Application No. MX/a/2007/015511.
Response Dated Oct. 3, 2011 to Office Action of Jun. 6, 2010 From the Israeli Patent Office Re.: Application No. 161083.
Response Dated May 5, 2011 to Requisition by the Examiner of Nov. 8, 2010 From the Canadian Intellectual Property Office Re. Application No. 2,461,663.
Response Dated Oct. 5, 2010 to Official Action of Jun. 17, 2010 From the US Patent and Trademark Office Re.: U.S. Appl. No. 12/585,021.
Response Dated Jul. 6, 2011 to Official Action of Mar. 14, 2011 From the US Patent and Trademark Office Re. U.S. Appl. No. 12/764,124.
Response Dated Jun. 6, 2010 to Office Action of Jan. 29, 2010 From the State Intellectual Property Office of the People's Republic of China Re.: Application No. 200680029378.8.

(56) References Cited

OTHER PUBLICATIONS

Response Dated Jun. 6, 2011 to Official Action of Jan. 6, 2011 From the US Patent and Trademark Office Re. U.S. Appl. No. 12/656,048.
Response Dated Sep. 7, 2011 to Official Action of Jul. 12, 2011 From the US Patent and Trademark Office Re. U.S. Appl. No. 11/921,578.
Response Dated Nov. 8, 2010 to Office Action of Jul. 12, 2010 From the State Intellectual Property Office of the People's Republic of China Re. Application No. 200780033294.6.
Response Dated Feb. 9, 2011 to Office Action of Aug. 11, 2010 From the State Intellectual Property Office of the People's Republic of China Re. Application No. 200810190781.X.
Response Dated Mar. 9, 2011 to Official Action of Dec. 14, 2010 From the US Patent and Trademark Office Re.: U.S. Appl. No. 12/585,021.
Response Dated Jan. 13, 2010 to Notice for Reason for Rejection of Oct. 20, 2009 From the Japanese Patent Office Re.: Application No. 2003-530202.
Response Dated Jan. 13, 2010 to Office Action of Jul. 17, 2009 From the State Intellectual Property Office of the People's Republic of China Re.: Application No. 200580017025.1.
Response Dated Oct. 13, 2008 to Official Action of Sep. 16, 2008 From the US Patent and Trademark Office Re.: U.S. Appl. No. 12/005,342.
Response Dated Dec. 14, 2011 to Notice of Reason for Rejection of Sep. 30, 2011 From the Japanese Patent Office Re. Application No. 2007504560.
Response Dated Dec. 15, 2011 to Examiner's Report of Oct. 21, 2010 From the Australian Government, IP Australia Re. Application No. 2006256369.
Response Dated Nov. 15, 2006 to Official Action of Jul. 25, 2006 From the US Patent and Trademark Office Re.: U.S. Appl. No. 10/808,541.
Response Dated Jun. 16, 2011 to Communication Pursuant to Article 94(3) EPC of Dec. 16, 2010 From the European Patent Office Re. Application No. 02772790.8.
Response Dated Nov. 16, 2010 to Examination Report of Aug. 25, 2010 From the Instituto Mexicano de la Propriedad Industrial Re. Application No. PA/a/2004/002912.
Response Dated Feb. 18, 2011 to Examination Report Dated Sep. 20, 2010 From the Instituto Mexicano der la Propriedad Industrial Re. Application No. MX/a/2007/015511 and Its Translation Into English.
Response Dated Jan. 18, 2011 to Notice of Reason for Rejection of Nov. 2, 2010 From the Japanese Patent Office Re. Application No. 2007504560.
Response Dated Sep. 18, 2011 to Examination Report of Jun. 16, 2011 From the Instituto Mexicano de la Propriedad Industrial Re. Application No. PA/a/2006/010924.
Response Dated Oct. 19, 2011 to Official Action Dated Aug. 5, 2011 From the US Patent and Trademark Office Re. U.S. Appl. No. 12/764,124.
Response Dated Dec. 20, 2010 to Notice of the Reason for Rejection of Oct. 28, 2010 From the Korean Itellectual property Office Re. Application No. 2010-7016372.
Response Dated Jul. 20, 2011 to Notice of Final Rejection of May 30, 2011 From the Korean Intellectual Property Office Re. Application No. 2010-7016372.
Response Dated Aug. 22, 2011 to Office Action of Jun. 24, 2011 From the State Intellectual Property Office of the People's Republic of China Re. Application No. 200780033294.6.
Response Dated Mar. 22, 2011 to Final Notice of the Reason for Rejection of Nov. 24, 2010 From the Korean Intellectual Property Office Re.: Application No. 2009-7024590.
Response Dated Aug. 23, 2011 to Official Action of Jun. 23, 2011 From the US Patent and Trademark Office Re. U.S. Appl. No. 12/373,542.
Response Dated Dec. 23, 2010 to Office Action of Aug. 23, 2010 From the Israel Patent Office Re. Application No. 203058.
Response Dated Feb. 23, 2011 to Examiner's Report of Feb. 24, 2010 From the Australian Government, IP Australia Re.: Application No. 2008243147.
Response Dated Jun. 23, 2010 to Notice of the Reason for Rejection of Feb. 24, 2010 From the Korean Intellectual Property Office Re.: Application No. 2009-7024590.
Response Dated Jun. 23, 2010 to Notice of the Reason for Rejection of Mar. 26, 2010 From the Korean Intellectual Property Office Re.: Application No. 20047004581.
Response Dated Nov. 23, 2009 to Office Action of Jul. 23, 2009 From the Israel Patent Office Re.: Application No. 199877.
Response Dated Oct. 23, 2011 to Office Action Dated May 17, 2011 From the Israel Patent Office Re.: Application No. 187892.
Response Dated Feb. 24, 2009 to Official Action of Oct. 31, 2008 From the US Patent and Trademark Office Re.: U.S. Appl. No. 12/005,342.
Response Dated Jul. 24, 2011 to Communication Pursuant to Article 94(3) EPC of Apr. 11, 2011 From the European Patent Office Re. Application No. 09711260.1.
Response Dated Mar. 24, 2011 to Communication Pursuant to Article 94(3) EPC of Nov. 24, 2010 From the European Patent Office Re. Application No. 07789958.1.
Response Dated Nov. 24, 2011 to Official Action of Aug. 25, 2011 From the US Patent and Trademark Office Re. U.S. Appl. No. 12/656,048.
Response Dated Feb. 25, 2011 to Official Action of Aug. 25, 2010 From the US Patent and Trademark Office Re. U.S. Appl. No. 12/764,124.
Response Dated Jul. 26, 2011 to Official Action of Mar. 14, 2011 From the US Patent and Trademark Office Re. U.S. Appl. No. 12/764,124.
Response Dated Jul. 26, 2011 to Communication Pursuant to Rules 70(2) and 70a(2) EPC of Jan. 31, 2011 From the European Patent Office Re. Application No. 10182948.9.
Response Dated Nov. 28, 2010 to Office Action of Jul. 27, 2010 From the Israel Patent Office Re.: Application No. 199877.
Response Dated Dec. 30, 2009 to Office Action of Aug. 31, 2009 From the Israel Patent Office Re.: Application No. 161083.
Restriction Official Action Dated Dec. 20, 2011 From the US Patent and Trademark Office Re. U.S. Appl. No. 13/034,453.
Summons to Attend Oral Proceedings Pursuant to Rule 115(1) EPC Dated Jan. 26, 2012 From the European Patent Office Re. Application No. 06756205.8.
Supplemental After Final Amendment Dated Nov. 17, 2011 in Response to Official Action Dated Aug. 5, 2011 From the US Patent and Trademark Office Re. U.S. Appl. No. 12/764,124.
Supplemental Response Dated Mar. 31, 2009 to Response of Feb. 24, 2009 From the US Patent and Trademark Office Re.: U.S. Appl. No. 12/005,342.
Supplementary European Search Report Dated Apr. 25, 2006 From the European Patent Office Re.: Application No. 02772790.8.
Translation of Decision on Rejection Dated May 30, 2012 From the State Intellectual Property Office of the People's Republic of China Re.: Application No. 200580017025.1.
Translation of Final Notice of the Reason for Rejection Dated Nov. 24, 2010 From the Korean Intellectual Property Office Re.: Application No. 2009-7024590.
Translation of Final Notice of the Reason for Rejection Dated Aug. 31, 2011 From the Korean Intellectual Property Office Re. Application No. 2010-7016372.
Translation of Notice for Reason for Rejection Dated Oct. 20, 2009 From the Japanese Patent Office Re.: Application No. 2003-530202.
Translation of Notice of Final Rejection Dated May 30, 2011 From the Korean Intellectual Property Office Re. Application No. 2010-7016372.
Translation of Notice of Final Rejection Dated May 30, 2011 From the Korean Intellectual Property Office Re.: Application No. 2009-7024590.
Translation of Notice of Reason for Rejection Dated Nov. 2, 2010 From the Japanese Patent Office Re. Application No. 2007-504560.
Translation of Notice of Reason for Rejection Dated Feb. 10, 2009 From the Japanese Patent Office Re.: Application No. 2003-530202.
Translation of Notice of Reason for Rejection Dated Jul. 20, 2012 From the Japanese Patent Office Re. Application No. 2009-520129.
Translation of Notice of Reason for Rejection Dated Nov. 29, 2011 From the Japanese Patent Office Re. Application No. 2008-515378.

(56) References Cited

OTHER PUBLICATIONS

Translation of Notice of Reason for Rejection Dated Sep. 30, 2011 From the Japanese Patent Office Re. Application No. 2007-504560.
Translation of Notice of the Reason for Rejection Dated Jun. 1, 2012 From the Korean Patent Office Re. Application No. 2012-7002565.
Translation of Notice of the Reason for Rejection Dated Feb. 24, 2010 From the Korean Intellectual Property Office Re.: Application No. 2009-7024590.
Translation of Notice of the Reason for Rejection Dated Aug. 26, 2009 From the Korean Intellectual Property Office Re.: Application No. 2004-7004581.
Translation of Notice of the Reason for Rejection Dated Mar. 26, 2010 From the Korean Intellectual Property Office Re.: Application No. 2004-7004581.
Translation of Notice of the Reason for Rejection Dated Oct. 28, 2010 From the Korean Intellectual Property Office Re. Application No. 2010-7016372.
Translation of Office Action Dated Nov. 3, 2011 From the State Intellectual Property Office of the People's Republic of China Re.: Application No. 200580017025.1.
Translation of Office Action Dated Jan. 5, 2012 From the State Intellectual Property Office of the People's Republic of China Re. Application No. 200810190781.X.
Translation of Office Action Dated Aug. 11, 2010 From the State Intellectual Property Office of the People's Republic of China Re. Application No. 200810190781.X.
Translation of Office Action Dated Jul. 12, 2010 From the State Intellectual Property Office of the People's Republic of China Re. Application No. 200780033294.6.
Translation of Office Action Dated Jul. 17, 2009 From the State Intellectual Property Office of the People's Republic of China Re.: Application No. 200580017025.1.
Translation of Office Action Dated Feb. 23, 2012 From the State Intellectual Property Office of the People's Republic of China Re. Application No. 200780033294.6.
Translation of Office Action Dated Jan. 29, 2010 From the State Intellectual Property Office of the People's Republic of China Re.: Application No. 200680029378.8.
Translation of Office Action Dated Jan. 30, 2012 From the State Intellectual Property Office of the People's Republic of China Re.: Application No. 200680029378.8.
Translation of Official Decision of Rejection Dated Jul. 6, 2012 From the Japanese Patent Office Re. Application No. 2008-515378.
Written Opinion Dated Feb. 13, 2008 From the International Searching Authority Re.: Application No. PCT/IL2007/000902.
Written Opinion Dated Aug. 23, 2006 From the International Searching Authority Re.: Application No. PCT/IL2005/000341.
Written Opinion Dated Jun. 25, 2009 From the International Searching Authority Re. Application No. PCT/IL2009/000158.
Bastin et al. "Salt Selection and Optimisation Procedures for Pharmaceutical New Chemical Entities", Organic Process Research & Development, 4: 427-435, 2000.
BioLincRx "BioLincRx Announces Positive Topline Results for BL-1020, A First in Class GABA Enhanced Antipsychotic for the Treatment of Schizophrenia. BL-1020 Meets Primary and Secondary Efficacy Endpoints From the Pahase 2b EAGLE Trial", BioLine Rx, 4 P., Sep. 14, 2009.
Bousquet et al. "Synthesis, Physical Properties, Toxicological Studies and Bioavailability of L-Pyroglutamic and L-Glutamic Acid Esters of Paracetamol as Potentially Prodrugs", Journal of Pharmacy and Pharmacology, 48: 479-485, Jan. 1996.
Bryson et al. "Amitriptyline. A Review of Its Pharmacological Properties and Therapeutic Use in Chronic Pain States", Drug & Aging, 8(6): 459-476, 1996.
Budavari et al. "The Merck Index", Merck & Co., USA, XP002381834, 12th Ed., 1996. P.THER-8, First Col., 6th Line From the Bottom, 2nd Col., Line 13.
Budavari et al. "The Merck Index", Merck & Co., USA, XP002381799, 12th Ed, 1996, p. 1260, § 1.
Budavari et al. "The Merck Index", Merck & Co., USA, XP002381798, 12th Ed., 1996, p. 1246, Last §.
Capasso et al. "Anticonvulsive Activity of a New GABA Mimetic Drug", European Neuropsychopharmacology, 7: 57-63, 1997.
Carducci et al. "Phenylbutyrate Induces Apoptosis in Human Prostate Cancer and Is More Potent Than Phenylacetate", Clinical Cancer Research, XP002613699, 2(2): 379-387, 1996. Abstract.
Chan et al. "Phenothiazine Inhibitors of Trypanothione Reductase as Potential Antitrypanosomal and Antileishmanial Drugs", Journal of Medicinal Chemistry, 41(2): 148-156, 1998.
Coradini et al. "Effect of Sodium Butyrate on Human Breast Cancer Cell Lines", Cell Proliferation, XP002613698, 30(3-4) Mar. 1997. Abstract.
Degrand et al. "Synthesis of Nitroxides for Use as Procationic Labels and Their Incorporation Into Nafion Films", The Journal of Organic Chemistry, 58(9): 2573-2577, 1993.
Dutta et al. "Existing Dopaminergic Therapies for Parkinson's Disease", Expert Opinion on Therapeutic Patents, XP002531574, 16: 1613-1625, 2006. § [04.1], Fig.1.
Fingl et al. "General Principles", The Pharmacological Basis of Therapeutics, Chap.1: 1-46, 1975.
Florence et al. "Prolongation of the Action of Intramuscular Formulations of Phenothiazines", Optimization of Drug Delivery, 17th Alfred Benzon Symposium, Mungsgaard, Copenhagen, p. 93-111, 1982.
Geyer et al. "Animal Behavior Models of the Mechanisms Underlying Antipsychotic Atypicality", Progress in Neuro-Psychopharmacology & Biological Psychiatry, 27: 1071-1079, 2003.
Gil-Ad et al. "Novel Anti-Psychotics That Display GABAergic Acitivity and Decreased Extrapyramidal Side Effects, for the Treatment of Schizophrenia and Related Psychiatric Disorders", Neural Plasticity, XP008064103, 10(3): 200, 2003. Abstract.
Hadad et al. "Pharmacokinetic Analysis and Antiepileptic Activity of N-Valproyl Derivatives of GABA and Glycine", Pharmaceutical Research, XP008038069, 112(6): 905-910, Jan. 1, 1995. Abstract, p. 906, Compound IV, p. 909, r-h Col., § 1.
Koepf-Maier et al. "An Organoid Culture Assay (OCA) for Determining the Drug Sensitivity of Human Tumors", International Journal of Cancer, 51: 99-107, 1992.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
Luo "Pharmacokinetic Studies of Fluphenazine and Four Ester Prodrugs", A Thesis Submitted to the College of Graduate Studies and Research in Partial Fulfillment of the Requirements for the Degree of Doctor of Philosophy in the College of Pharmacy and Nutrition, University Saskatchewan, Saskatoon, Saskatchewan, Canada, p. 1-171, Mar. 1999. p. 5, § 1.2.1.1, p. 19, Compounds, p. 39, § 3.2.2.0, p. 147-152.
Luo et al. "Comparative Pharmacokinetic Analysis of Fluphenazine and Four Ester Prodrugs", Pharmaceutical Research, XP008130430, 14(11 Suppl.): S360, # 2441, Nov. 1997. & Annual Meeting of the American Association of Pharmaceutical Scientists, Boston, MA, USA, Nov. 2-6, 1997.
McCaffrey et al. "A Rapid Fluorometric DNA Assay for the Measurement of Cell Density and Proliferation in Vitro", In Vitro Cellular Development Biology, 24(3): 247-252, 1988. Abstract.
Merck "Schizophrenia", The Merck Manuals, Section Psychiatric Disorders, 17th Ed.: 1569-1575, Dec. 10, 1999. Japanese Version and Its Translation Into English. p. 1572, Right Col., Line 15-p. 1573, Left Col., Line 11, p. 1574, Table 193-1.
Milovic et al. "Effect of Structural Analogues of Propionate and Butyrate on Colon Cancer Cell Growth", International Journal of Colorectal Disease, XP002613700, 15(5-6): 264-270, 2000. Abstract, p. 267, Table 2.
Morissette et al. "High-Througput Crystallization: Polymorphs, Salts, Co-Crystals and Solvates of Pharmaceutical Solids", Advanced Drug Delivery Reviews, 56: 275-300, 2004.
Napolitano et al. "New Directions in Parkinson's Research and Treatment", Expert Opinion on Therapeutic Patents, XP002531575, 8: 1251-1268, 1998. Fig.4.

(56) References Cited

OTHER PUBLICATIONS

Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, XP001027786, 58(8): 1229-1236, Oct. 15, 1999. Abstract, p. 1231, r-h Col., § 2-p. 1232, l-h Col., § 2.
Ogiso et al. "Pharmacokinetic Analysis of Phenytoin and Its Derivatives in Plasma and Brain in Rats", Biological and Pharmaceutical Bulletin, XP002613683, 16(10): 1025-1030, Oct. 1, 1993. Fig.1, Compound 3, p. 1025, 1-h Col., § 1, r-h Col., § 1.
Pouzet et al. "Effects of the 5-HT7 Receptor Antagonist SB-258741 in Animal Models for Schizophrenia", Pharmacology, Biochemistry and Behavior, 71: 655-665, 2002.
Quadri et al. "Effects of Centrally Acting Drugs on Serum Prolactin Levels in Rhesus Monkeys", Neuroendocrinology, 27(3-4): 136-147, 1978. Abstract.
Rephaeli et al. "Gamm-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.
Rephaeli et al. "Observation of Sequence-Dependent Interaction Between Prodrugs of Carboxylic-Acid-Esters and Doxorubic in in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.
Sakamoto et al. "Studies on Prodrugs. VI. Preparation and Characterization of 95-Substituted 2-Oxo-1,3-Dioxol-4-yl)Methyl Esters of Mecillinam", Chemical and Pharmaceutical Bulletin, XP008078018, 35(2): 642-646, 1987. Abstract.
Scriba "Phenytoin-Lipid Conjugates as Potential Prodrugs of Phenytoin", Archiv der Pharmazie, VCH—Verlagsgesellschaft MBH, Weinheim, DE, XP001023947, 326(8): 477-481, 1993. Scheme 1, p. 147.
Scriba et al. "Anticonvulsant Activity of Phenytoin-Lipid Conjugates, A New Class of Phenytoin Prodrugs", Journal of Pharmaceutical Pharmacology, XP008064305, 47: 197-203, 1996. Scheme 1, p. 198, Abstract.
Scriba el al. "Synthesis and Anticovulsant. Activity of N-Benzyloxycarbonyl-Amino Acid Prodrugs of Phenytoin", Journal of Pharmacy and Pharmacology, XP008069882, 51(5): 549-553, May 1, 1999. Abstract, Fig.1.
Shalitin et al. "The Effect of Angiotensin II on Myosin Heavy Chain Expression in Cultured Myocardial Cells", In Vitro Cellular Development Biology—Animal, 32: 573-578, 1996.
Stahl et al. [Ed.] "A Procedure for Salt Selection and Optimization", (by Michael Bowker), Handbook of Pharmaceutical Salts, Chap.7: 161-189, 2002.
Toth "A Novel Chemical Approach to Drug Delivery: Lipidic Amino Acid Conjugates", Journal of Drug Targeting, XP00900873, 2(3): 217-239, 1994. p. 223, col. II, 3rd §.
Velazquez et al. "Butyrate Inhibits Seeding and Growth of Colorectal Metastases to the Liver in Mice", Surgery, XP005473855, 120(2): 440-448, Aug. 1, 1996. Abstract.
Vezin et al. "Biological Active Poly(N-Metacryloyl-?-Amino Acid) Esters of Fluphenazine and Their Duration of Activity", Journal of Pharmacy and Pharmacology, British Pharmacology Conference 1979, 31(Suppl.): 63P, 1979.
Ware et al. "An Automated Approach to Salt Selection for New Unique Trazodone Salts", Pharmaceutical Research, XP007902093, 21(1): 177-184, 2004. Abstract.
Wilson et al. "Central Nervous System Depressant", Wilson and Gisvold's Textbook of Organic Medicinal and Pharmaceutical Chemistry, 8th Ed., p. 362-371, 1982.
Wolffe "Transcriptional Control. Sinful Repression", Nature, 387: 16017, 1997.
Worms et al. "Dopamine-Like Activities of an Aminopyridazinde Derivative, CM 30366: A Behavioural Study", Naunyn-Schmiedeberg's Archives of Pharmacology, 334: 246-252, 1986.
Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, XP002392213, 17: 2325-2327, 2003. Abstract.
Zaugg et al. "Modification of Hemoglobin With Analogs of Aspirin", The Journal of Biological Chemistry, 255(7): 2816-2821, 1980.
International Preliminary Report on Patentability Dated Apr. 4, 2013 From the International Bureau of WIPO Re. Application No. PCT/IL2011/000752.
Examination Report Dated Dec. 31, 2012 From the Government of India, Patent Office, Intellectual Property Building Re. Application No. 2042/CHENP/2008.
Requisition by the Examiner Dated Feb. 4, 2013 From the Canadian Intellectual Property Office Re. Application No. 2,560,905.
Cinatl Jr. et al. "Induction of Differentiation and Suppression of Malignant Phenotype of Human Neuroblastoma BE(2)-C Cells by Valproic Acid: Enhancement by Combination With Interferon-Alpha", International Journal of Oncology, 20(1): 97-106, Jan. 2002.
Official Action Dated Jun. 25, 2013 From the US Patent and Trademark Office Re. U.S. Appl. No. 13/586,913.
Supplementary European Search Report and the European Search Opinion Dated Jun. 25, 2013 From the European Patent Office Re. Application No. 11746937.9.
Translation of Notification of Office Action Dated May 31, 2013 From the State Intellectual Property Office of the People's Republic of China Re. Application No. 201180020723.2.
Translation of Office Action Dated Apr. 25, 2013 From the State Intellectual Property Office of the People's Republic of China Re. Application No. 201080062943.7.
Translation of Search Report Dated Apr. 25, 2013 From the State Intellectual Property Office of the People's Republic of China Re. Application No. 201080062943.7.
Translation of Search Report Dated May 31, 2013 From the State Intellectual Property Office of the People's Republic of China Re. Application No. 201180020723.2.
Doerwald "Side Reactions in Organic Synthesis", A Guide to Succesful Synthesis Desig, Wiley-VCH Verlag, 4 P., 2005.
Ihara et al. "Noncovalent Binding of Small Ubiquitin-Related Modifier (SUMO) Protease to SUMO Is Necessary for Enzymatic Activities and Cell Growth", The Journal of Biological Chemistry, 282(22): 16465-16475, Jun. 1, 2007.
Nudelmann et al. "A Mutual Prodrug Ester of GABA and Perphenazine Exhibits Antischizophrenic Efficacy with Diminished Extrapyramidical Effects", Journal of Medical Chemistry 51(9) XP002698200, p. 2858-2862, 2008. Scheme 1, Compound (3) with HX Being CH3S03H.
Official Action Dated Jul. 12, 2013 From the US Patent and Trademark Office Re. U.S. Appl. No. 12/963,959.
Restriction Official Action Dated Aug. 5, 2013 From the US Patent and Trademark Office Re. U.S. Appl. No. 13/825,369.
Drugs "BioLineRx Successfully Completes Phase 1 Clinical Trials of BL-1020, First in Class GABA-Enhanced Antipsychotic for the Treatment of Schizophrenia", Drugs.com, Drug Information Online, 4 P., Feb. 13, 2007.
Geffen et al. "BL-1020: A Novel Antipsychotic Drug With GABAergic Activity and Low Catalepsy, Is Efficacious in A Rat Model of Schizophrenia", European Neuropsychopharmacology, 19: 1-3, 2009.
Ilaynes et al. "Occurence of Pharmaceutically Acceptable Anions and Cations in the Cambridge Structural Database", Journal of Pharmaceutical Sciences, 94(10): 2111-2120, Oct. 2005.
Schultz et al. "Schizophrenia: A Review", American Family Physician, 75(12): 1821-1829, Jun. 15, 2007.

* cited by examiner

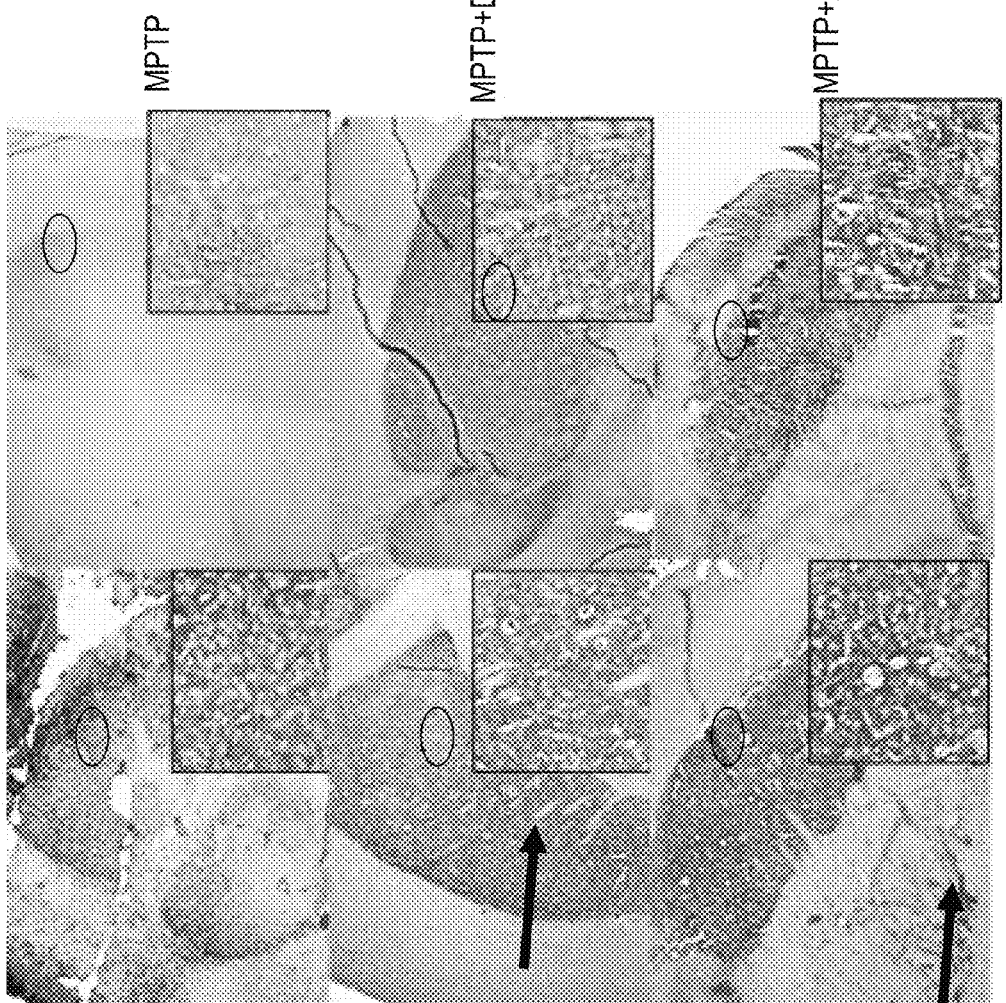

CONJUGATES FOR TREATING NEURODEGENERATIVE DISEASES AND DISORDERS

RELATED APPLICATIONS

This application is a continuation of U.S. patent application Ser. No. 12/867,055 filed on Oct. 28, 2010, which is a National Phase of PCT Patent Application No. PCT/IL2009/000158 having International filing date of Feb. 11, 2009, which claims the benefit of priority of U.S. Provisional Patent Application No. 61/064,017 filed on Feb. 11, 2008. The contents of the above Applications are all incorporated herein by reference.

FIELD AND BACKGROUND OF THE INVENTION

The present invention, in some embodiments thereof, relates to novel compounds, to pharmaceutical compositions containing same and to uses thereof in the treatment of neurodegenerative diseases and disorders, such as Parkinson's disease.

Parkinson's disease is an age-related disorder characterized by progressive loss of dopamine producing neurons in the substantia nigra of the midbrain, which in turn leads to progressive loss of motor functions manifested through symptoms such as tremor, rigidity and ataxia. Parkinson's disease can be treated by administration of pharmacological doses of the precursor of dopamine, L-DOPA (Marsden, Trends Neurosci. 9:512, 1986; Vinken et al., in Handbook of Clinical Neurology p. 185, Elsevier, Amsterdam, 1986). Although such treatment is effective in early stage Parkinson's patients, progressive loss of substantia nigra cells eventually leads to an inability of remaining cells to synthesize sufficient dopamine from the administered precursor and to diminishing pharmacogenic effect.

Recently, Neurologix Inc. announced interim results of a gene therapy clinical trial for patients with Parkinson's disease. The gene therapy involved transforming target brain cells with glutamic acid decarboxylase (GAD) gene to thereby increase GABA synthesis in the brain. According to the interim report (wwwdotbiologynewsdotnet/archives/2005/09/25/neurologix_announces_positive_results_of_gene_therapy_ clinical_trial_in_parkinsons_ diseasedothtml), treated Parkinson's disease patients exhibited statistically significant improvement in motor function and a strong trend toward improvement of activities of daily living.

Unfortunately, clinical use of GABA for treating neurodegenerative disorders is presently limited since the GABA molecule comprises hydrophilic functional groups (e.g., a free carboxylic acid group and a free amino group) and therefore does not effectively cross the blood brain barrier (BBB).

In an attempt to overcome the limitations associated with the administration of GABA to the brain, Prof. Nudelman and co-researchers, which are co-inventors of the present invention, have designed and successfully practiced a series of conjugates of psychotropic drugs and GABA. These conjugates and their advantageous use in the treatment of psychotic and/or proliferative diseases and disorders are described in detail in International Patent Application published as WO 03/026563, which is incorporated by reference as if fully set forth herein.

Accordingly, International Patent Application WO 2005/092392, by the same inventors, which is also incorporated by reference as if fully set forth herein, teach psychotropic drugs coupled to GABA.

SUMMARY OF THE INVENTION

The present invention, in some embodiments thereof, provides novel conjugates of L-DOPA and GABA; which can be used safely and effectively in treating neurodegenerative disorders, such as Parkinson's disease.

According to one aspect of embodiments of the invention there is provided a conjugate comprising L-DOPA covalently linked to at least one γ-aminobutyric acid (GABA) moiety. The conjugate can be in a form of a pharmaceutically acceptable salt thereof.

According to another aspect of embodiments of the invention there is provided a pharmaceutical composition comprising, as an active ingredient, a conjugate comprising L-DOPA covalently linked to at least one GABA moiety and a pharmaceutically acceptable carrier.

According to yet another aspect of embodiments of the invention there is provided an article-of-manufacturing comprising a pharmaceutical composition which comprises, as an active ingredient, a conjugate comprising L-DOPA covalently linked to at least one GABA moiety and a pharmaceutically acceptable carrier, the composition being packaged in a packaging material and identified in print, on or in the packaging material, for use in the treatment of a neurodegenerative disease or disorder According to still another aspect of embodiments of the invention there is provided a method of treating a neurodegenerative disease or disorder. The method is effected by administering to a subject in need thereof a therapeutically effective amount of a conjugate comprising L-DOPA covalently linked to at least one GABA moiety, thereby treating the neurodegenerative disease or disorder disease.

According to an additional aspect of embodiments of the invention there is provided use of a conjugate comprising L-DOPA covalently linked to at least one GABA moiety in the preparation of a medicament.

According to some embodiments the medicament is for treating a neurodegenerative disease or disorder.

According to some embodiments of the invention described below, the conjugate comprises a single GABA moiety linked to L-DOPA.

According to some embodiments, the conjugate comprises two GABA moieties linked to L-DOPA.

According to some embodiments, the conjugate comprises three GABA moieties linked to L-DOPA.

According to some embodiments, the L-DOPA and each of GABA moieties are linked therebetween via a covalent bond selected from the group consisting of a carboxylic ester bond, an alkyloxy carboxylic ester bond and an amide bond.

According to some embodiments, the covalent bond is an amide bond and a GABA moiety is linked to an amine functional group of L-DOPA (when non-conjugated).

According to some embodiments, the covalent bond is an ester bond and a GABA moiety is linked to one or both hydroxy groups of L-DOPA (when non-conjugated).

According to some embodiments, the covalent bond is an alkyloxy carboxylic ester bond and a GABA moiety is linked to the carboxylic acid group of L-DOPA (when non-conjugated).

According to some embodiments, the neurodegenerative disease or disorder is Parkinson's disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
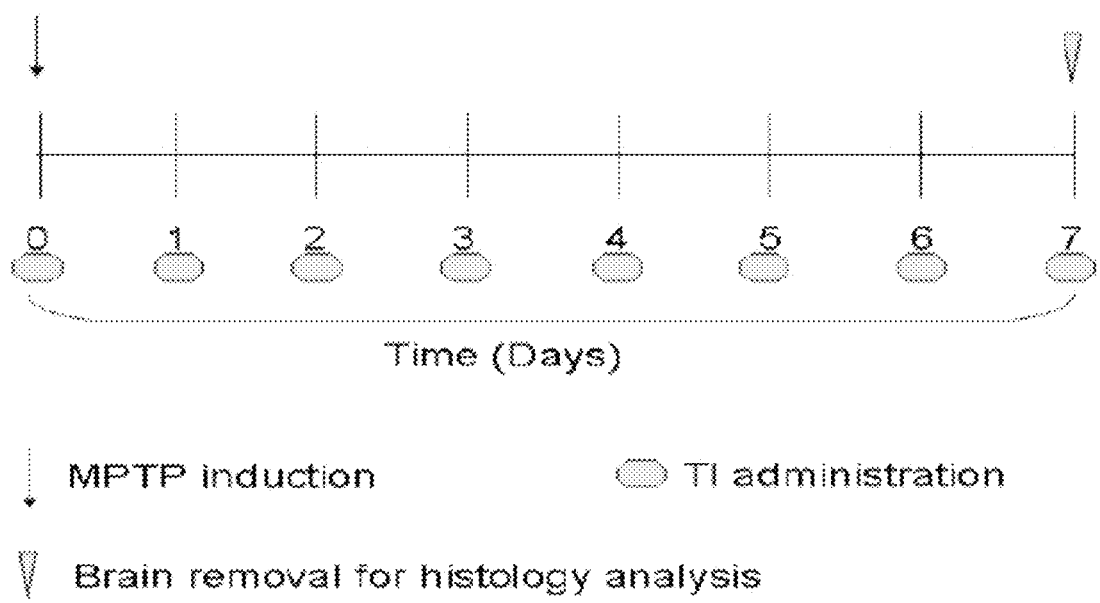
Figure 2A:
Figure 2B:
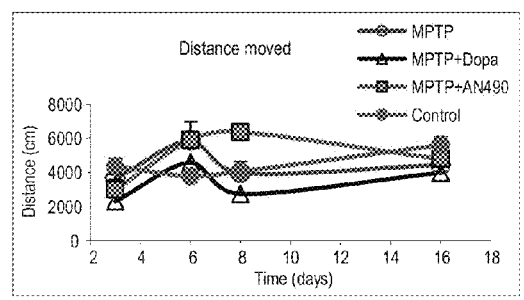
Figure 2C:
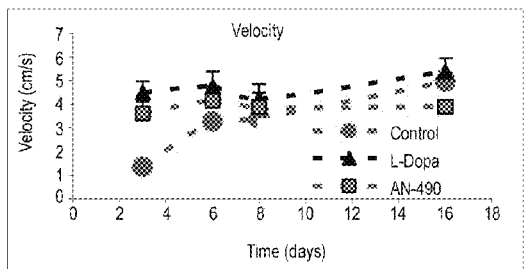
Figure 2D:
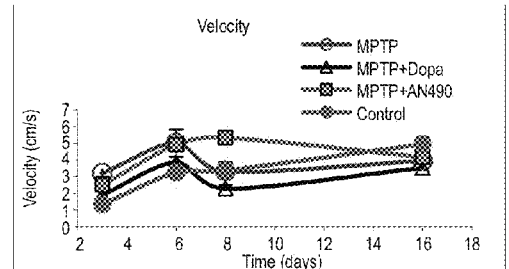
Figure 2E:
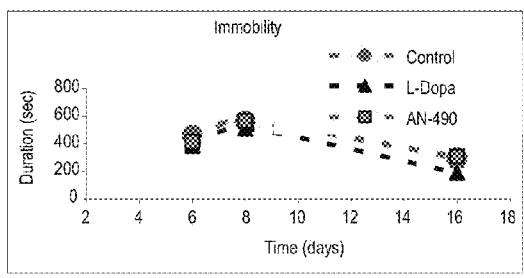
Figure 2F:
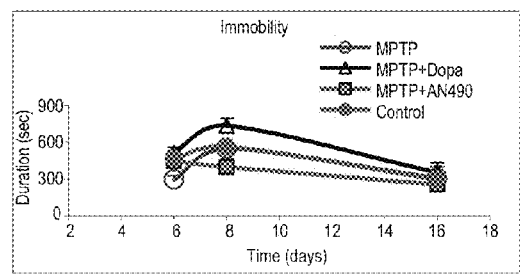
Figure 2G:
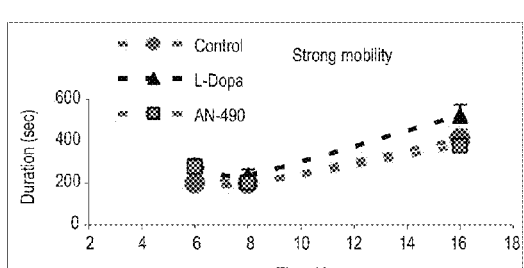
Figure 2H:
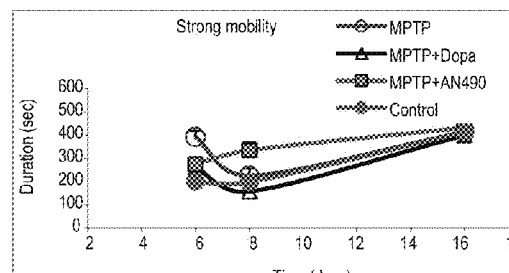

FIG. 1 presents a schematic representation of the protocol used in the experiments described in Example 2 hereinbelow for examining the protective effect of BL-1023, an L-DOPA-GABA conjugate according to some embodiments of the invention, in a MPTP acute toxicity model. Mice were administered 4 injections IP of MPTP (each injection contained 20 mg/kg, 5 ml/kg) or saline alone (control) at 2 hours intervals on day 0. Mice were then administered subcutaneously test solutions (TI) (either saline, L-DOPA or BL-1023) once daily throughout the 8 successive treatment days (days 0-7). On day 7, the mice were sacrificed and their brains were removed for immunohistochemistry analysis of the number of tyrosine hyroxylase immunostained cells at the level of the Substantia Nigra (SNpc).

FIGS. 2(A-H) present comparative plots showing the data obtained in an open field test for examining the protective effect of AN-490, an L-DOPA-GABA conjugate according to some embodiments of the invention, in a MPTP acute toxicity model. Mice were administered the following treatments: saline (filled red circles connected with a dashed red line, Control), L-DOPA 25 mg/kg (filled black triangles connected with a dashed black line, L-DOPA), AN-490 67.5 mg/kg (filled green squares connected with a dashed green line, AN-490), MPTP (empty blue circles connected with a blue line, MPTP), MPTP+L-DOPA 25 mg/kg (empty black triangles connected with a black line, MPTP+DOPA) and MPTP+AN-490 67.5 mg/kg (filled green squares connected with a green line, MPTP+AN-490). The MPTP neurotoxin was administered on day 0, with 4 IP injections (each injection contained 20 mg/kg, 5 ml/kg) in saline. The various treatments or saline were administered on days 0, 1, 2, 3, 6, 7, 13 and 16. Each group of mice (n=6) was subjected, on days 3, 6, 8 and 16, to the open field test, and the following parameters were scored: the distance moved (FIGS. 2A and 2B), velocity (FIGS. 2C and 2D), time spent immobile (FIGS. 2E and 2F) and time spent in a high level of mobility (FIGS. 2G and 2H; strong mobility) during a period of 20 minutes. FIGS. 2A, 2C, 2E and 2G present the data obtained for the control mice, mice treated with L-DOPA and mice treated with AN-490. FIGS. 2B, 2D, 2F and 2H present the data obtained for control mice or mice treated with MPTP, MPTP with L-DOPA and MPTP with AN-490. The group of mice which received the MPTP+AN-490 exhibited the highest velocity (FIG. 2B), was highly mobile (FIG. 2H) and was immobile for a short time (FIG. 2F) as compared to the other tested groups.

Figure 3A:
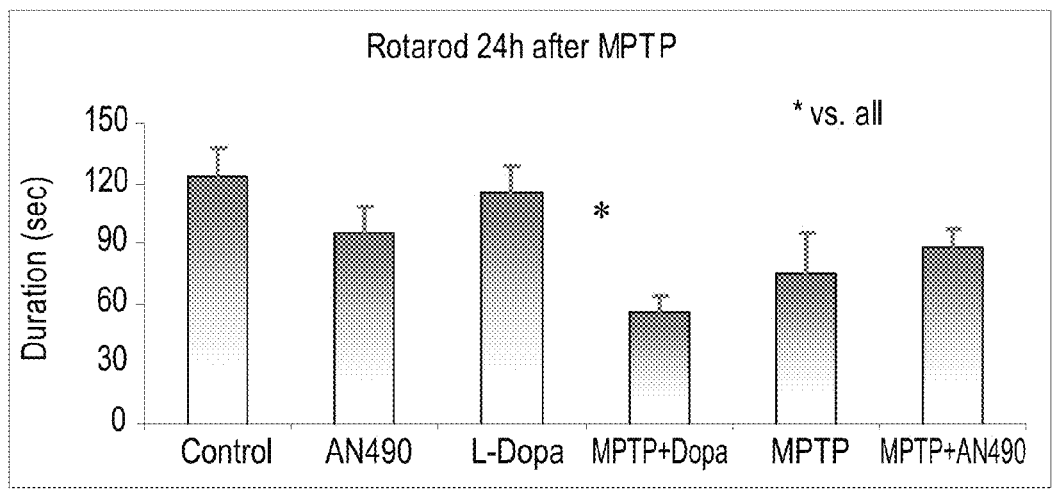
Figure 3B:
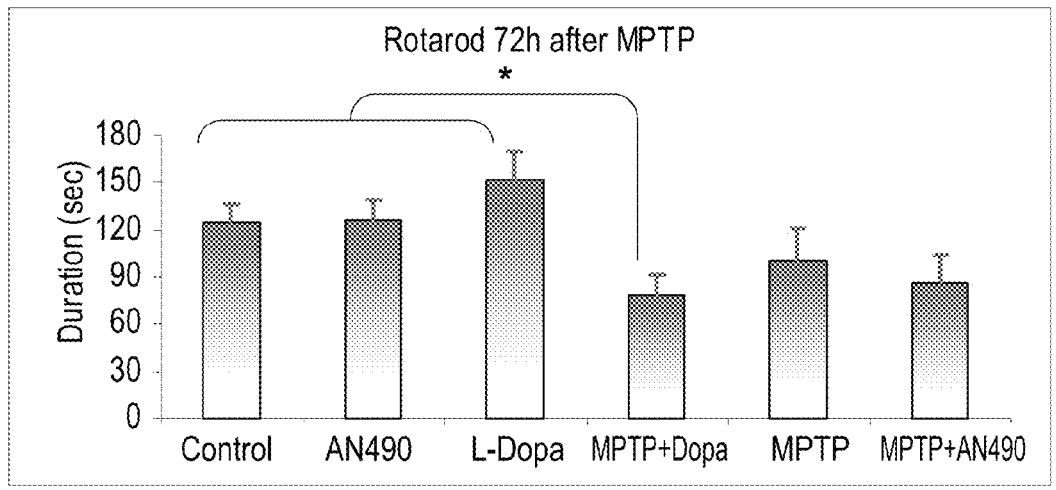
Figure 3C:
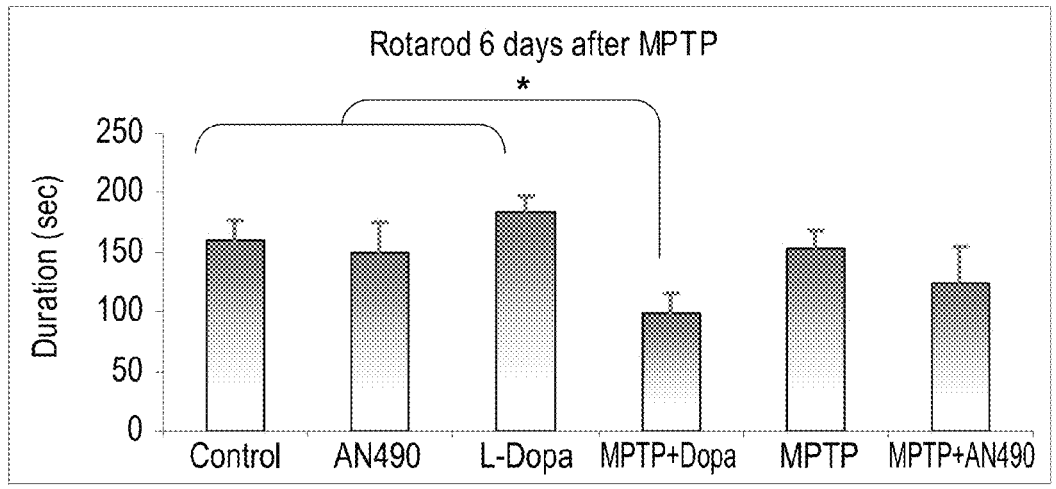

FIGS. 3(A-C) present bar graphs showing the RotaRod test results obtained for examining the protective effect of AN-490, an L-DOPA-GABA conjugate according to some embodiments of the invention, in a MPTP acute toxicity model. Mice were administered the following treatments: saline (Control), L-DOPA 25 mg/kg, AN-490 67.5 mg/kg, MPTP, MPTP+L-DOPA 25 mg/kg, and MPTP+AN-490 67.5 mg/kg. The MPTP neurotoxin was administered on day 0, with 4 IP injections (each injection contained 20 mg/kg, 5 ml/kg) in saline. The various treatments or saline were administered on days 0, 1, 2, 3, 6, 7, 13 and 16. Each group of mice (n=6) was subjected, on days 1, 3 and 6, to the RotaRod test. Each mouse was tested 3 times and the average value for the performance (average duration on rod i.e. latency) of each group on day 1 (FIG. 3A), 3 (FIG. 3B) and 6 (FIG. 3C) are presented.

Figure 4:
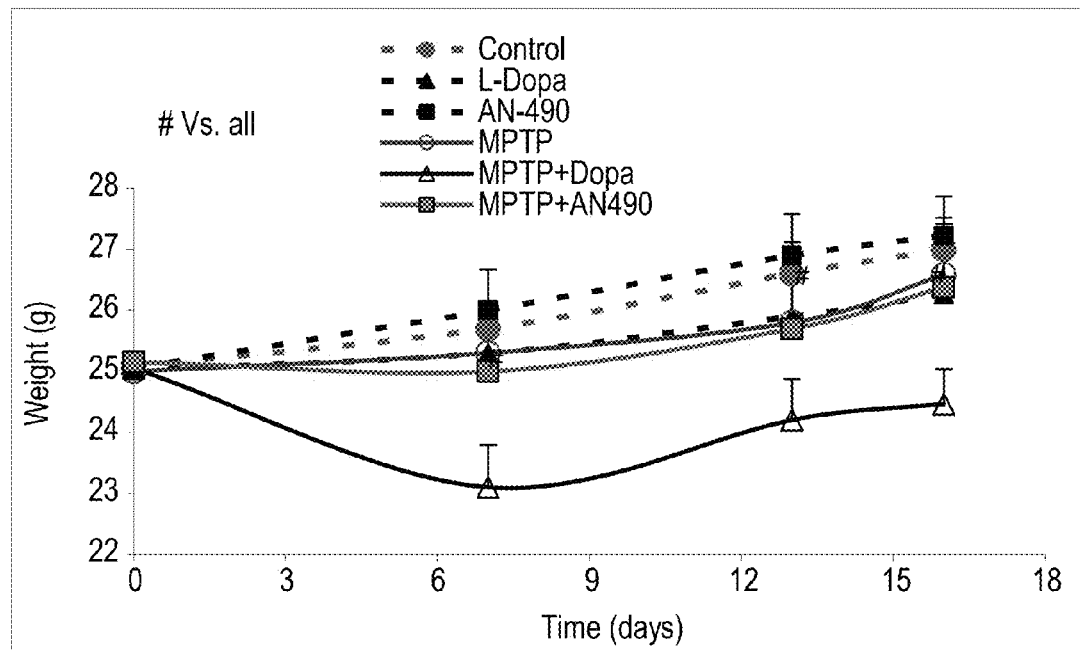

FIG. 4 presents comparative plots showing the change in mice weight during the MPTP acute toxicity model (as presented in Experiment 3), following treatment with: saline (filled red circles connected with a dashed red line, Control), L-DOPA 25 mg/kg (filled black triangles connected with a dashed black line, L-DOPA), AN-490 67.5 mg/kg (filled black squares connected with a dashed black line, AN-490), MPTP (empty blue circles connected with a blue line, MPTP), MPTP+L-DOPA 25 mg/kg (empty black triangles connected with a black line, MPTP+DOPA), MPTP+AN-490 67.5 mg/kg (filled green squares connected with a green line, MPTP+AN-490).

Figure 5:
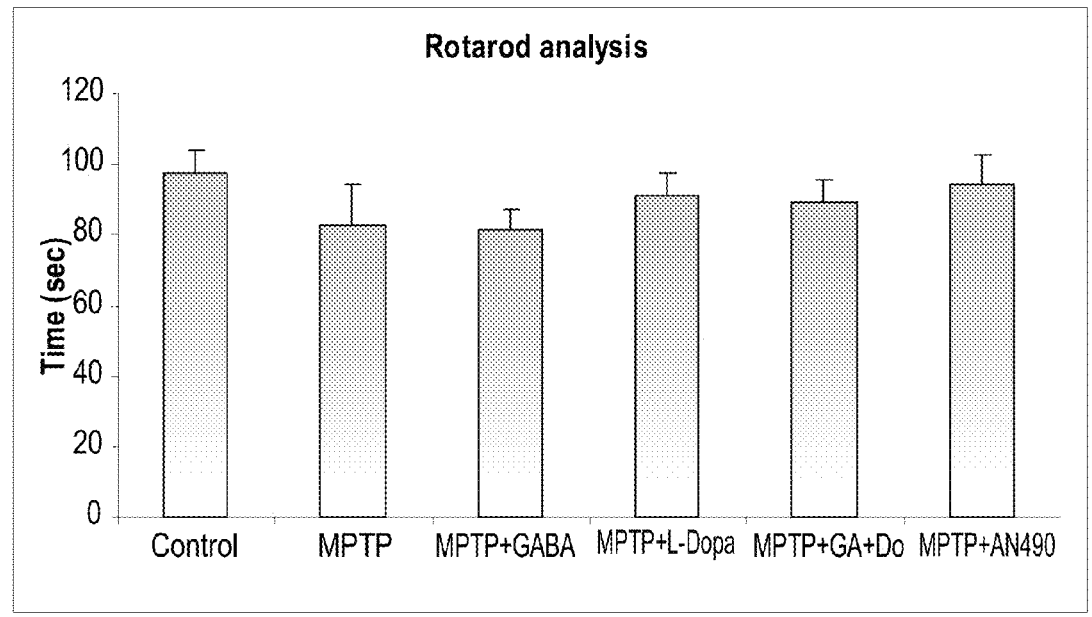

FIG. 5 presents a bar graph showing the RotaRod test results obtained for examining the protective effect of AN-490, an L-DOPA-GABA conjugate according to some embodiments of the invention, in a MPTP sub-acute toxicity model. Mice were administered the following treatments: saline (Control), MPTP+saline (MPTP), MPTP+GABA.HCl 18.4 mg/kg (MPTP+GABA), MPTP+L-DOPA 30 mg/kg (MPTP+L-DOPA), MPTP+L-DOPA 30 mg/kg+GABA 18.4 mg/kg (MPTP-Ga+Do) and MPTP+AN-490 81 mg/kg (MPTP+AN-490). The MPTP neurotoxin was administered on days 0, 1, 2, 3, 4 and 5 as one IP injection of MPTP at a dose of 20 mg/kg. The various treatments or saline were administered starting from day 13, every day for 6 consecutive days and in the following week. Treatment was then reduced to 3 days a week. Each group of mice (n=6) was then subjected, on day 24, to the RotaRod test and the data observed for the average duration on Rod, tested three times, are presented.

Figure 6:
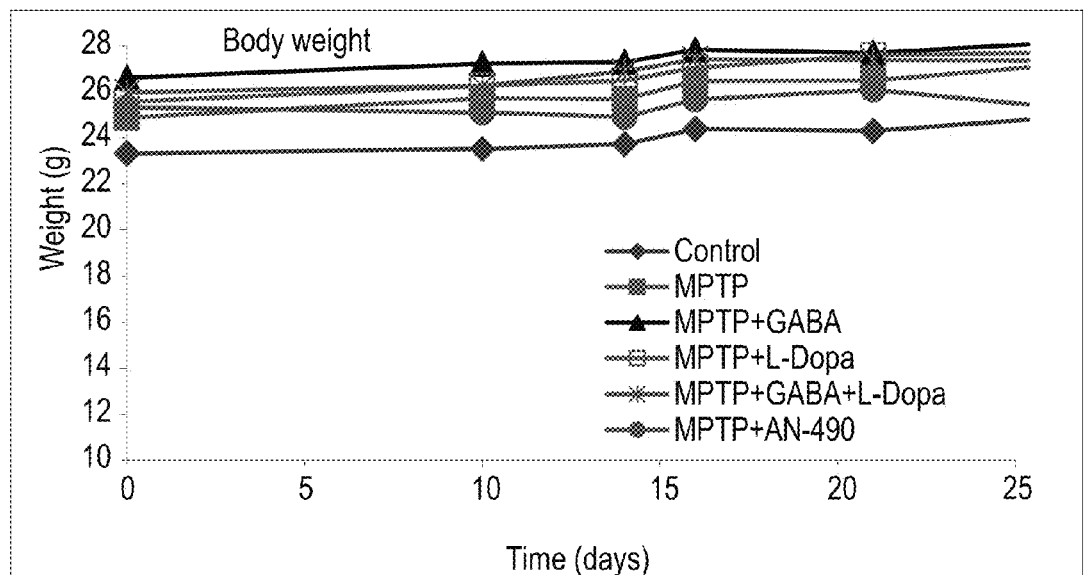

FIG. 6 presents comparative plots showing the change in mice weight during the MPTP sub-acute toxicity model (Experiment 3), following treatment with: saline (blue filled diamonds, Control), MPTP+saline (pink filled squares, MPTP), MPTP+GABA.HCl 18.4 mg/kg (black filled triangles), MPTP+L-DOPA 30 mg/kg (empty red squares), MPTP+L-DOPA 30 mg/kg+GABA 18.4 mg/kg (purple cross) and MPTP+AN-490 81 mg/kg (brown circle).

Figure 7:
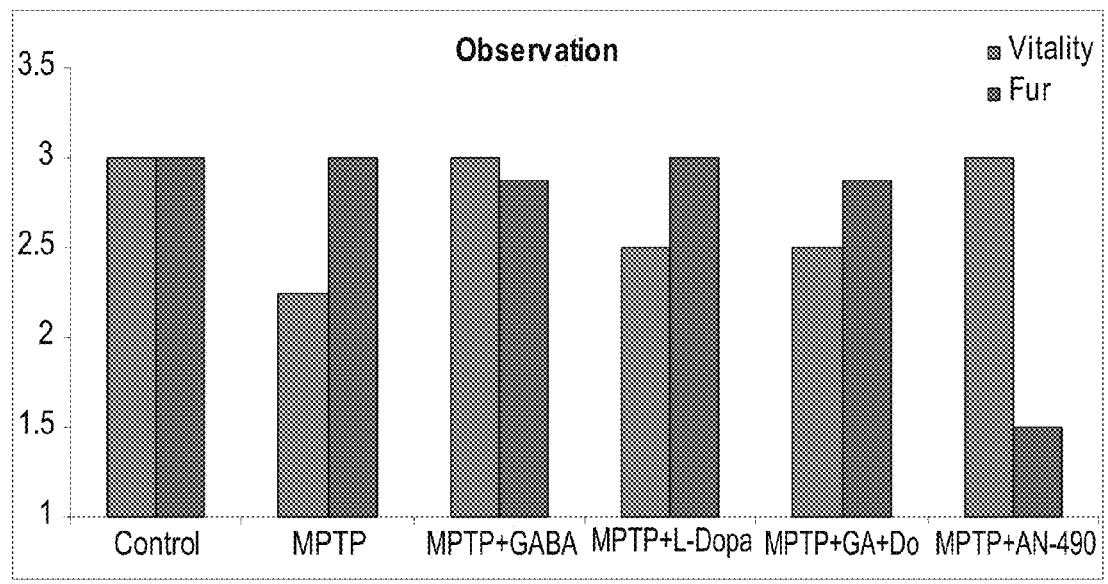

FIG. 7 presents a bar graph showing the observed vitality signs of mice during the MPTP sub-acute toxicity model (Experiment 3), as described for FIG. 6 hereinabove. Six independent observers estimated the level of mice vitality by the level of motion of the mice (light purple, marked vitality) and fur appearance (dark purple). The results are an average of the observers' reports.

FIGS. 8(A-F) present representative microphotographs of tyrosine hydroxylase immunostaining of the striatum and substantia-nigra of mice, showing the protective effect of AN-490 against MPTP neurotoxicity, in the MPTP sub-acute toxicity model (Experiment 3). Shown are microphotograph of the striatum and substantia-nigra of mice receiving saline (FIG. 8A, Naive), MPTP+saline (FIG. 8B, MPTP) MPTP+ GABA.HCl 18.4 mg/kg (FIG. 8C, MPTP+GABA), MPTP+ L-DOPA 30 mg/kg (FIG. 8D, MPTP+DOPA), MPTP+L-DOPA 30 mg/kg+GABA 18.4 mg/kg (FIG. 8E, MPTP+ Dopa+GABA) and MPTP+AN-490 81 mg/kg (FIG. 8F, MPTP+AN490). Paraffin-embedded horizontal sections of the stratium and substantia nigra were stained with hematoxylan and Tyrosine Hyroxylase antibodies. The magnification is ×100 and in the insert ×200.

Figure 9A:
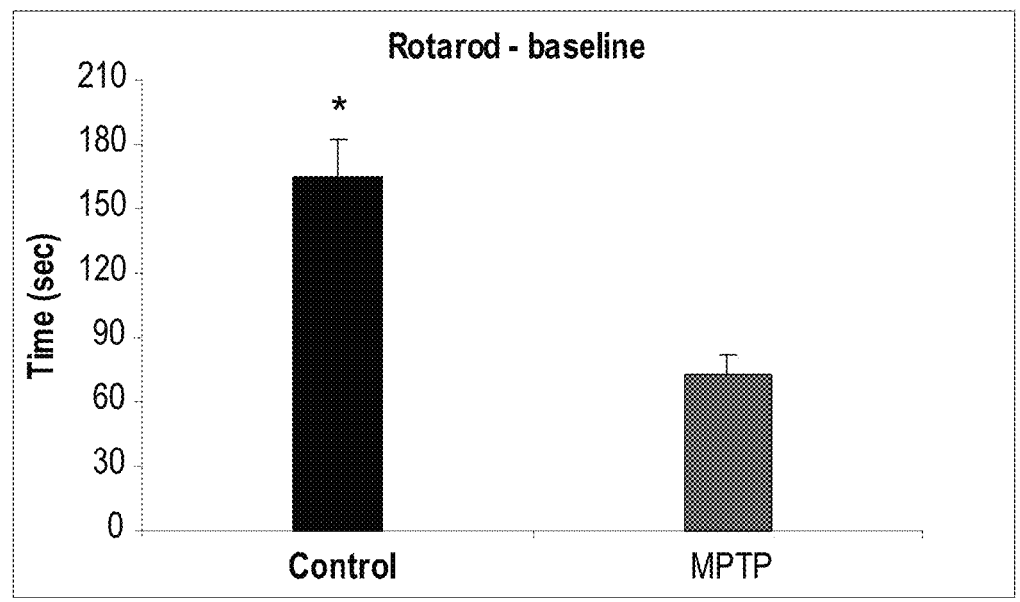
Figure 9B:
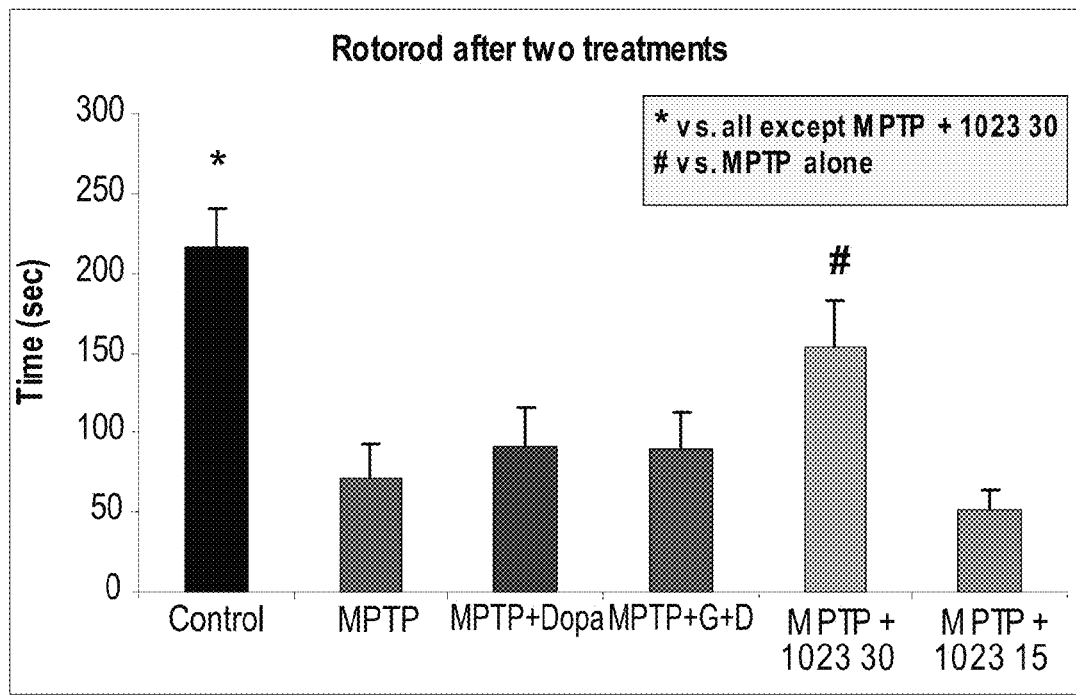

FIGS. 9(A-B) present bar graphs showing the RotaRod test results obtained for examining the protective effect of BL-1023* (denoted 1023), an L-DOPA-GABA conjugate according to some embodiments of the invention, in a MPTP acute toxicity model (Experiment 3). Mice were administered the following treatments: saline (Control), MPTP+saline (MPTP), MPTP+L-DOPA 30 mg/kg (MPTP+Dopa), MPTP+ L-DOPA 30 mg/kg+GABA 18.4 mg/kg (MPTP+G+D) MPTP+BL1023* 48.4 mg/kg (MPTP+1023 30) and MPTP+ BL-1023* 24.2 mg/kg (MPTP+BL1023 15). The MPTP neurotoxin was administered on day 0, with 4 IP injections (each injection contained 20 mg/kg, 5 ml/kg) in saline. The various treatments or saline were administered on day 7, 9, 11 and 13 (total of 4 treatments). Each group of mice (n=10) was subjected to the RotaRod test, on day 6 (before initiation of treatment, FIG. 9A) and day 12 (after initiation of treatment, FIG. 9B) and the observed average duration on Rod, tested three times, are presented. The results show that while MPTP administration led to a reduction in the mice duration on the Rod (#p<0.05), BL-1203* administration, at a dose of 48.4 mg/kg, was able to reverse the observed MPTP-dependent reduction (*p<0.05).

Figure 10A:
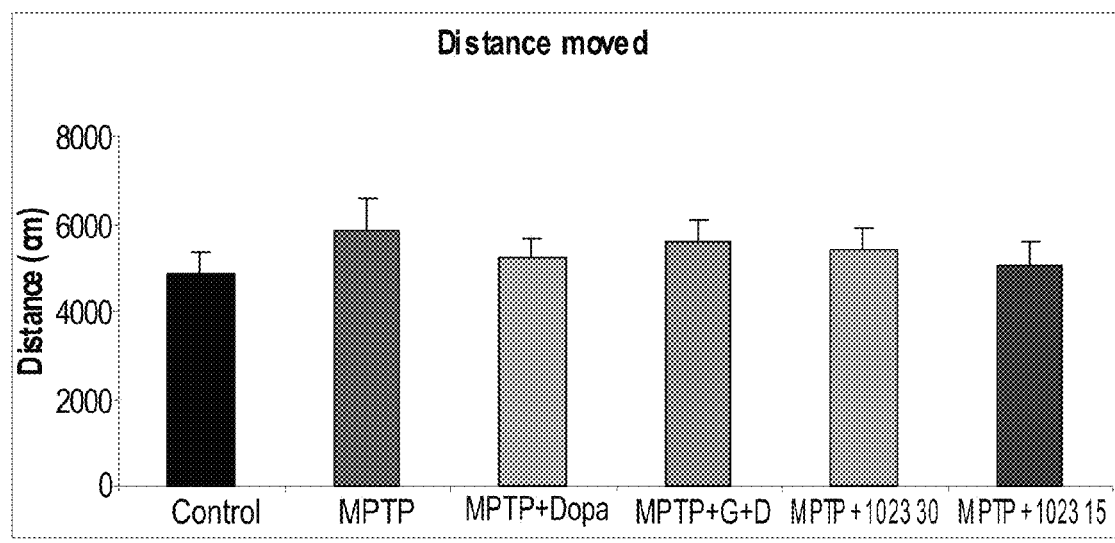
Figure 10B:
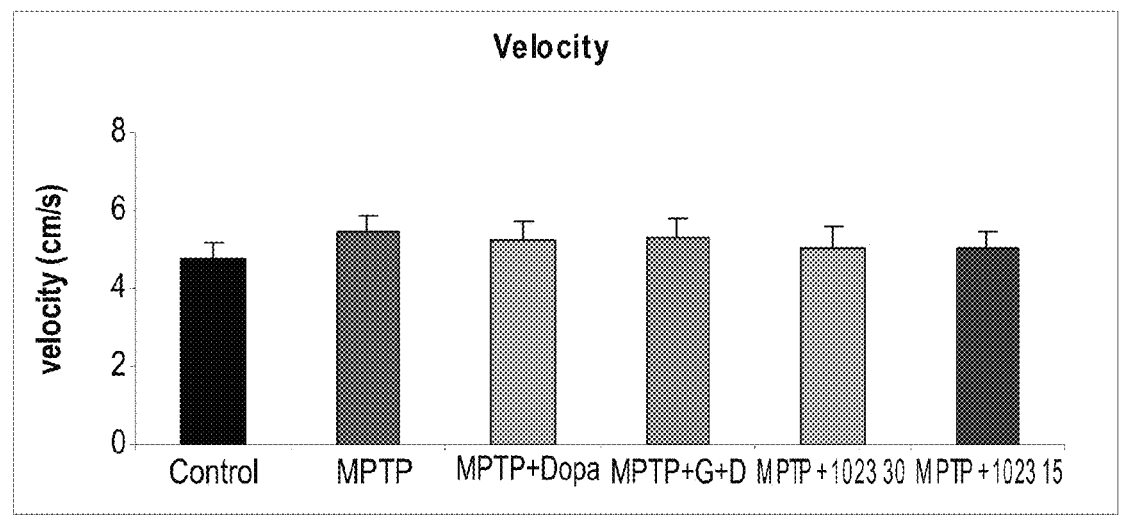

FIGS. 10(A-B) present bar graphs showing data obtained in an open field test for examining the protective effect of BL-1023* (denoted 1023), an L-DOPA-GABA conjugate according to some embodiments of the invention, in a MPTP acute toxicity model (Experiment 3). Mice were administered the following treatments: saline (Control), MPTP+saline (MPTP), MPTP+L-DOPA 30 mg/kg (MPTP+Dopa), MPTP+ L-DOPA 30 mg/kg+GABA 18.4 mg/kg (MPTP+G+D), MPTP+BL1023* 48.4 mg/kg (MPTP+1023 30) and MPTP+ BL-1023* 24.2 mg/kg (MPTP+BL1023 15). The MPTP neurotoxin was administered on day 0, with 4 IP injections (each injection contained 20 mg/kg, 5 ml/kg) in saline. The various treatments or saline were administered on day 7, 9, 11 and 13 (total of 4 treatments) and the measured velocity (FIG. 10A) and distance moved (FIG. 10B) were measured on day 13.

Figure 11:
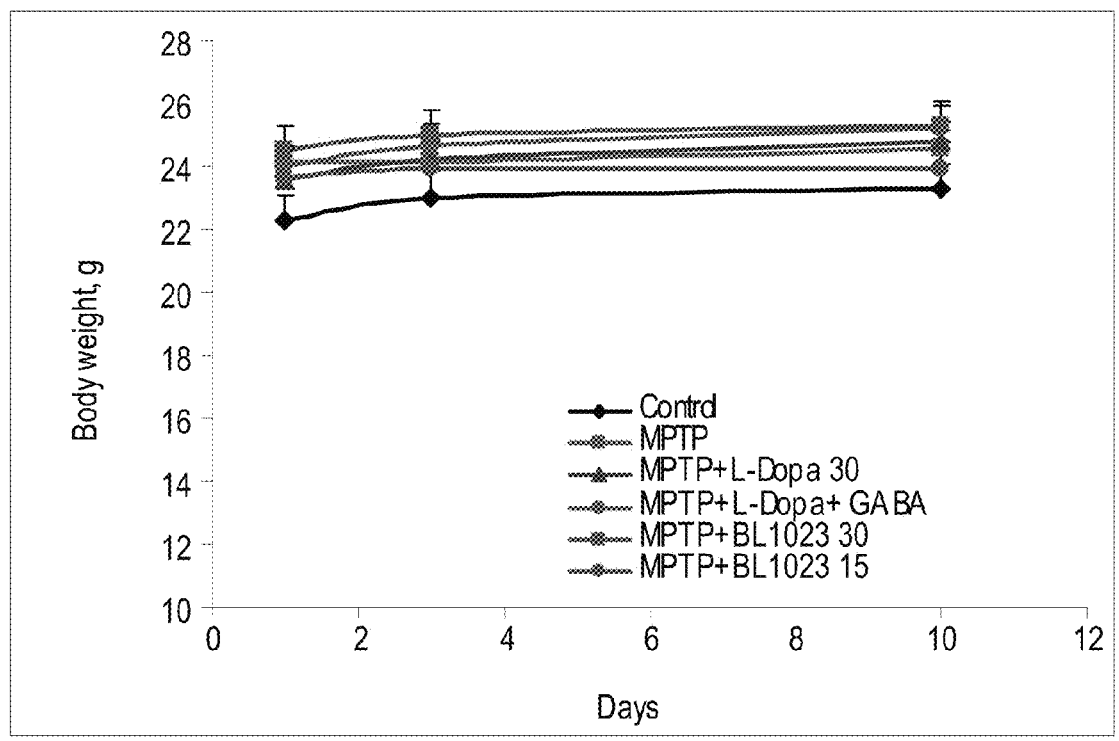

FIG. 11 presents comparative plots showing the change in mice weight during MPTP acute toxicity model (Experiment 3), following treatment with: saline (black filled diamonds, Control), MPTP+saline (red filled squares, MPTP), MPTP+ L-DOPA 30 mg/kg (filled blue triangles), MPTP+L-DOPA 30 mg/kg+GABA 18.4 mg/kg (pink filled circles), MPTP+ BL1023* 48.4 mg/kg (purple filled squares, denoted as MPTP+BL1023 30), and MPTP+BL-1023* 24.2 mg/kg (brown circles, denoted as MPTP+BL1023 15).

Figure 12A:
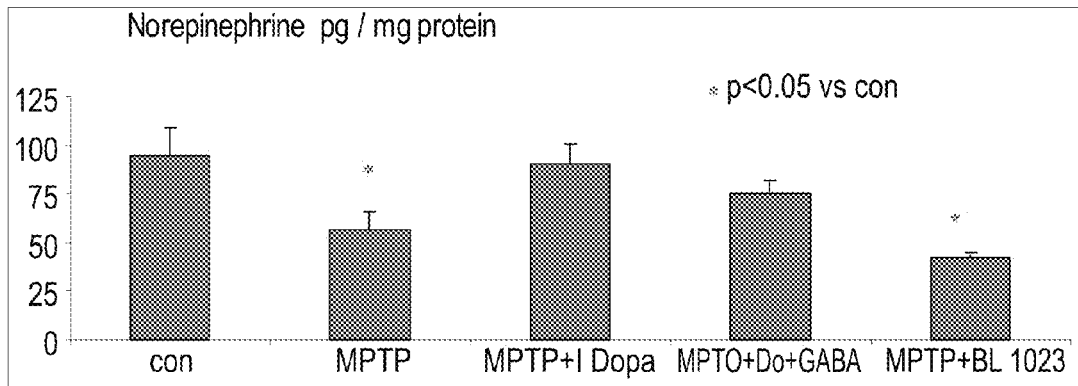
Figure 12B:
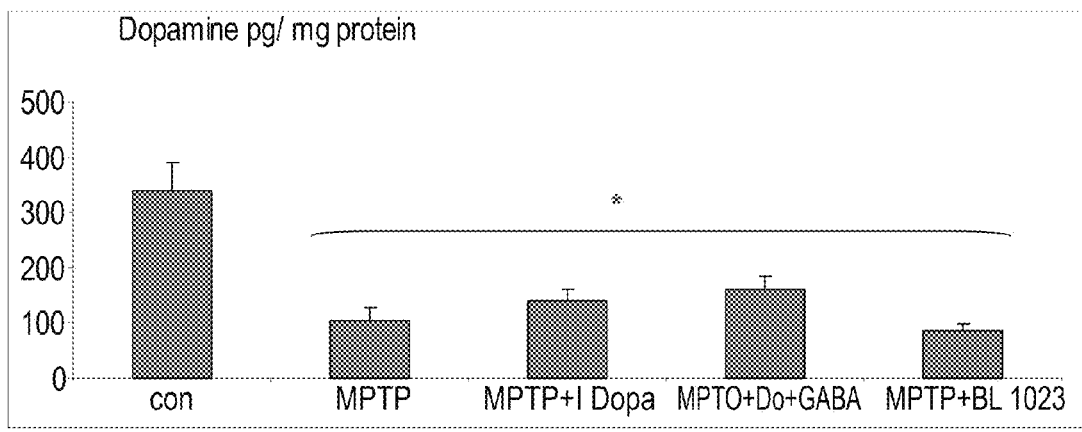
Figure 12C:
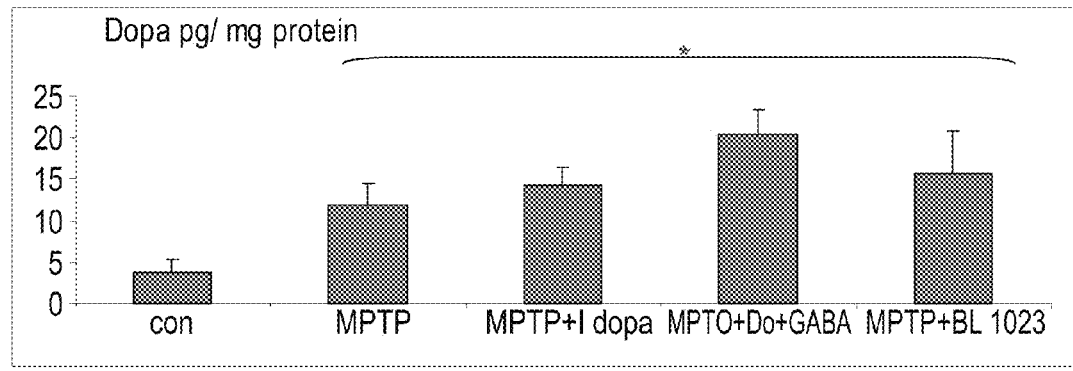

FIGS. 12(A-C) present bar graphs showing the effect of BL-1023* administration on the level of the following catecholamines: norepinephrin (FIG. 12A), dopamine (FIG. 12B) and L-DOPA (FIG. 12C) in mice. Mice were administered the following treatments: saline (Con), MPTP+saline (MPTP), MPTP+L-DOPA 30 mg/kg (denoted as MPTP+1 Dopa), MPTP+L-DOPA 30 mg/kg+GABA 18.4 mg/kg (denoted as MPTO+Do+GABA) and MPTP+BL1023* (MPTP+ BL1023). The MPTP neurotoxin was administered on day 0, with 4 IP injections (each injection contained 20 mg/kg, 5 ml/kg) in saline. The various drugs or saline were administered on day 7, 9, 11 and 13 (total of 4 treatments). Brains (whole brains) of three mice from each group were dissected out on day 14-15 and the catecholamines levels were determined by HPLC, according to the protocol described in the Examples section hereinbelow. Protein content of each sample was determined and the level of the catecholamines was normalized to μg protein. A significant reduction in norepinephrin and dopamine levels or enhancement of L-DOPA levels, as compared to control, is marked by *(p<0.05).

Figure 13:
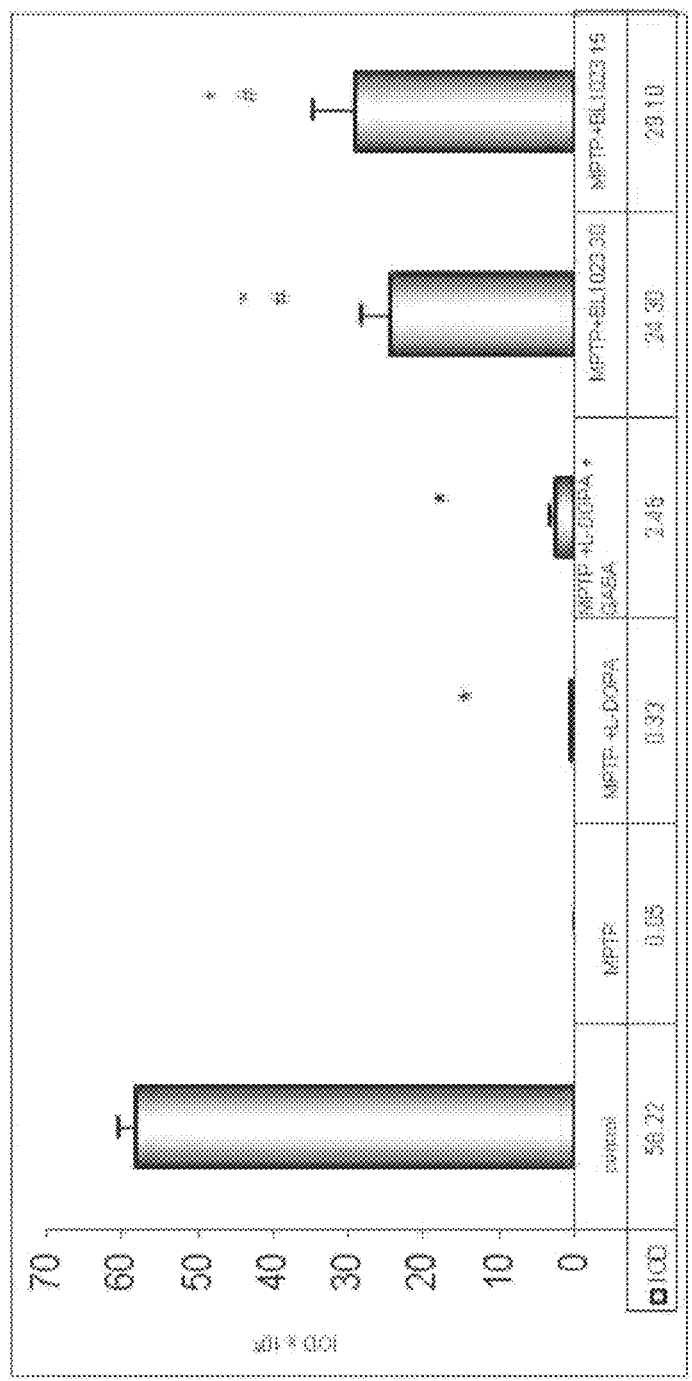

FIG. 13 presents a bar graph showing the effect of BL-1023* administration on the neuronal density in the stratium, as assessed from Tyrosine Hydroxylase staining. Mice were administered the following treatments: saline (control), MPTP+saline (MPTP), MPTP+L-DOPA 30 mg/kg (MPTP+ L-DOPA), MPTP+L-DOPA 30 mg/kg+GABA 18.4 mg/kg (MPTP+L-DOPA+GABA), MPTP+BL1023* 48.4 mg/kg (denoted MPTP+1023 30) and MPTP+BL-1023* 24.2 mg/kg (denoted MPTP+BL1023 15). The MPTP neurotoxin was administered on day 0, with 4 IP injections (each injection contained 20 mg/kg, 5 ml/kg) in saline. The various treatments or saline were administered on day 7, 9, 11 and 13 (total of 4 treatments). Three mice, from each treatment group, and four mice from the control group, were sacrificed on day 15 and subjected to immunohystochemistry for tyrosine hydroxylase of the stratium according to the protocol described in the Examples section hereinbelow. The intensity of Tyrosine Hyroxylase (TH) staining, in the striatum of the treated mice is presented as the average of Intensity Optical Density (IOD) and SE obtained for the total stained area.

Figure 14:
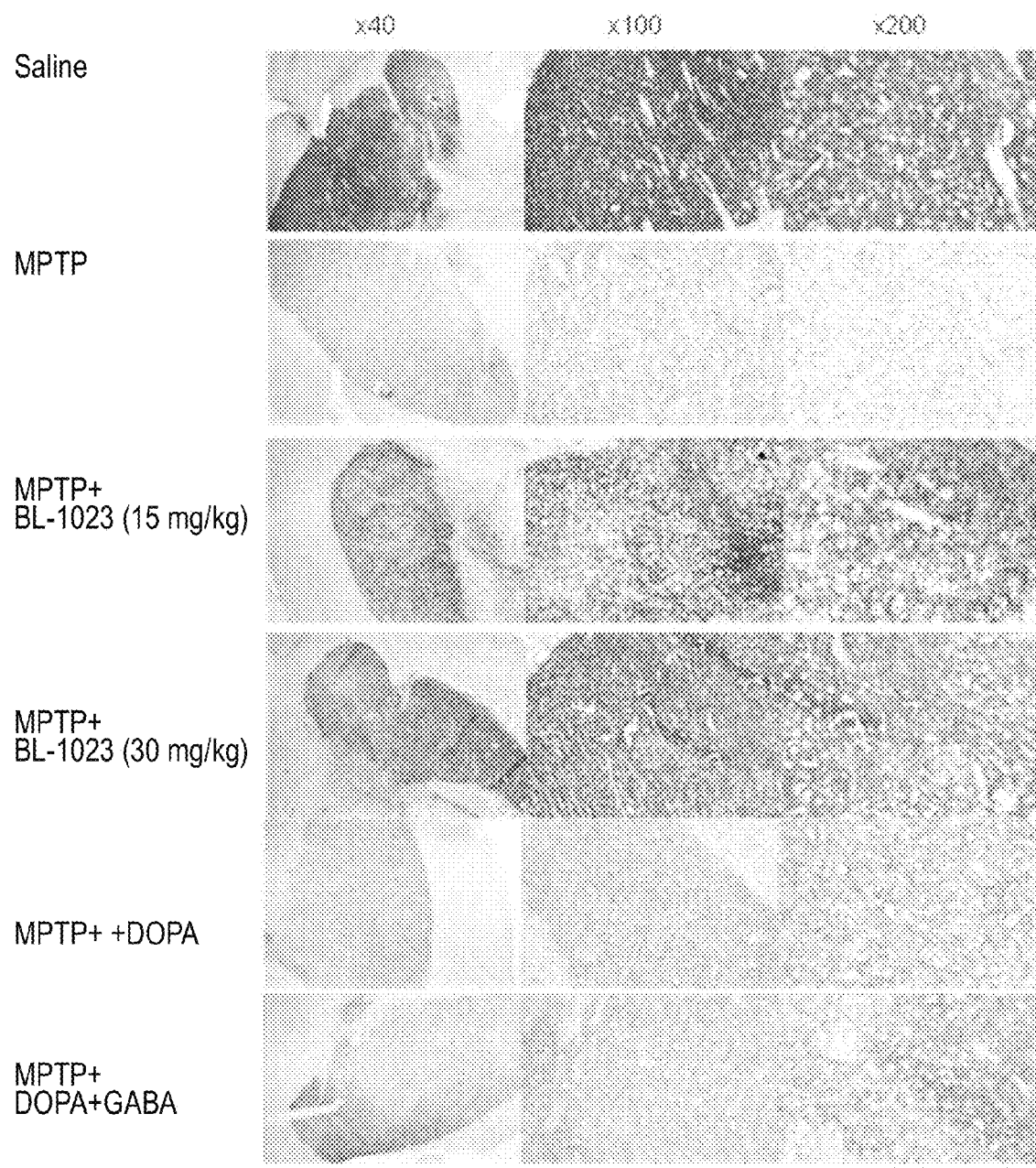

FIG. 14 presents electronic pictures of the Immunohystochemistry (IHC) horizontal sections from the stratium of the mice treated as described in FIG. 13, at ×40, ×100 and ×200 magnification, using ImagePro software.

Figure 15:
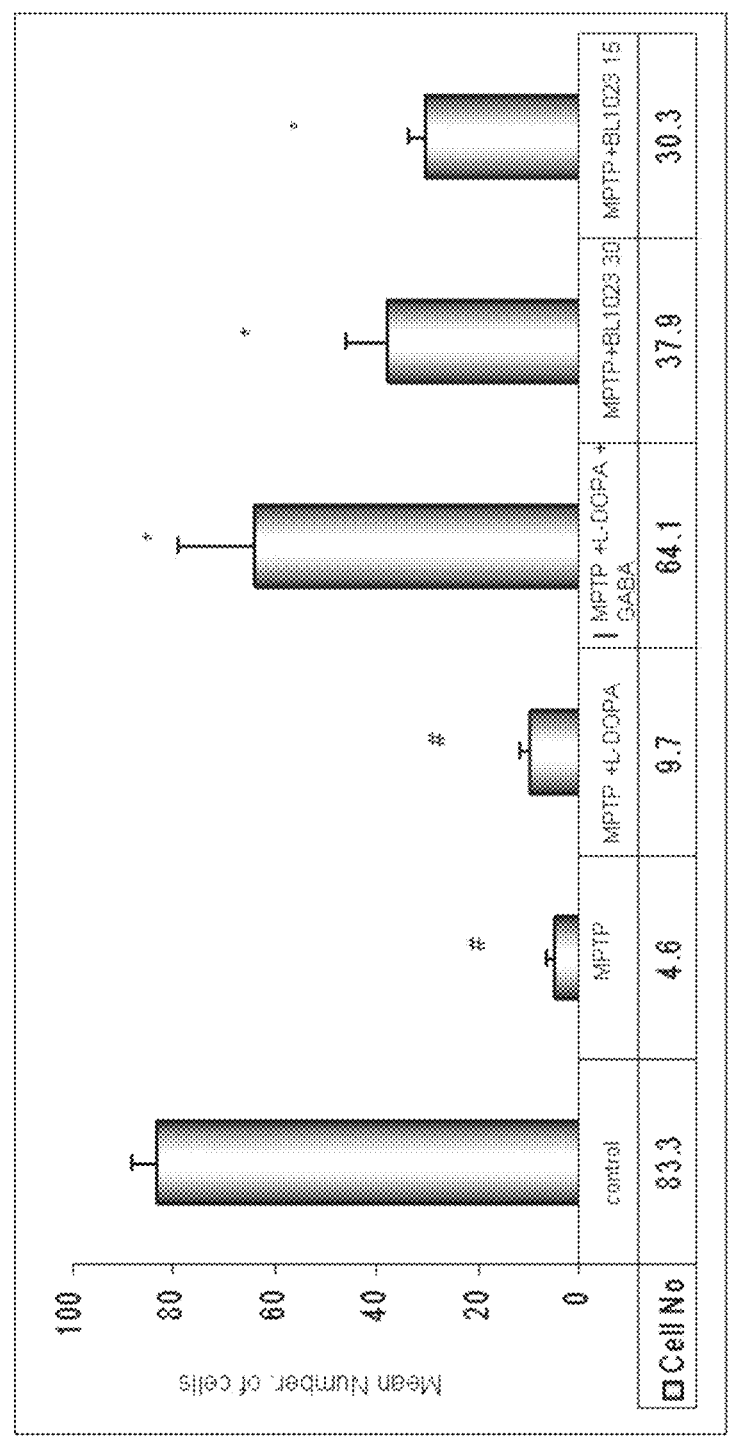

FIG. 15 presents a bar graph showing the effect of BL-1023* administration on the neuronal density in the substantia nigra, as assessed from Tyrosine Hydroxylase staining. Mice were administered the following treatments: saline (control), MPTP+saline (MPTP), MPTP+L-DOPA 30 mg/kg (MPTP+L-DOPA), MPTP+L-DOPA 30 mg/kg+GABA 18.4 mg/kg (MPTP+L-DOPA+GABA), MPTP+BL1023* 48.4 mg/kg (MPTP+1023 30) and MPTP+BL-1023* 24.2 mg/kg (MPTP+BL1023 15). The MPTP neurotoxin was administered on day 0, with 4 IP injections (each injection contained 20 mg/kg, 5 ml/kg) in saline. The various treatments or saline were administered on day 7, 9, 11 and 13 (total of 4 treatments). Three mice, from each treatment group, and four mice from the control group, were sacrificed on day 15 and subjected to immunohystochemistry for tyrosine hydroxylase of the substantia nigra according to the protocol described in the Examples section hereinbelow. The intensity of Tyrosine Hyroxylase (TH) staining, in the substantia nigra of the treated mice is presented as the number of TH stained cells and SE obtained for the total stained area.

Figure 16:
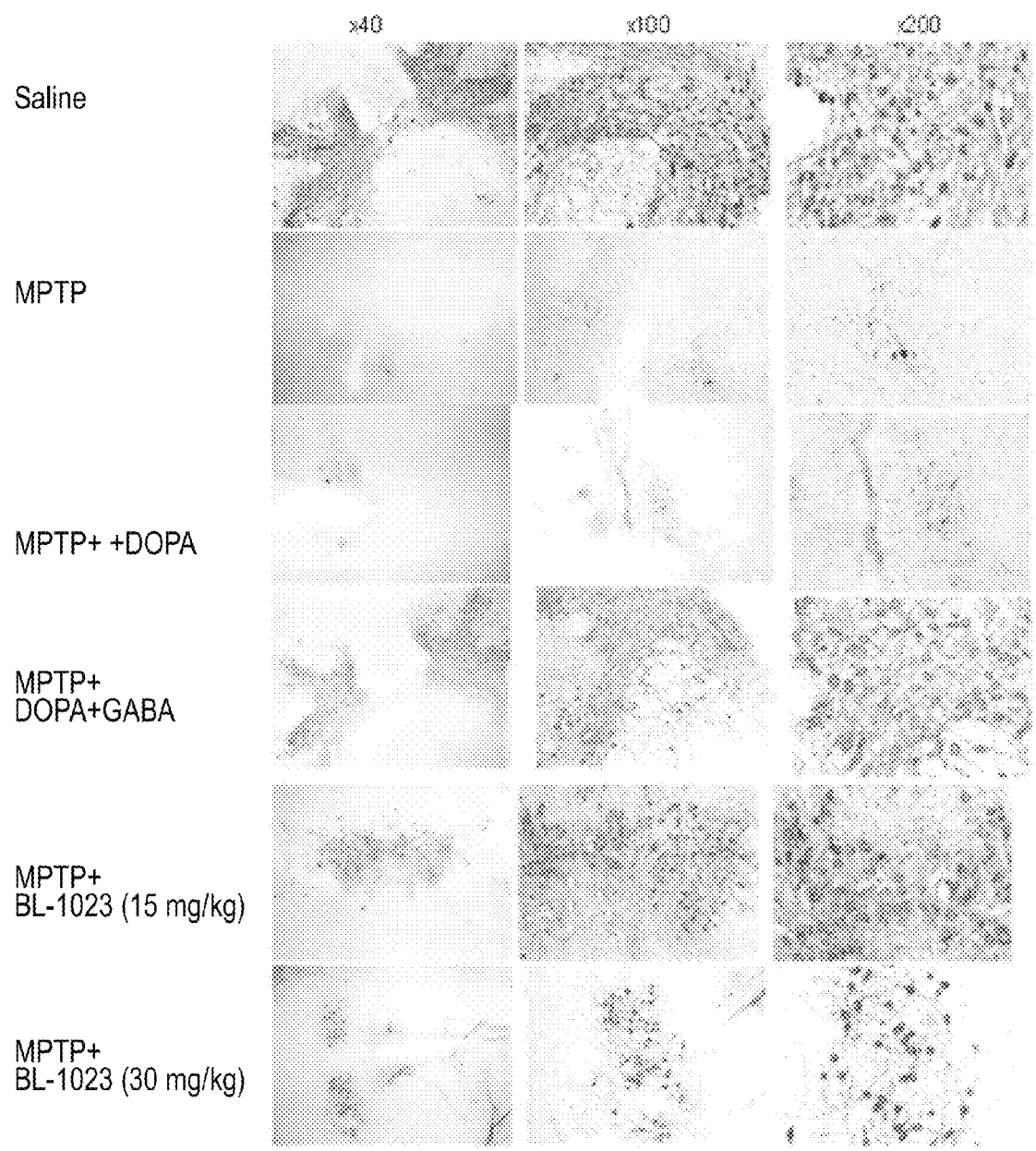

FIG. 16 presents electronic pictures of the Immunohystochemistry (IHC) horizontal sections from the substantia nigra of the mice treated as described in FIG. 15, at ×40, ×100 and ×200 magnification, using ImagePro software.

DESCRIPTION OF EMBODIMENTS OF THE INVENTION

The present invention, in some embodiments thereof, relates to novel compounds, to pharmaceutical compositions containing same and to uses thereof in the treatment of neurodegenerative diseases and disorders, such as Parkinson's disease.

The present invention, in some embodiments thereof, is of conjugates comprising L-DOPA covalently linked to at least one γ-aminobutyric acid (GABA) moiety, and of esters and acid addition salts of such conjugates. These conjugates are designed to have BBB permeability, and are capable to dissociate in the brain so as to release L-DOPA and GABA moieties. These conjugates therefore combine the beneficial therapeutic effects of L-DOPA and GABA in treating neurodegenerative diseases and disorders, while facilitating the BBB permeability of these agents, which is otherwise limited (as in the case of GABA) or non-selective (as in the case of L-DOPA).

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Neurodegenerative disorders, such as Parkinson's disease, are characterized by loss of neuronal functions. Presently, Levodopa, which is also referred to herein and in the art as L-DOPA (3,4-dihydroxy-L-phenylalanine), is the most effective commercially available drug for the treatment of the symptoms of Parkinson's. L-DOPA is used as a prodrug for increasing dopamine levels, since it is capable of crossing the blood-brain barrier whereas dopamine itself cannot. Once L-DOPA has entered the central nervous system (CNS), it is metabolized to dopamine by aromatic-L-amino-acid decarboxylase. However, conversion to dopamine also occurs in the peripheral tissues, thereby decreasing the available dopamine to the CNS.

While reducing the present invention to practice, the present inventors have devised and successfully practiced novel synthetic pathways for preparing various conjugates of L-DOPA and one or more GABA moieties. These synthetic pathways were designed such that regioselective coupling of one or more GABA moieties to L-DOPA is effected.

The present inventors have further surprisingly and unexpectedly uncovered that these conjugates were superior to L-DOPA, when administered per se, when tested in the well-known mice MPTP model for Parkinson's Disease (see, the Examples section that follows).

MPTP (1-methyl-4-phenyl-1,2,3,6-tetrahydropyridine) is an effective dopaminergic neurotoxin that causes permanent symptoms of Parkinson's disease in mice and is used to study the disease. As demonstrated in the Examples section that follows, L-DOPA-GABA conjugates according to embodiments of the invention were able to reduce MPTP related neurotoxicity. Specifically, in mice subjected to MPTP neurotoxicity according to a MPTP acute toxicity protocol (4 imp. injections on first day of the experiment), the neuronal density (measured using tyrosine hydroxylase immunostaining) in the substantia nigra of mice treated with Compound 5 (BL-1023), a conjugate according to some embodiments of the invention, was substantially higher than that in mice treated only with L-DOPA or non-treated mice (see, Table 4). Furthermore, in mice subjected to MPTP neurotoxicity according to a MPTP acute toxicity protocol, the protective effect of Compound 21 (AN-490), another conjugate according to some embodiments of the invention, against MPTP neurotoxicity could be deduced from the significant increase in motility, examined using the open field test (namely, the observed strong mobility, and decrease in immobility) of the mice treated with Compound 21 as compared to non-treated mice (see FIG. 2). The protective effect of Compound 21 was also observed by the enhanced neuronal density (measured using tyrosine hydroxylase immunostaining) in the substantia nigra of mice subjected to MPTP neurotoxicity (this time in a MPTP sub-acute protocol, i.e. mice receive one MPTP injection per day for five consecutive days), as compared to control non-treated mice (see, FIG. 8). The protective effect of Compound 16 (BL-1023*), another conjugate according to some embodiments of the invention, against MPTP neurotoxicity was also shown (in an acute toxicity protocol), with an improved level of performance of mice receiving Compound 16 treatment, in the RotaRod test, as compared to non-treated mice (see, FIG. 10). It was further shown that administration of Compound 16 to MPTP-treated mice was able to reverse the MPTP dependent reduction in neuronal density in the substantia nigra and stratium (see, FIGS. 13-16).

Thus, according to one aspect of embodiments of invention there is provided a chemical conjugate comprising L-DOPA covalently linked to at least one γ-aminobutyric acid (GABA).

The term "GABA" or "GABA moiety", as used herein, refers to a radical of the compound 4-amino-butyric acid (γ-aminobutyric acid). In the context of the present embodiments, GABA moiety is a 4-amino-butyryl moiety, or a —(C=O)—(CH$_2$)$_3$—NH$_2$ group, namely a moiety which is linked to a functional group of L-DOPA via its carbonyl carbon atom.

The amino group of a GABA moiety can be ionized at certain pH levels, depending on the conditions it is found in.

In some embodiments, L-DOPA (3,4-dihydroxy-L-phenylalanine) is covalently linked to one GABA moiety. In some embodiments, L-DOPA is covalently linked to two GABA moieties. In some embodiments, L-DOPA is covalently linked to three GABA moieties, and can also be covalently linked to four GABA moieties.

As used herein, the term "moiety" refers to a compound having a pharmacological activity. When described in the context of the conjugates presented herein, this term is understood to include a major portion of a molecule which is covalently linked to another molecule, preferably while maintaining the activity of the molecule.

In some embodiments, GABA is coupled to L-DOPA via a covalent bond or any other bond selected or designed capable of dissociating following crossing of the blood-brain barrier.

Thus, in some embodiments, the covalent bond linking L-DOPA and the at least one GABA moiety is selected or designed such that (i) it is not susceptible to dissociation (e.g., by enzymatic reactions) in the periphery and hence the conjugate remains substantially intact before crossing the BBB; and (ii) it is susceptible to dissociation in brain tissues (e.g., by brain derived enzymes), and hence the conjugate dissociates following crossing the BBB, thus releasing the biologically active L-DOPA and GABA.

A suitable bond can be, for example, a carboxylic ester bond, an oxyalkyl carboxylic ester bond or an amide bond, all of which can be dissociated by brain derived enzymes (e.g., brain derived esterases or amidases).

As used herein, a "carboxylic ester bond" describes an "—O—C(=O)—" bond.

As used herein, an "oxyalkyl carboxylic ester bond" describes an "O—R—O—C(=O)—" bond, where R is an alkylene, as defined hereinbelow.

An "amide bond" describes a "—NR'—C(=O)—" bond, where R' is hydrogen, alkyl, cycloalkyl or aryl, as defined hereinbelow.

As used herein, the term "alkyl" describes a saturated aliphatic hydrocarbon chain including straight chain and branched chain groups. Preferably, the alkyl group has 1 to 20 carbon atoms. Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl has 1 to 4 carbon atoms.

The term "alkylene" describes an alkyl group that is linked to two other groups. Thus, the term ethylene, for example, describes a —CH$_2$CH$_2$— group. The term "methylene" describes a —CH$_2$— group.

As used herein, the term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups include cyclopropane, cyclobutane, cyclopentane, cyclopentene, cyclohexane, cyclohexadiene, cycloheptane, cycloheptatriene and adamantane.

As used herein, the term "aryl" describes an all-carbon monocyclic or fused-ring polycyclic (i.e., rings which share adjacent pairs of carbon atoms) groups having a completely conjugated pi-electron system. Examples, without limitation, of aryl groups include phenyl, naphthalenyl and anthracenyl.

According to some embodiments of the present invention, the conjugate has the following structure:

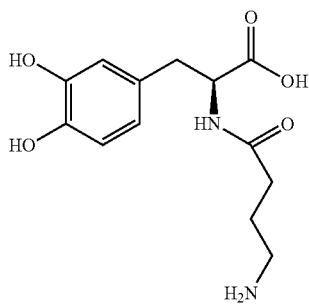

Chemical Formula: C$_{13}$H$_{18}$N$_2$O$_5$
Exact Mass: 282.12
Elemental Analysis: C, 55.31; H, 6.43; N, 9.92; O, 28.34

This conjugate is referred to herein, interchangeably, as Compound 5 or BL 1023.

The conjugates presented herein can be readily prepared by reacting GABA (optionally in a molar excess) with L-DOPA. The reaction can be performed in the presence of a base and optionally further in the presence of a dehydrating agent.

In some embodiments, prior to the reacting, the amine group of the GABA is protected by any of the conventional N-protecting groups (e.g., BOC). Thus, in some embodiments, prior to the reacting, GABA is converted to N-protected GABA. Similarly, in some embodiments, the carboxylic acid of L-DOPA is protected by converting it to an ester thereof, such as, for example, a methyl ester or a butyl ester.

The N-protected GABA and the optionally protected L-DOPA are then reacted in the presence of a base and optionally a dehydrating agent. In one example, the base is N-ethyldiisopropylamine and the dehydrating agent is carbonyl diimidazole (CDI). Optionally, the base is triethylamine (TEA). In some embodiments, the reaction is performed in the presence of a solvent, preferably an organic solvent such as, for example, dichloromethane.

Since GABA can react with various functional groups of L-DOPA (e.g., the α-amine group of L-DOPA, the para-hydroxyl group and the meta-hydroxyl group), typically a conjugate comprising two or more GABA moieties covalently linked to L-DOPA is obtained. As exemplified in the Examples section that follows, a mixture of geometrical isomers (regioisomers) of such a conjugate is typically obtained (see, Scheme 1 below).

In cases where a conjugate that comprises two or more GABA moieties covalently linked to L-DOPA is prepared, following the reacting, the protecting groups are removed, to thereby obtain the desired product.

In cases where a conjugate that comprises a single GABA moiety covalently linked to L-DOPA is prepared, removal of the other GABA moieties that are attached to L-DOPA can be performed. Such a removal is preferably effected under conditions that allow selective removal of GABA moieties, according to the desired final product.

In one example, removal of a GABA moiety is effected in the presence of a base (e.g., sodium hydroxide), preferably in an aqueous alcoholic environment, so as to obtain a conjugate in which a single N-protected GABA molecule is attached to the α-amine group of L-DOPA. Following removal of the N-protecting group an L-DOPA-GABA conjugate is obtained (see, Compound 5 in Scheme 1 hereinbelow).

In some embodiments, the functional groups of L-DOPA are protected, by means of protecting groups, such that the reaction with N-protected GABA is effected selectively, at the desired position. In these embodiments, the protecting groups and the order of their removal are selected so as to obtain the desired product, as exemplified in the Examples section that follows.

In some embodiments, when the GABA moiety is conjugated to the carboxylic acid functional group of L-DOPA, as detailed hereinbelow, all the functional groups of L-DOPA are first protected, via a certain order, so as to enable a selective reaction of GABA with the carboxylic acid moiety.

The final product and the intermediates can be purified by any technique well known in the art (e.g., column chromatography, crystallization), as exemplified in the Examples section that follows.

Using the above procedures, the conjugates described herein are typically obtained as HCl salts thereof. As demonstrated in the Examples section that follows, highly pure, stable, HCl salt of an L-DOPA-GABA conjugate can be obtained.

The HCl salts, however, can be converted, via reactions well-known in the art, to other acid addition salts of the conjugates, as detailed hereinbelow and is exemplified in the Examples section that follows.

Suitable processes of synthesizing Compound 5 (or BL-1023), including a scaled-up process, are described in details in Example 1 hereinbelow. Suitable processes for preparing other conjugates according to embodiments of the invention are also described in great detail in the Examples section the follows.

According to some embodiment of the present invention, L-DOPA is conjugated to more than one GABA moieties, and further according to other embodiments, the conjugates presented herein are L-DOPA ester derivatives, namely the carboxylic group in the L-DOPA moiety is an ester.

According to some embodiments, the conjugate presented herein is an L-DOPA butyl ester linked via an amide bond to a single GABA moiety, and having the structure presented below (also referred to herein, interchangeably, as Compound 16 or BL-1023*):

Compound 16

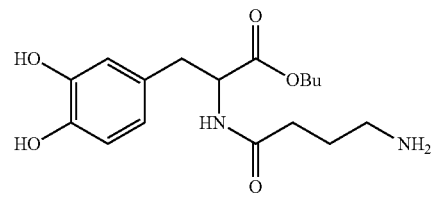

According to some embodiments, the conjugate presented herein is an L-DOPA butyl ester linked via the hydroxyls on the benzene to two GABA moieties, and having the structure presented below (also referred to herein, interchangeably, as Compound 21 or AN-490):

Compound 21

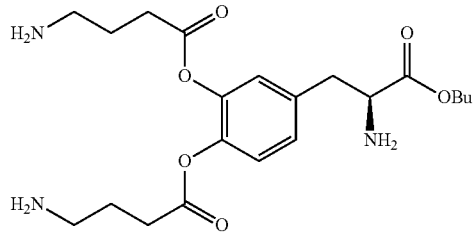

According to some embodiments, the conjugate presented herein is an L-DOPA butyl ester linked via one of the hydroxyls on the benzene to one GABA group, and having either of the structures presented below (also referred to herein as Compounds 21a and 21b):

Compound 21a

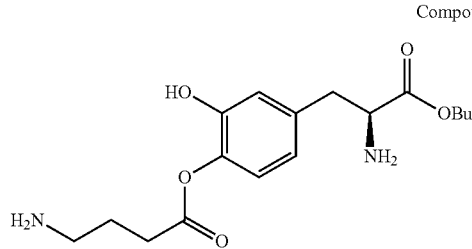

Compound 21b

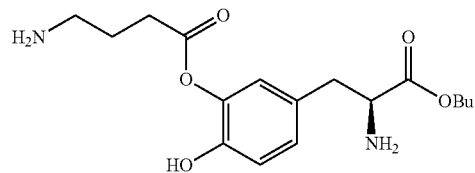

According to some embodiments of the invention, L-DOPA is conjugated to a GABA moiety, via the carboxylic group of L-DOPA, through an oxyalkylester linker.

The term "oxyalkylester" describes an alkylene, as defined herein, linked to a carboxylic ester moiety. This term, for example, encompasses a —$(CH_2)_m$-O—C(=O)— group, where m can be 1, 2, 3, 4, and up to 10. In some embodiments, the oxyalkylester linker is an oxymethyl carboxylic ester linker. Such a linker is susceptible to dissociation by brain-derived enzymes and is further highly advantageous by releasing, upon its dissociation, an additional metabolite—formaldehyde, which can also exhibit a beneficial pharmacological effect.

In some embodiments, when the oxyalkylester linker is oxymethylester, the conjugate has the following structure (also referred to herein as Compound 33):

Compound 33

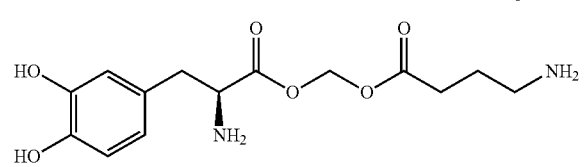

The conjugates presented herein can be collectively represented by the general formula I:

Formula I

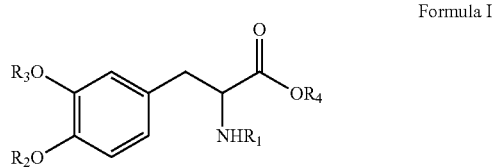

wherein:
$R_1$-$R_3$ are each independently selected from the group consisting of hydrogen, 4-amino-butyryl and butyryl; and
$R_4$ is selected from the group consisting of hydrogen, alkyl, butyryloxyalkyl and 4-amino butyryloxyalkyl,
such that at least one of $R_1$-$R_3$ is a 4-aminobutyryl and/or $R_4$ is 4-aminobutyryloxyalkyl.

Thus, at least one of $R_1$-$R_4$ represents a GABA moiety, as defined herein, formed by coupling GABA to L-DOPA.

According to some embodiments, only one of $R_1$-$R_4$ is a GABA moiety. According to some embodiments, $R_1$ is 4-amino-butyryl (GABA moiety) and $R_3$ and $R_2$ are each hydrogen. In these embodiments, the GABA moiety is coupled to the amine group of L-DOPA via an amide bond.

According to some embodiments, $R_2$ is 4-amino-butyryl (GABA moiety) and $R_1$ and $R_3$ are each hydrogen. In these embodiments, the GABA moiety is coupled to a hydroxyl group of L-DOPA via an ester bond.

According to some embodiments, $R_3$ is 4-amino-butyryl (GABA moiety) and $R_1$ and $R_2$ are each hydrogen. In these embodiments, the GABA moiety is also coupled to a hydroxyl group of L-DOPA via an ester bond.

According to some embodiments, the conjugate comprises more than one GABA moiety, and thus in some cases, the compound having the general formula I, $R_1$ and $R_2$ are each a GABA moiety and $R_3$ is hydrogen. In some cases, the compound is having the general formula I, $R_3$ and $R_2$ are each a GABA moiety and $R_1$ is hydrogen (for example, compound 21). As demonstrated in the Examples section that follows, such compounds are referred to as bis-GABA conjugates.

According to other embodiments, the compound includes three GABA moieties, and thus three of $R_1$-$R_4$ in formula I is a 4-amino-butyryl group (GABA moiety).

In some embodiments, each of $R_1$-$R_3$ is a 4-amino-butyryl group (GABA moiety).

In some embodiments, the carboxylic acid group in the L-DOPA moiety is in its free acid form, namely a —(C=O)OH form, and thus $R_4$ in formula I is hydrogen.

According to other embodiments, the L-DOPA moiety is in its ester form, and thus $R_4$ is an alkyl, such as, but not limited to, methyl, ethyl, propyl, butyl and octyl. In some embodiments, $R_4$ is methyl and in other embodiments, $R_4$ is butyl.

As demonstrated in the Examples section that follows, the free acid form, as well as the methyl and butyl ester forms, of various conjugates according to embodiments of the invention, have been prepared.

Exemplary such conjugates include Compounds 16, 21, 21a and 21b.

According to embodiments of the invention, exemplary L-DOPA-GABA conjugates include compounds encompassed by general Formula I, wherein:

$R_1$ is 4-amino-butyryl (GABA moiety), $R_3$ and $R_2$ are each hydrogen, and $R_4$ is hydrogen, methyl or butyl (for example, Compound 5 (BL-1023) and Compound 16 (BL-1023*));

$R_2$ is 4-amino-butyryl (GABA moiety), $R_1$ and $R_3$ are each hydrogen, and $R_4$ is hydrogen, methyl or butyl (for example, Compound 21b);

$R_3$ is 4-amino-butyryl (GABA moiety), $R_1$ and $R_2$ are each hydrogen, and $R_4$ is hydrogen, methyl or butyl (for example, Compounds 21a);

$R_1$ and $R_2$ are each 4-amino-butyryl (GABA moiety), $R_3$ is hydrogen, and $R_4$ is hydrogen, methyl or butyl;

$R_1$ and $R_3$ are each 4-amino-butyryl (GABA moiety), $R_2$ is hydrogen, and $R_4$ is hydrogen, methyl or butyl;

$R_2$ and $R_3$ are each 4-amino-butyryl (GABA moiety), $R_1$ is hydrogen, and $R_4$ is hydrogen, methyl or butyl (e.g., Compound 21 (AN-490)); and each of $R_1$-$R_3$ is 4-amino-butyryl (GABA), and $R_4$ is hydrogen, methyl or butyl.

As further demonstrated in the Examples section that follows, a conjugate in which the L-DOPA is linked via its carboxylic group to a butyryloxyalkyl moiety has also been prepared (see, for example, Compound 33).

A butyryloxyalkyl moiety represents, for example, —(CH$_2$)m-O—C(=O)-butyl, which is linked to the carboxylate (—C(=O)—O—) group derived from the carboxylic acid group of L-DOPA. Accordingly, a 4-aminobutyryloxymethyl group represents —CH$_2$—O—C(=O)—(CH$_2$)$_3$—NH$_2$.

The advantageous pharmacological features of such a conjugate are delineated hereinabove.

In addition, while, as described in detail in the Examples section that follows, coupling a GABA moiety selectively to either or both hydroxyl groups of L-DOPA and/or to the amine group of L-DOPA requires synthetic and purification manipulations that may affect the overall synthesis yield, coupling a GABA moiety to the carboxylic acid group of L-DOPA is performed selectively without excessive manipulations.

Using this form of linking GABA to the carboxylic acid moiety of L-DOPA, conjugates in which $R_4$ is a GABA moiety are prepared.

Thus, according to embodiments of the invention, the conjugate has the general formula I hereinabove, in which $R_4$ is a butyryloxyalkyl, and each of $R_1$-$R_3$ is hydrogen.

According to further embodiments, $R_4$ is a butyryloxyalkyl, and at least one of $R_1$-$R_3$ is 4-aminobutyryl.

According to further embodiments, $R_4$ is a butyryloxyalkyl, and at least two of $R_1$-$R_3$ is 4-aminobutyryl.

According to further embodiments, $R_4$ is a butyryloxyalkyl, and each of $R_1$-$R_3$ is 4-aminobutyryl, such that the conjugate comprises 4 GABA moieties linked to L-DOPA.

According to some embodiments, the conjugates presented herein and represented by compounds having the general formula I are is an acid addition salt form thereof.

As is well known in the art, the phrase "acid addition salt" describes a complex of two ionizable moieties, a base and an acid, which, when interacted in a particular stoichiometric proportion and under suitable conditions, form a salt that comprises one or more cations of the base moiety and one or more anions of the acid moiety. As used herein, the phrase "acid addition salt" refers to such a complex, in which the base moiety is an amine, such that the salt comprises a cationic form of the amine (ammonium) and an anionic form of an acid.

The amine group can be derived from the GABA moiety or moieties linked to L-DOPA, or from the amine moiety of L-DOPA, if present in a non-conjugated form thereof.

Depending on the stoichiometric proportions between the base and the acid in the salt complex, as is detailed hereinbelow, the acid additions salts can be either mono addition salts or poly addition salts.

The phrase "mono addition salt", as used herein, refers to a salt complex in which the stoichiometric ratio between the acid anion and amine cation is 1:1, such that the acid addition salt includes one molar equivalent of the acid per one molar equivalent of the conjugate.

The phrase "poly addition salt", as used herein, refers to a salt complex in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the conjugate.

The stoichiometric proportions between the base and the acid of the salt complex, according to some embodiments of the present invention, ranges from 6:1 to 1:6 base:acid equivalents, from 4:1 to 1:4 base:acid equivalents, from 3:1 to 1:3 base:acid equivalents or from 1:1 to 1:3 base:acid equivalents.

The acid addition salts of a chemical conjugate according to the present invention are therefore complexes formed between one or more amino groups of the compound and one or more equivalents of an acid. The acid addition salts may therefore include a variety of organic and inorganic acids, such as, but not limited to, hydrochloric acid which affords an hydrochloric acid addition salt, acetic acid which affords an acetic acid addition salt, ascorbic acid which affords an ascorbic acid addition salt, benzenesulfonic acid which affords a benzenesulfonic acid addition salt, camphorsulfonic acid which affords a camphorsulfonic acid addition salt, toluenesulfonic acid which affords a toluenesulfonic acid addition salt, trifluoroacetic acid which affords a trifluoroacetic acid addition salt, citric acid which affords a citric acid addition salt, maleic acid which affords a maleic acid addition salt, methanesulfonic acid which affords a methanesulfonic acid (mesylate) addition salt, naphthalenesulfonic acid which affords a napsylate addition salt, oxalic acid which affords an oxalic acid addition salt, phosphoric acid which affords a phosphoric acid addition salt, succinic acid which affords a succinic acid addition salt, sulfuric acid which affords a sulfuric acid addition salt and tartaric acid which affords a tartaric acid addition salt. Each of these acid addition salts can be either a mono acid addition slat or a poly acid addition salt, as these terms are defined hereinabove.

Any other pharmaceutically acceptable salts, solvates or hydrates of the conjugates described herein, as well as processes of preparing these pharmaceutically acceptable salts, solvates and hydrates, are also encompassed by embodiments of the invention.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The term "solvate" refers to a complex of variable stoichiometry (e.g., di-, tri-, tetra-, penta-, hexa-, and so on), which is formed by a solute (the hybrid compound) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Embodiments of the invention further encompass various crystalline forms (polymorphs) of the conjugates described herein, as well as processes of preparing these crystalline forms.

Embodiments of the invention further encompass all isomeric forms, stereoisomeric forms (including enantiomers and diastereomers) and racemic mixtures of the conjugates described herein.

The conjugates presented herein, by being capable of effectively crossing the BBB and releasing free dopamine and free GABA in the brain tissue, can be beneficially used in various therapeutic applications in which elevated levels of dopamine and GABA in the brain are desired. These include, for example, treating or preventing a neurodegenerative disease or disorder.

Hence, according to an additional aspect of embodiments of the invention, the conjugate described herein can be used as a medicament, whereby the medicament can be utilized in treating or preventing a neurodegenerative disease or disorder.

According to an additional aspect of embodiments of the invention there is provided a method of treating a neurodegenerative disease or disorder. The method, according to these embodiments, is effected by administering to a subject in need thereof a therapeutically effective amount of the conjugate as presented herein.

The term "treating" used herein refers to refers to reversing, alleviating, inhibiting the progress of, or preventing the disorder, disease or condition to which such term applies, or one or more symptoms of such disorder or condition. The term "treatment" or "therapy" as used herein refer to the act of treating.

The phrase "neurodegenerative disease or disorder" as used herein refers to any disease, disorder or condition of the nervous system (e.g., the central nervous system, CNS) which is characterized by gradual and progressive loss of neural tissue, neurotransmitter, or neural functions. Examples of neurodegenerative disorder include, Parkinson's disease, multiple sclerosis, amyatrophic lateral sclerosis, autoimmune encephalomyelitis, Alzheimer's disease and Huntington's disease.

According to some embodiments the neurodegenerative disease is Parkinson's disease.

The conjugates described herein can be administered by any acceptable route of administration.

In some embodiments, the conjugate is administered parenterally (e.g., subcutaneously or intraperitoneally) or orally.

The term "subject" as used herein refers to a mammal having a blood brain barrier, such as a human being.

The term "therapeutically effective amount" as used herein refers to that amount of the conjugate being administered which is capable of relieving to some extent one or more of the symptoms of the neurodegenerative disease or disorder being treated.

A therapeutically effective amount according to some embodiments of the invention ranges between 0.01 and 200 mg/kg body, between 0.1 and 100 mg/kg body, between 0.5 and 50 mg/kg body, or between 1 and 20 mg/kg body.

In each of the methods and used described herein, the conjugates presented herein can be utilized in combination with an additional active agent.

In some embodiments, the additional active agent is a CNS-acting agent.

As used herein, the phrase "CNS-acting agent" encompasses any compound which is capable of exerting a CNS activity.

The phrase "CNS activity" as used herein describes a pharmacological activity exerted in the CNS, which is aimed at treating a CNS-associated impairment. Such a pharmacological activity typically includes modulation of neuronal signals transduction.

According to one embodiment, the CNS-acting agent is a psychotropic drug.

Psychotropic drugs are known in the art, and are referred to herein, as pharmacological agents that exert activity in the CNS to thereby treat a CNS-associated disease or disorder.

Psychotropic drugs include, but are not limited to, antipsychotic drugs (typical and atypical), anxiolytic drugs, antidepressants, anti-convulsive drugs (also referred to herein and is the art and anti-convulsants), anti-parkinsonian drugs, acetylcholine esterase inhibitors, MAO inhibitors, selective serotonin reuptake inhibitors (SSRIs) and selective noradrenalin receptor inhibitors (SNRIs).

Representative examples of psychotropic drugs that can be utilized in combination with the conjugates of the present embodiments include, without limitation, chlorpromazine, perphenazine, fluphenazine, zuclopenthixol, a thiopropazate, haloperidol, benperidol, bromperidol, droperidol, spiperone, pimozide, piperacetazine, amilsulpride, sulpiride, clothiapine, ziprasidone, remoxipride, sultopride, alizapride, nemonapride, clozapine, olanzapine, ziprasidone, sertindole, quetiapine, fluoxetine, fluvoxamine, desipramine, paroxetine, sertraline, valproic acid, temazepam, flutemazepam, doxefazepam, oxazepam, lorazepam, lormetazepam, cinolazepam, flutazolam, lopirazepam, meprobamate, carisoprodol, acetophenazine, carphenazine, dixyrazine, priciazine, pipothiazine, homophenazine, perimetazine, perthipentyl, flupentixol, piflutixol, teflutixol, oxypethepin, trifluperidol, penfluridol, meclobemide, norclomipramine, amoxapine, nortriptyline, protriptyline, reboxetine, tacrine, rasagiline, amantidine, duloxetine, phenobarbital, phenytoin, a drug of the phenothiazines family, a drug of the benzodiazepines family and butyrophenone.

The conjugates presented herein can be utilized in any of the uses and methods described herein either per se or as part (as an active ingredient) of a pharmaceutical composition.

As used herein a "pharmaceutical composition" refers to a preparation that comprises the conjugate as described herein and other chemical components such as physiologically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences", Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the conjugates presented herein may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the conjugates presented herein can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the conjugate may take the form of tablets or lozenges formulated in conventional manner.

For administration by inhalation, the compositions for use according to embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions.

Alternatively, the active ingredient may be in powder form for constitution with a suitable vehicle, e.g., sterile, pyrogen-free water, before use.

The conjugates presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of embodiments of the invention include the active ingredients contained in an amount effective to achieve the intended purpose. More specifically, a therapeutically effective amount means an amount of conjugate effective to prevent, alleviate or ameliorate symptoms of a neurodegenerative disease or disorder.

Determination of a therapeutically effective amount is well within the capability of those skilled in the art, especially in light of the detailed disclosure provided herein.

For the conjugate used in the methods of the invention, the therapeutically effective amount or dose can be estimated initially from activity assays in cell cultures and/or animals. For example, a dose can be formulated in animal models to achieve a circulating concentration range that includes the IC50 as determined by activity assays (e.g., the concentration of the test compound, which achieves a half-maximal activity in the dopamine and GABA systems). Such information can be used to more accurately determine useful doses in humans.

Toxicity and therapeutic efficacy of the conjugate described herein can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active ingredients which are sufficient to maintain clinically beneficial effects, termed the minimal effective concentration (MEC). Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a controlled released formulation.

The phrase "controlled release" as used herein refers to a formulation capable of releasing the active ingredient at a predetermined rate such that therapeutically beneficial levels are kept over an extended period of time. Suitable controlled release formulations are well known in the art (e.g., "Remington's Pharmaceutical Sciences," Philadelphia College of Pharmacy and Science, 19th Edition, 1995).

The amount of a pharmaceutical composition to be administered will, of course, be dependent on the subject being treated, the severity of the affliction, the manner of administration, the judgment of the prescribing physician, etc.

The pharmaceutical composition of the present invention may, if desired, be presented in a pack or dispenser device, such as a FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Pharmaceutical compositions comprising the conjugate presented, optionally in combination with an additional active agent, formulated in a compatible pharmaceutical carrier may also be prepared, placed in an appropriate container, and labeled for treatment of an indicated condition, as set forth hereinabove.

Thus, according to an embodiment of this aspect of the present invention, the pharmaceutical composition is packaged in a packaging material and identified in print, in or on the packaging material, for use in the treatment of a neurodegenerative disease or disorder as described herein.

According to some embodiments, the pharmaceutical composition is packaged in a packaging material and identified in print, in or on the packaging material, for use in the treatment of a Parkinson's disease.

Such a packaged pharmaceutical composition is also referred to herein interchangeably as an article-of-manufacturing or a pharmaceutical kit.

Hence, the invention provides novel conjugates, pharmaceutical compositions, articles-of-manufacturing and methods of use thereof for treating neurodegenerative disorders safely and effectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Chemical Syntheses of L-DOPA-GABA Conjugates

Materials and Methods:
$^1$H and $^{13}$C-NMR spectra were obtained on Bruker AC-200, DPX-300 and DMX-600 spectrometers. Chemical shifts are expressed in ppm downfield from Me$_4$Si (TMS) used as internal standard. The values are given in δ scale.

HRMS/LRMS were obtained on an AutoSpec Premier (Waters UK) spectrometer in CI (=Chemical Ionization), CH$_4$.

Progress of the reactions was monitored by TLC on silica gel (Merck, Art. 5554).

Flash chromatography was carried out on silica gel (Merck, Art. 9385). Compounds with nitrogen were colored by ninhydrin.

Melting points were determined on a Fisher-Johns apparatus and were uncorrected.

HPLC measurements were conducted using C-128 (internal number) Phenomenex Nucleosil C18 column, 5 μm, 250× 4.6 mm, 120 A. An exemplary mobile phase included A: 0.1% TFA in H$_2$O, B: CH$_3$CN, and analysis was conducted using the following gradient: 0 to 4 minutes, 0% of B; 10 minutes, 30% of B; 11 minutes, 30% of B; 12 minutes, 0% of B; 14 minutes, 0% of B. Flow rate: 1 ml/ml. Product was dissolved in water (1 mg/ml). UV detector was operated at 282 nm. Running time: 22 minutes. Temperature: 5° C.

IR measurements were conducted using Bio-Rad FTS 3000MX spectrophotometer, for KBr pellets containing the tested compound.

Commercially available compounds were used without further purification.

Water content measurements were performed using Coulometric Karl-Fischer with Metrohm Thermoprep 832 and Metrohm Coulometer 831 according to USP <921> method 1c.

The nomenclature of the compounds was given according to ChemDraw Ultra v. 11.0.1 (CambridgeSoft). The numbering on the chemical structures is for spectral analysis only.

The following compounds were prepared according to known procedures: chloromethyl chlorosulfate [Binderup et al. *Synth. Commun.* 1984, 14, 857-864], N-Boc-GABA [Bodanszky et al. Principles of Peptide Synthesis. In Springer-Verlag, New York: 1984; p 99] and N-Cbz-GABA [Lever Jr, O. W. and Vestal, B. R. *J. Heterocycl. Chem.* 1986, 23, 901-904].

Preparation of Mono-GABA-L-DOPA Conjugate (Compound 5, BL-1023; Having a GABA Moiety Linked to L-DOPA via an Amide Bond)

Synthetic Route 1:

The L-DOPA-GABA conjugate (BL-1023) is prepared by reacting L-DOPA and GABA and isolating the obtained conjugate. According to some embodiments presented herein, the amine group of the GABA is protected prior to the conjugation reaction. Since L-DOPA includes a few functional groups that can react with the functional carboxylic acid group of GABA, typically, a conjugate that includes L-DOPA and at least two GABA molecules is obtained, requiring an additional step of removing a GABA molecule selectively so as to obtain the desired product. Thereafter, removal of the amine-protecting group in the GABA moiety is effected.

As detailed hereinbelow, using this pathway, the L-DOPA-GABA conjugate having a single GABA moiety (mono-GABA-L-DOPA conjugate) was successfully obtained in high yield and purity, upon carefully selecting the reaction conditions. The synthetic pathway for preparing L-DOPA-GABA conjugate (Compound 5, BL-1023) is illustrated in Scheme 1 below.

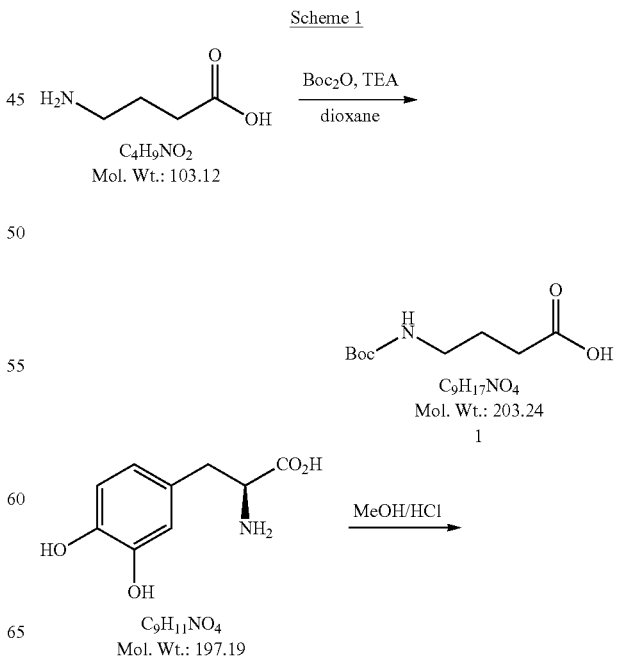

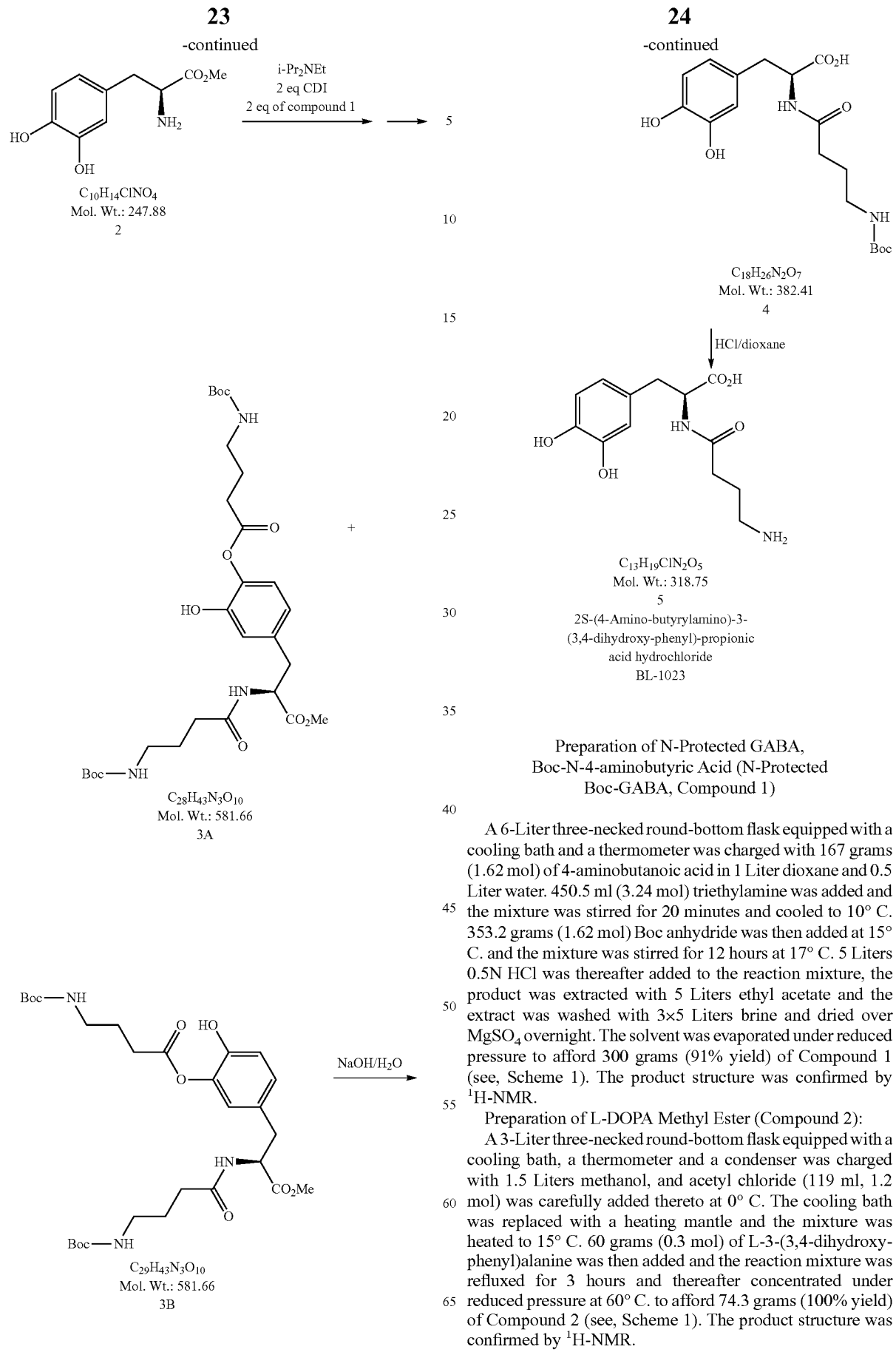

Preparation of N-Protected GABA, Boc-N-4-aminobutyric Acid (N-Protected Boc-GABA, Compound 1)

A 6-Liter three-necked round-bottom flask equipped with a cooling bath and a thermometer was charged with 167 grams (1.62 mol) of 4-aminobutanoic acid in 1 Liter dioxane and 0.5 Liter water. 450.5 ml (3.24 mol) triethylamine was added and the mixture was stirred for 20 minutes and cooled to 10° C. 353.2 grams (1.62 mol) Boc anhydride was then added at 15° C. and the mixture was stirred for 12 hours at 17° C. 5 Liters 0.5N HCl was thereafter added to the reaction mixture, the product was extracted with 5 Liters ethyl acetate and the extract was washed with 3×5 Liters brine and dried over $MgSO_4$ overnight. The solvent was evaporated under reduced pressure to afford 300 grams (91% yield) of Compound 1 (see, Scheme 1). The product structure was confirmed by $^1$H-NMR.

Preparation of L-DOPA Methyl Ester (Compound 2):

A 3-Liter three-necked round-bottom flask equipped with a cooling bath, a thermometer and a condenser was charged with 1.5 Liters methanol, and acetyl chloride (119 ml, 1.2 mol) was carefully added thereto at 0° C. The cooling bath was replaced with a heating mantle and the mixture was heated to 15° C. 60 grams (0.3 mol) of L-3-(3,4-dihydroxyphenyl)alanine was then added and the reaction mixture was refluxed for 3 hours and thereafter concentrated under reduced pressure at 60° C. to afford 74.3 grams (100% yield) of Compound 2 (see, Scheme 1). The product structure was confirmed by $^1$H-NMR.

Preparation of di-GABA-L-DOPA Conjugates (Compounds 3A and 3B):

A 4-Liter round-bottom flask equipped with a nitrogen inlet, motor stirrer, additional funnel and thermometer was charged with 114.8 grams (0.56 mol) Compound 1 in 2 Liters dichloromethane (DCM) and 90 grams carbonyl diimidazole (CDI, 0.56 mol) were added portion wise thereto at 17° C. with stirring. The mixture was stirred for 3 hours and 70 grams (0.28 mol) of Compound 2, followed by 48.4 grams N-ethyldiisopropylamine (0.28 mol) were added. The reaction mixture was stirred for 24 hours at 17° C., washed in a separation funnel with 2×1.5 Liters 0.1N HCl and 3×1 Liter water and the organic phase was dried over $MgSO_4$ overnight. The solvent was remover under reduced pressure and the residue was purified by column chromatography using a silica gel column and a 1:2 mixture of ethyl acetate:hexane mixture as eluent to afford 120 grams (73% yield) of a mixture of Compounds 3A and 3B (see, Scheme 1). The presence of a mixture of these two isomers was confirmed by $^1$H-NMR.

Preparation of Boc-N-GABA-L-DOPA Conjugate (Compound 4):

A 3-Liter three-necked round-bottom flask equipped with a nitrogen inlet, a thermometer and a heating mantle was charged with 120 grams (0.2 mol) of a mixture of Compounds 3A and 3B dissolved in 500 ml methanol. 24 grams NaOH (0.6 mol) were then added and the reaction mixture was heated at 60° C. for 1 hour. The reaction mixture was then concentrated under reduced pressure, 650 ml 1N HCl were added at 5° C. and the product was extracted with ethyl acetate. The extract was washed with brine, dried over $MgSO_4$ overnight and the solvent was remover under reduced pressure. The residue was purified by column chromatography (so as remove traces of Compound 1) using a silica gel column, under argon atmosphere, and a 1:2 mixture of 0-5% methanol in DCM as eluent, to afford 25 grams (32% yield) of Compound 4 (see, Scheme 1). The product structure was confirmed by $^1$H-NMR.

Preparation of L-DOPA-GABA Conjugate (Compound 5, BL-1023):

A 500 ml three-necked round-bottom flask equipped with a nitrogen inlet, a thermometer and a cooling bath was charged with 25 grams (0.065 mol) of Compound 4 dissolved in 200 ml ethyl acetate. The solution was cooled to 0° C. and 49 ml (0.196 mol) 4N HCl in dioxane were added thereto and mixture was stirred at 17° C. for 24 hours. The solid product was filtered and washed with 4×200 ml ethyl acetate and dried at 60° C., 10 mmHg, for 9 hours to afford 15 grams (72%) of Compound 5 (see Scheme 1 and Compound I hereinabove). The product structure was confirmed by $^1$H-NMR but significant amounts of dioxane and ethyl acetate were observed.

Removal of the solvents was performed by dissolving 37 grams of Compound 5 (obtained in 3 batches according to the procedure described hereinabove) in 150 ml isopropanol (IPA) and pouring the solution to 3 Liters diethyl ether while vigorously stirring the resulting mixture. The solid product was filtered, washed thoroughly with 3×200 ml ether and dried at 100° C., 10 mmHg, for 60 hours to afford Compound 5 as a brown powder. $^1$H-NMR indicated the presence of 0.2% ether.

Purity of the product was determined by HPLC to be 99.5%.

Water content was determined by Karl-Fisher analysis to be 0.41%.

Elemental analysis: C:47.67%; H:6.24%; N:8.55%.

Chloride analysis: 9.62%.

GC-MS analysis showed data consistent with molecular mass (283.8 for M-HCl).

$^{13}$C-NMR: δ=22.55, 31.82, 38.43, 53.81, 116.1 (d), 121.28, 128.97, 142.85 (d), 174.39 (d) ppm.

Synthetic Route 2 (Up-Scaled):

The following presents an improved, scaled-up synthesis protocol for obtaining Compound 5, as schematically described in Scheme 2 below.

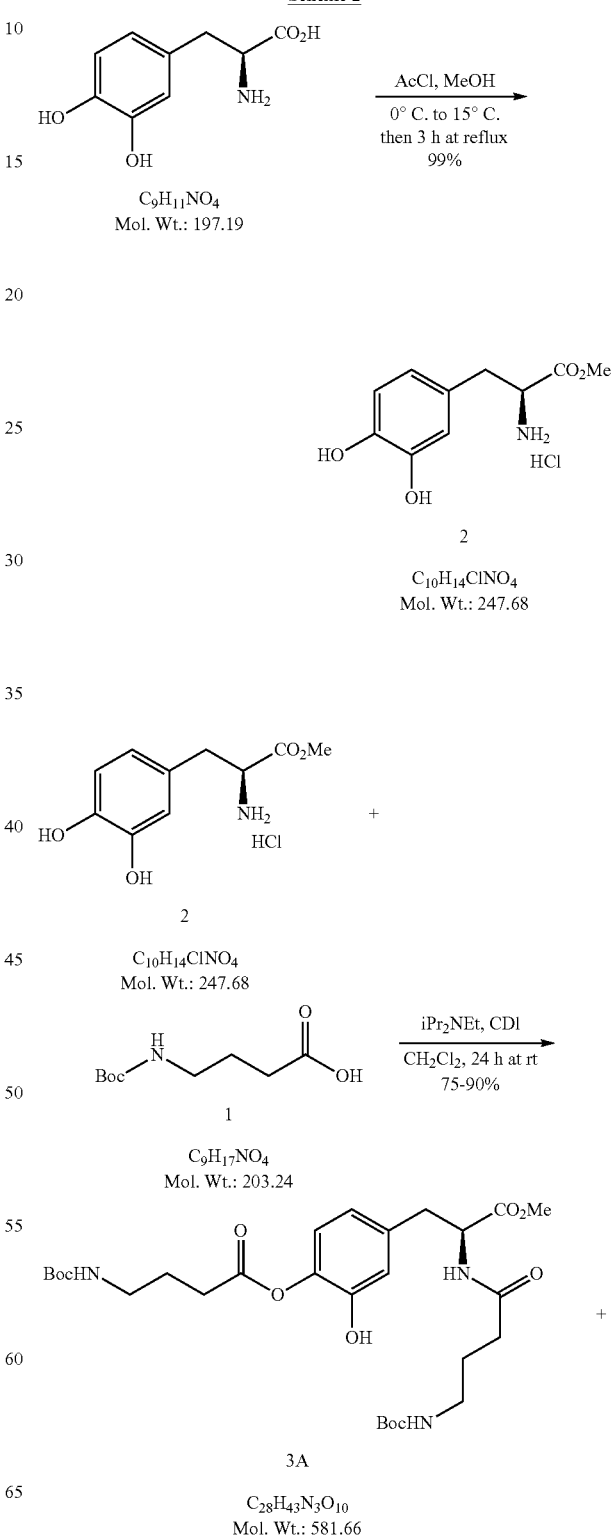

Scheme 2

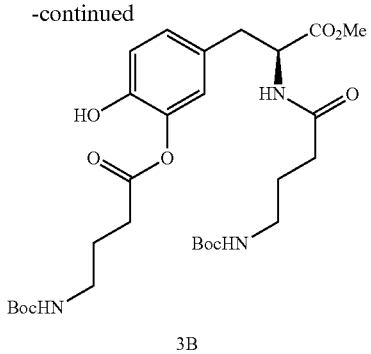

3B

C$_{28}$H$_{43}$N$_3$O$_{10}$
Mol. Wt.: 581.66

Scheme 2

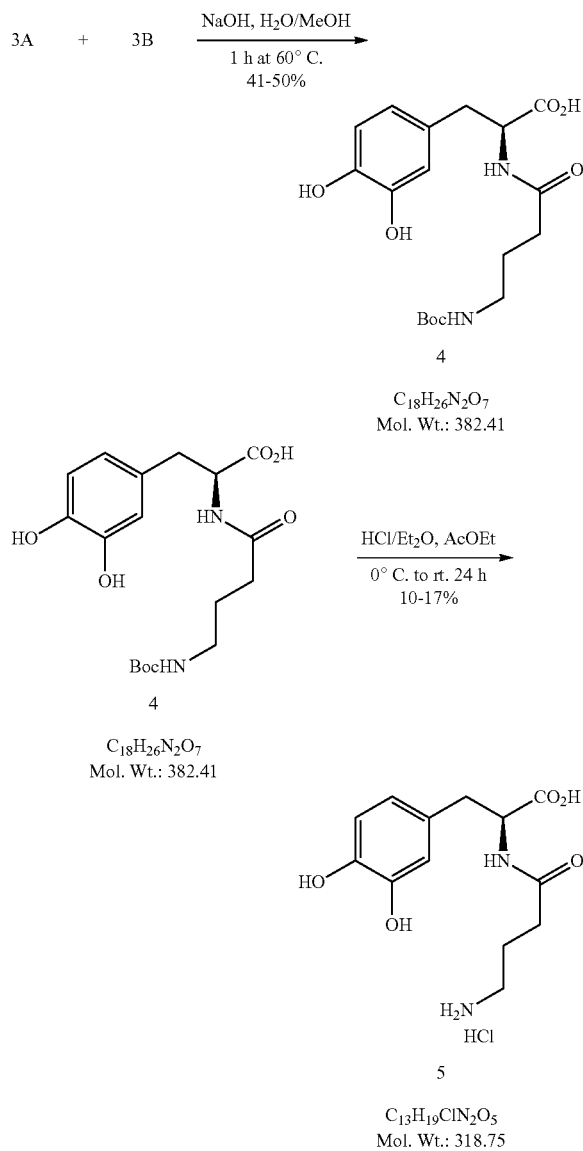

Preparation of L-DOPA methyl ester (Compound 2): A 5-Liter three-necked round-bottom flask equipped with a cooling bath, a thermometer and a condenser was charged with methanol (2.5 Liters). Acetyl chloride (2.03 mol, 4 equivalents) was added carefully at 0° C., the reaction mixture was thereafter cooled to room temperature (15° C.) and L-DOPA (0.507 mol, 1 equivalent) was added. The reaction mixture was refluxed (65° C.) for 3 hours and then concentrated under vacuum to afford 126.6 grams of compound 2 as a white solid (99% yield).

$^1$NMR (400 MHz, DMSO-d): δ=2.95 (m, 2H, H-2), 3.69 (s, 3H, OMe), 4.13 (s, 1H, H-1), 6.45 (dd, J=1.9 Hz, J'=8 Hz, 1H, Arom. H), 6.59 (d, J=1.9 Hz, 1H, Arom. H), 6.68 (d, J=8 Hz, Arom. H), 8.51 (s, 3H, NH3+), 8.87 (br, 2H, OH).

Preparation of di-GABA-L-DOPA Conjugates (Compounds 3A and 3B):

Compounds 3A and 3B were obtained by reacting methylated L-DOPA salt (Compound 2) and Boc-protected GABA (Compound 1). A 3-Liter three-necked round-bottom flask, equipped with a thermometer and being under argon atmosphere, was charged with Boc-protected GABA (0.848 mol, 2 equivalents) and dichloromethane (1.5 Liter).

Carbonyldiimidazole (CDI) (0.848 mol, 2 equivalents) was added portion wise at room temperature (17° C.) with stirring, and the reaction mixture was stirred at room temperature for 3 hours. Then, Compound 2 (0.424 mol, 1 equivalent) and N-ethyldiisopropylamine (0.432 mol, 1.02 equivalent) were added, and the reaction mixture was stirred for 24 hours at room temperature. The reaction mixture was thereafter washed with a 0.1 M HCl solution (2×1 Liter) (in a separation funnel) and with water (3×500 ml). The organic phase was dried over MgSO4 overnight, filtered and evaporated to afford 225.6 grams of a mixture of Compounds 3A and 3B as a slightly yellow foam (91% yield).

$^1$H NMR spectra confirmed the presence of a mixture of the two regioisomers Compounds 3A and 3B and of residual Boc-protected GABA (Compound 1).

Preparation of Boc-N-GABA-L-DOPA Conjugate (Compound 4):

This step involves deprotection of the methyl ester and of the phenol protecting groups. A 2-Liter three-necked round-bottom flask equipped with a thermometer, under argon atmosphere, was charged with a mixture Compounds 3A and 3B (0.388 mol, 1 equivalent), obtained as described hereinabove, in methanol (990 ml). A solution of NaOH (1.16 mol, 3 equivalents) in water (1.2 Liter) was then added and the reaction mixture was heated at 60° C. for 1 hour. The reaction mixture was thereafter concentrated in vacuum and HCl 1M (1.2 Liter) was added at 5° C. The aqueous phase was extracted with ethyl acetate (2×800 ml), the organic layers were combined and washed with saturated NaCl (2×700 ml), dried overnight over MgSO$_4$, filtered and concentrated, to give a mixture of the desired Compound 4 (approximately 180 grams) and of Boc-protected GABA.

Compound 4 was purified by re-crystallization or precipitation. In an exemplary purification procedure, the mixture of Compound 4 and Boc-protected GABA was dissolved in ethyl acetate (200 ml) and the obtained solution was added slowly to cold dichloromethane (2 Liters) under stirring. The desired product precipitated and the solution was decanted. Upon 3-5 repetitive precipitations, Pure Compound 4 (70.44 grams) was obtained as a slightly brown foam (47% yield).

$^1$H NMR (400 MHz, DMSO-d): δ=1.37 (s, 9H, H-Boc), 1.52 (m, 2H, CH2), 2.05 (m, 2H, CH2), 2.75 (m, 4H, CH2), 4.29 (m, 1H, H-2), 6.45 (dd, J=1.8 Hz and J'=8 Hz, 1H, Arom. H), 6.60 (d, J=8 Hz, 2H, Arom. H), 6.77 (t, J=4.9 Hz, 1H, NHBoc), 8.03 (d, J=8 Hz, 1H, NH), 8.70 (dbr, 2H, OH), 12.60 (br, 1H, CO2H).

Preparation of L-DOPA-GABA Conjugate (Compound 5, BL-1023):

The final step of the synthesis involves deprotection of the amino function and the formation of the BL-1023 hydrochloric salt. A 3-Liter three-necked round-bottom flask equipped with a thermometer, under argon atmosphere, was charged with Compound 4 (0.184 mol, 1 equivalent) in ethyl acetate (950 ml). The solution was cooled to 0° C. and HCl 2M in diethyl ether (0.553 mol, 3 equivalents) was added. The reaction mixture was stirred at room temperature for 36 hours. The resulting precipitate was filtered and washed with ethyl acetate (3×200 ml). The product was thereafter dissolved in isopropanol (250 ml) and the solution was added slowly to diethyl ether (4 Liters) under vigorous stirring. The obtained precipitate was filtered under inert atmosphere (Argon) and dried under vacuum, to afford the desired Compound 5 (BL-1023) (slightly beige solid). After several days under vacuum the compound was still not dry (36 grams) and contained isopropanol, diethyl ether, ethyl acetate and water.

$^1$H NMR (400 MHz, DMSO-d): δ=1.74 (m, 2H, CH2), 2.20 (m, 2H, CH2), 2.86 (m, 4H, $CH_2$), 4.29 (m, 1H, H-2), 6.47 (dd, J=1.8 Hz and J'=8 Hz, 1H, Arom. H), 6.64 (d, J=8 Hz, 2H, Arom. H), 7.99 (br, 3H, $NH_3^+$), 8.20 (d, J=7.9 Hz, 1H, NH), 8.77 (br, 2H, OH), 12.65 (br, 1H, $CO_2H$).

The NMR spectrum showed also some small impurities at 1.05-1.15 ppm, 4.8 ppm and 8.3 ppm in all three batches, thus indicating that re-crystallization should be performed.

HPLC measurements indicated a purity of 92.50%.

Purification of Compound 5 (BL-1023):

Purification was performed by dissolving Compound 5 in isopropanol and adding the obtained solution to dichloromethane (DCM, 10 times volume). The precipitation of the compound occurred slowly and the precipitate was thereafter filtered. This procedure was conducted under strict inert atmosphere.

The purification was conducted three times as far as after two successive batches the purity had significantly increased.

The three purified batches of Compound 5 were poured together, dissolved in methanol (150-200 ml) and concentrated in vacuum in order to obtain one homogeneous batch. This procedure was repeated six times in order to remove residual isopropanol (from the purification step). The obtained residue was then dried for six days at 65° C. in a vacuum drying oven, so as to afford 27.8 grams of Compound 5 as a slightly brown solid.

Overall yield was 10%.

$^1$H NMR (400 MHz, DMSO, TMS): δ=12.66 (br, COOH, 1H), 8.73 (br, OH, 2H), 8.17 (d, 3H, J=7.8 Hz, NH, 1H), 7.89 (br, 3H), 6.65-6.42 (m, 3H, Arom. H), 4.29 (m, H-2, 1H), 2.88-2.63 (m, $CH_2$, 4H), 2.18 (m, $CH_2$, 2H), 1.72 (m, $CH_2$, 2H).

IR: υ ($cm^{-1}$)=3235 (s), 3075 (s), 2929 (m), 1731 (m), 1646 (s), 1525 (m), 1445 (w), 1358 (w), 1287 (m), 1229 (m), 1203 (m), 1155 (w), 1115 (m), 979 (w), 875 (vw), 816 (m), 792 (w), 654 (w), 616 (w), 590 (w).

Heavy Metals: <0.002%.

ROI: 1.27%.

Water content: 1.24%.

Elemental analysis: Determined: 48.02% C, 6.08% H, 8.63% N; Calculated: 48.98% C, 6.01% H, 8.79% N MS (positive mode, single quadrupol 50V): m/z=283.2

DSC (heating rate 10° C./minute): 25-250° C.; endotherm at 77-78° C.; ca. 240° C. decomposition.

Purity (HPLC): 90.12%.

Stability Studies:

One sample of Compound 5 (BL-1023) was placed in an open vial and another sample was placed in a sealed vial and then placed on the bench top. KF and HPLC analyses were performed after 1, 3, 4 and 7 days and the data is presented in Table 2 below.

TABLE 2

|  | Starting point | 1 day | 3 days | 4 days | 7 days |
| --- | --- | --- | --- | --- | --- |
| kept sealed vial on Bench top | HPLC: 99.4% KF: 0.63% (G-25-1/06) slightly brownish powder |  |  | KF: 0.58% (G-25-5/06) | HPLC: 98.7% KF: 0.41% (G-27-1/06) |
| Kept in a open vial on bench top | HPLC: 99.4% KF: 0.63% (G-25-1/06) slightly brownish powder | HPLC: 98.9% KF: 3.8% (G-25-2/06) slightly brownish powder with some stickiness to it | HPLC: 99.4% KF: 5% (G-25-3/06) slightly brownish solid; Becoming one solid piece | HPLC: 99.4% KF: 5% (G-25-4/06) Became one solid piece |  |
|  |  |  |  | ↓ divided to 2 parts: Solid stuff (one solid piece) | HPLC: 99.0% KF: 5.9% (G-27-2/06) one solid piece |
|  |  |  |  | Broken up (powder) | HPLC: 99.0% Sticky semi-powder There's not enough material to make KF |

Preparation of Methyl Esters and Acid Addition Salts of the Mono-GABA-L-DOPA Conjugate Having a GABA Moiety Linked to L-DOPA via an Amide Bond:

Methyl esters and salts of mono-GABA-L-DOPA conjugates were successfully obtained using the synthetic pathway depicted in Scheme 3 below.

mixture was about 9. The mixture was stirred over night, diluted with EtOAc and washed three times with 1 M KHSO$_4$, three times with 1 M NaHCO$_3$, and three times with brine, dried over Na$_2$SO$_4$ and evaporated under reduced pressure to afford the crude product methyl-2-(tert-butyl-3-carbamoyl-propylcarbamate)-3-(3,4-dihydroxyphenyl)propanoate

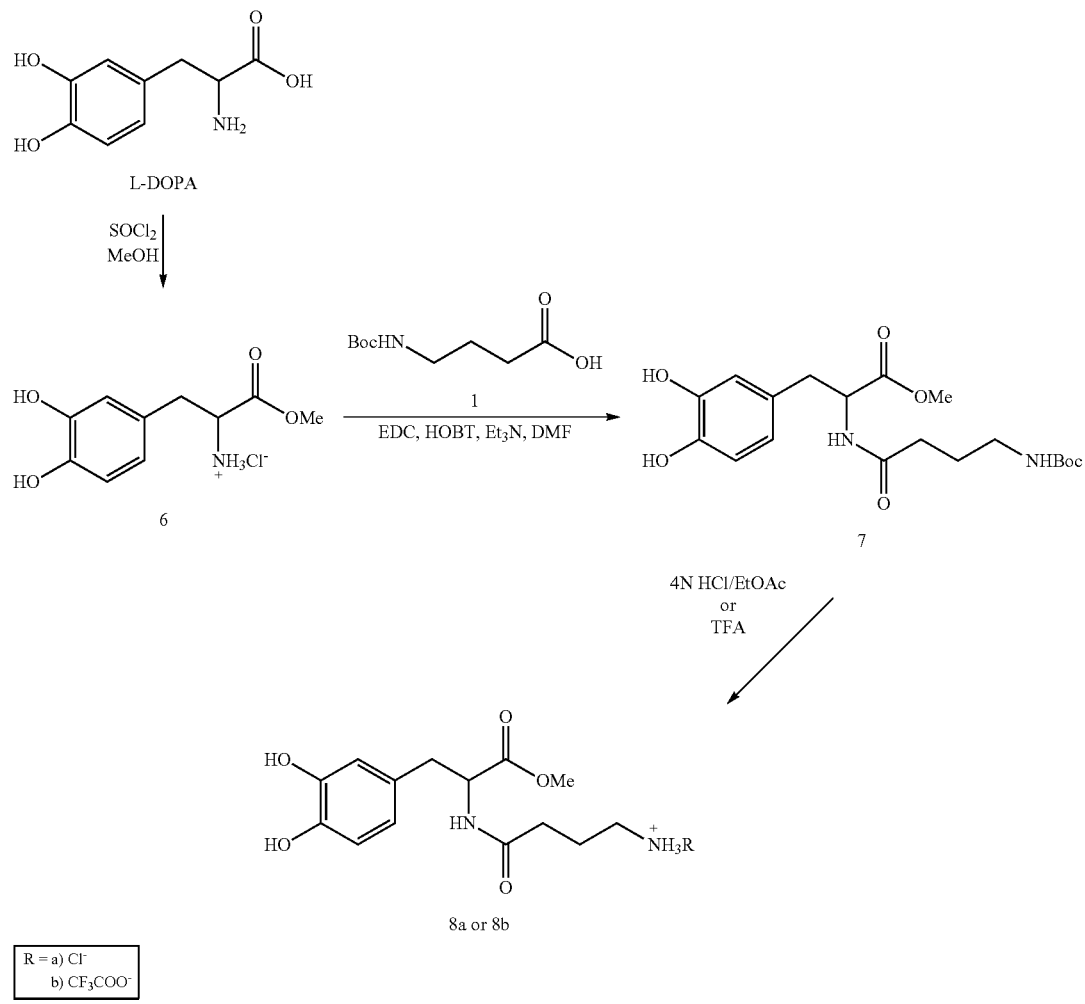

The ester Compound 6 was prepared using thionyl chloride (SOCl$_2$) in methanol (MeOH) as illustrated in Scheme 3. Compound 6 was reacted with Compound 1 (Boc-GABA), prepared as described hereinabove (see, Scheme 1). Compound 7 was synthesized by coupling Compound 6 with Compound 1 using 1-ethyl-3-(3-dimethylaminopropyl)carbodiimide hydrochloride (EDCl) and N-hydroxybenzotriazole (HOBt) in dimethylformamide (DMF) (see, Scheme 3). The subsequent removal of the Boc protective group was carried out under acidic conditions of 4N HCl in EtOAc or with TFA to afford Compound 8a and Compound 8b.

Specifically, EDCl (1.1 equivalents) and HOBt (1.1 equivalents) were added to a stirred and cooled solution of Compound 1 (Boc-GABA, 1 equivalent) in DMF (10 ml per mmol) in an ice bath. After 1 hour of stirring the ice bath was removed and Compound 6 (L-DOPA ester, 1 equivalent) and Et$_3$N (3 equivalents) were added and the pH of the reaction (Compound 7) as a sticky white solid (50% yield), and used in the next steps without further purification.

Compound 7

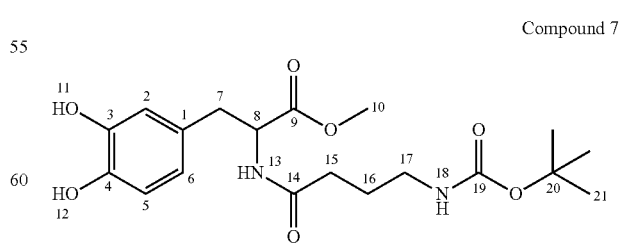

$^1$H-NMR (300 MHz, CDCl$_3$) ppm: δ=6.75 (d, J=8.4 Hz, 1H, H-5), 6.69 (bs, 1H, H-2), 6.47 (dd, J=8.4, 2.1 Hz, 1H, H-6), 4.99 (bs, 1H, H-11 or H-12), 4.78 (m, 1H, H-8), 3.71 (s, 3H, H-10), 3.08-3.02 (m, 3H, H-17+H-7), 2.91 (m, 1H, H-7), 2.2 (m, 2H, H-15), 1.75 (m, 2H, H-16), 1.43 (s, 9H, H-21);

$^{13}$C-NMR (300 MHz, CDCl$_3$) ppm: δ=173.04 (1C, C-14), 172.35 (1C, C-9), 156.99 (1C, C-19), 144.26 (1C, C-3), 143.79 (1C, C-4), 127.82 (1C, C-1), 121.05 (1C, C-6), 116.38 (1C, C-5), 115.36 (1C, C-2), 80.13 (1C, C-20), 53.75 (1C, C-8), 52.55 (1C, C-10), 39.91 (1C, C-17), 37.12 (1C, C-7), 33.48 (1C, C-15), 28.51 (3C, C-21), 21.16 (1C, C-16);

MS analysis (TOF, ES$^+$) m/z for C$_{19}$H$_{28}$N$_2$O$_7$ (calculated=396.19): [MH$^+$]=397; [M+Na$^+$]=419; [MH$^+$-Boc]=297.

N-Boc deprotection solution was prepared by slowly adding acetyl chloride (28.5 ml) to an ice-cold solution of EtOAc (20 ml) and EtOH (23.5 ml) in a 250 ml flame dried flask, equipped with a drying tube and magnetic stirrer, followed by the addition of EtOAc to a total volume of 100 ml. The ice bath was thereafter removed and the solution was used immediately.

The N-Boc protecting group was removed by dissolving Compound 7 in a freshly prepared solution of 4N HCl in EtOAc. The reaction mixture was stirred for 1 hour at room temperature, and thereafter the solvent was evaporated under reduced pressure to afford the crude deprotected product methyl-2-(4-aminobutanamide)-3-(3,4-dihydroxyphenyl) propanoate hydrochloride (Compound 8a) was obtained as a white solid (81% yield).

Compound 8a

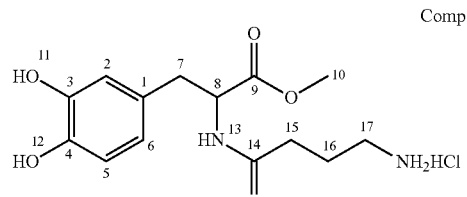

$^1$H-NMR (300 MHz, D$_2$O) ppm: δ=6.83 (d, J=7.85 Hz, 1H, H-5), 6.74 (bs, 1H, H-2), 6.66 (bd, J=7.85 Hz, 1H, H-6), 4.64 (m, 1H, H-8), 3.72 (s, 3H, H-10), 3.09 (m, 1H, H-7), 2.82 (m, 3H, H-7+H-17), 2.31 (td, J=7.5, 2.4 Hz, 2H, H-5), 1.81 (quint, J=7.5 Hz, 2H, H-16);

$^{13}$C-NMR (200 MHz, D$_2$O) ppm: δ=176.59 (1C, C-14), 175.72 (1C, C-9), 145.89 (1C, C-3 or C:4), 144.87 (1C, C-3 or C-4), 131.22 (1C, C-1), 123.56 (1C, C-6), 118.88 (1C, C-2 or C-5), 118.25 (1C, C-2 or C-5), 56.13 (1C, C-8), 54.92 (1C, C-10), 40.66 (1C, C-17), 37.93 (1C, C-7), 34.05 (1C, C-15), 24.81 (1C, C-16);

HRMS analysis (CH$_4$) m/z for C$_{14}$H$_{20}$N$_2$O$_5$ (calculated=296.137): [M]=296.147; [MH$^+$]=297.146; [MH$^+$-NH$_3$]=280.124;

Chemical analysis calculated for C$_{14}$H$_{21}$ClN$_2$O$_5$.0.5H$_2$O: C 49.23%, H 6.90%, N 8.04% and O 25.67%.

Compound 8b

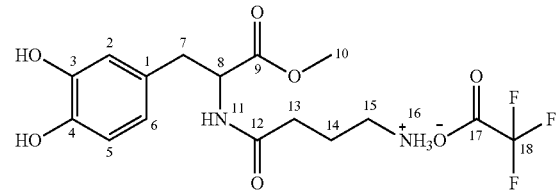

Compound 7 (370 mg, 0.93 mmol) was dissolved in trifluoroacetic acid (TFA, 10 ml) and stirred at room temperature for 1 hour and TFA was evaporated under reduced pressure. The oily residue was dissolved in ether and evaporated under reduced pressure to give the product methyl 2-(4-aminobutanamide)-3-(3,4-dihydroxyphenyl)propanoate2,2,2-trifluoroacetate salt (Compound 8b) as a sticky white solid in quantitative yield.

$^1$H-NMR (200 MHz, D$_2$O) ppm: δ=6.82 (d, J=7.1 Hz, 1H, H-5), 6.72 (bs, 1H, H-2), 6.64 (dd, J=7.1, 2.4 Hz, 1H, H-6), 4.64 (m, 1H, H-8), 3.05 (dd, J=14.3, 4.8 Hz, 1H, H-7), 2.82 (m, 3H, H-7+H-15), 2.29 (t, J=7.1 Hz, 2H, H-13), 1.79 (quint, J=7.1 Hz, 2H, H-14);

$^{13}$C-NMR (200 MHz, D$_2$O) ppm: δ=176.54 (1C, C-12), 175.72 (1C, C-9), 164.34 (1C, C-17), 145.86 (1C, C-3 or C-4), 144.83 (1C, C-3 or C-4), 131.28 (1C, C-1), 123.56 (1C, C-6), 118.89 (1C, C-2 or C-5), 118.23 (1C, C-2 or C-5), 56.02 (1C, C-8), 50.90 (1C, C-10), 40.63 (1C, C-15), 37.91 (1C, C-7), 34.04 (1C, C-13), 24.78 (1C, C-14);

HRMS analysis (DCI, CH$_4$) m/z for C$_{14}$H$_{20}$N$_2$O$_5$ (calculated=296.137): [MH$^+$]=297.145.

Preparation of bis-GABA-L-DOPA Methyl Ester (Having Two GABA Moieties Linked to L-DOPA via Carboxylic Ester Bonds)

Compounds having two GABA moieties conjugated to L-DOPA were successfully prepared as illustrated in Scheme 4 below. The diester Compound 11 was prepared using 2 equivalents of Compound 1 (Boc-GABA) and Boc-protected-L-DOPA ester (Compound 9, Scheme 4), which afforded Compound 10 at a 80% yield, followed by N-deprotection thereof to afford Compound 11 at 61% yield.

Scheme 4

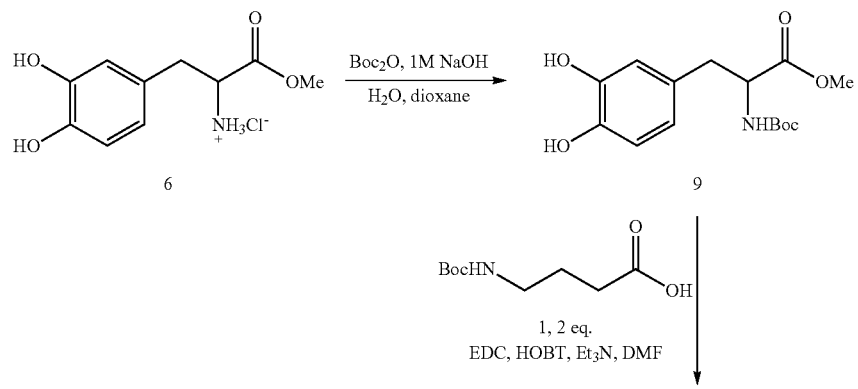

A solution of 1M NaOH (1 equivalent) was added to a solution Compound 6 (L-DOPA ester, 1 equivalent) in dioxane (2 ml per mmol) and water (1 ml per mmol). After 10 minutes Boc₂O (1 equivalent) was added and the reaction mixture was stirred at room temperature over night. Thereafter the reaction mixture was concentrated under reduced pressure and the resulting residue was dissolved in EtOAc, washed three times with 1M KHSO₄, three times 1M NaHCO₃, three times brine, and dried over Na₂SO₄ and evaporated under reduced pressure to afford the crude product, tert-butyl-1-(methoxycarbonyl)-2-(3,4-dihydroxyphenyl)ethylcarbamate (Compound 9).

Compound 9 was obtained at 94% yield and used for the next step without further purification.

$^1$H-NMR (300 MHz, CDCl₃) ppm: δ=6.73 (d, J=7.99 Hz, H-5), 6.64 (bs, 1H, H-2), 6.49 (dd, J=7.99, 1.8 Hz, 1H, H-6), 5.10 (d, J=8.1 Hz, 1H), 4.49 (m, 1H, H-8), 3.71 (s, 3H, H-10), 2.93 (m, 2H, H-7), 1.40 (s, 9H, H-16);

$^{13}$C-NMR (200 MHz, CDCl₃) ppm: δ=172.69 (1C, C-9), 155.55 (1C, C-14), 143.97 (1C, C-3 or C-4), 143.13 (1C, C-3 or C-4), 128.26 (1C, C-1), 121.47 (1C, C-6), 116.17 (1C, C-2 or C-5), 115.34 (1C, C-2 or C-5), 80.45 (1C, C-15), 54.67 (1C, C-8), 52.31 (1C, C-10), 37.64 (1C, C-7), 28.26 (3C, C-16);

MS analysis (TOF, ES⁺) m/z for C₁₅H₂₁NO₆ (calculated=311.14): [M+Na⁺]=334.

EDCl (2.2 equivalents) and HOBt (2.2 equivalents) were added to an ice-cold and stirred solution of Compound 1 (Boc-GABA, 2 equivalents) in DMF (10 ml per mmol). After 1 hour the ice bath was removed and Compound 9 (N-Boc-L-DOPA methyl ester, 1 equivalent) and Et₃N (6 equivalents) were added thereto, raising the pH to higher than 10. The reaction mixture was stirred over night, diluted with EtOAc and washed with 1M KHSO₄ (three times), 1M NaHCO₃ (three times), brine (three times), dried over Na₂SO₄ and evaporated under reduced pressure to afford the crude product tert-butyl-1-(methoxycarbonyl)-2-(3,4-[di-tert-butyl-4-butoxyphenylcarbamate])-dihydroxyphenyl)ethylcarbamate (Compound 10).

Compound 10 was obtained as a white solid at 81% yield, dissolved in DMF, and used in the next step without further purification.

$^1$H-NMR (300 MHz, CDCl₃) ppm: δ=7.11 (d, J=8.14 Hz, 1H, H-5), 7.00 (dd, J=8.14, 1.25 Hz, 1H, H-6), 6.97 (d, J=1.25 Hz, 1H, H-2), 4.55 (m, 1H, H-8), 3.69 (s, 3H, H-10), 3.21 (m, 4H, H-18+H-26), 3.06 (t, J=4.38 Hz, 2H, H-7), 2.57 (t, J=7.30 Hz, 4H, H-16+H-24), 1.89 (m, 4H, H-17+H-25), 1.43-1.41 (two overlapping singlets, 29H, H-14+H-22+H-30);

$^{13}$C-NMR (300 MHz, CDCl₃) ppm: δ=172.13 (2C, C-15+C-23), 170.58 (1C, C-9), 156.20 (3C, C-12+C-20+C-28), 141.90 (1C, C-3), 141.03 (1C, C-4), 135.05 (1C, C-1), 127.43 (1C, C-6), 124.39 (1C, C-5), 123.49 (1C, C-2), 80.19+79.49 (3C, C-13+C-21+C-29), 54.36 (1C, C-8), 52.48 (1C, C-10), 39.91 (2C, C-18+C-26), 37.79 (1C, C-7), 31.39 (2C, C-16+C-24), 28.53 (6C, C-22+C-30), 28.39 (3C, C-14), 25.43 (2C, C-17+C-25);

MS analysis (TOF, ES⁺) m/z for C₃₃H₅₁N₃O₁₂: (calculated=681.35): [M+Na⁺]=704.

N-Boc deprotection of Compound 10 was performed by dissolving Compound 10 in a freshly prepared solution of 4N HCl in EtOAc, prepared as described hereinabove. The mixture was stirred for 1 hour at room temperature, and the solvent was evaporated under reduced pressure to afford the crude product methyl-2-amino-3-(3,4-phenyl-di-[4-aminobutanoate])propanoate-trihydrochloride (Compound 11).

Crude Compound 11 was washed with ether to afford a yellowish solid that was recrystallized from MeOH/ether to afford Compound 11 at 82% yield.

Melting point (mp): 185° C.;

$^1$H-NMR (300 MHz, D$_2$O) ppm: δ=7.32+7.31 (two overlapping picks, 2H, H-2+H-5), 7.25 (bs, 1H, H-6), 4.47 (t, J=6.78 Hz, 1H, H-8), 3.84 (s, 3H, H-10), 3.41-3.25 (m, 2H, H-7), 3.12 (t, J=7.91 Hz, 4H, H-15+H-20), 2.82 (t, J=7 Hz, 4H, H-13+H-18), 2.07 (m, 4H, H-14+H-19);

$^{13}$C-NMR (200 MHz, D$_2$O) ppm: δ=174.75 (2C, C-12+C-17), 171.77 (1C, C-9), 143.64 (1C, C-3 or C-4), 143.09 (1C, C-3 or C-9), 135.85 (1C, C-1), 130.71 (1C, C-6), 126.63 (1C, C-2 or C-5), 126.32 (1C, C-2 or C-5), 55.94 (1C, C-8 or C-10), 55.78 (1C, C-8 or C-10), 40.70 (2C, C-15+C-20), 36.94 (1C, C-7), 32.43 (2C, C-13+C-18), 24.01 (2C, C-14+C-19);

HRMS analysis (DCI, CH$_4$) m/z for C$_{18}$H$_{27}$N$_3$O$_6$ (calculated=381.190: [M]=381.190;

Chemical analysis for C$_{18}$H$_{27}$N$_3$O$_6$·H$_2$O: C 42.70%; H 6.56%; N 8.67%; O 22.31%.

Preparation of tris-GABA-L-DOPA Methyl Ester
(Having Three GABA Moieties Linked to L-DOPA via Ester and Amide Bonds)

The tris-GABA-L-DOPA (Compound 13) was prepared using 3 equivalents of Compound 1 (N-Boc-GABA) and Compound 6, followed by deprotection of the resulting Compound 12, at 83% yield (Scheme 5).

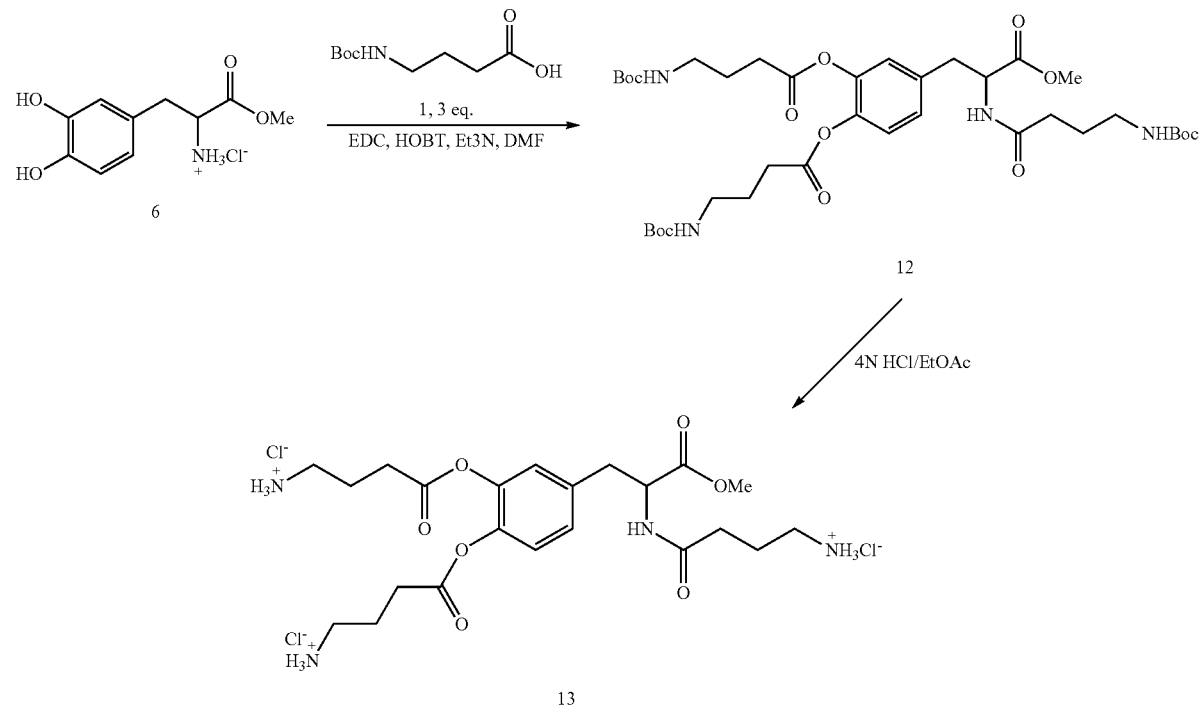

2-[(N-4-Aminobutyramido)-3-(3,4-bis-(4-tert-butoxycarbonyl-amino butyryloxy)phenyl]propionate methyl ester (Compound 12) was obtained as a white solid in 84% yield and used without further purification.

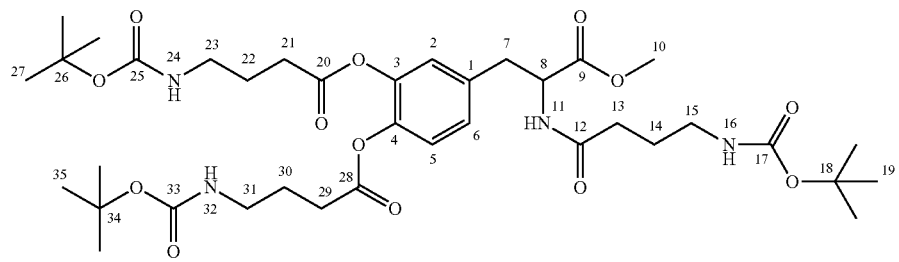

$^1$H NMR (300 MHz, CDCl$_3$) ppm: δ=7.07 (d, J=7.53 Hz, 1H, H-5), 6.99 (d, J=7.53 Hz, 1H, H-6), 6.66 (bs, 1H, H-2), 4.81 (m, 1H, H-8), 3.69 (s, 3H, H-10), 3.21-2.99 (m, 8H, H-7+H-15+H-23+H-31), 2.55 (t, J=7.47 Hz, 4H, H-21+H-29), 2.19 (t, J=7.47 Hz, 2H, H-13), 1.87 (m, 4H, H-22+H-30), 1.71 (m, 2H, H-14), 1.40 (bs, 27H, H-19+H-27+H-35);

$^{13}$C-NMR (300 MHz, CDCl$_3$) ppm: δ=172.71 (1C, C-12), 171.94+170.72 (3C, C-9+C-20+C-28), 156.53+156.23 (3C, C-17+C-25+C-33), 141.81 (1C, C-3), 140.95 (1C, C-4), 135.00 (1C, C-1), 127.23 (1C, C-6), 124.54 (1C, C-5), 123.47 (1C, C-2), 79.37 (3C, C-18+C-26+C-39), 53.09 (1C, C-8), 52.54 (1C, C-10), 39.88 (2C, C-23+C-31), 37.07 (1C, C-15), 33.33 (1C, C-13), 31.31 (2C, C-21+C-29), 28.49 (9C, C-19+C-27+C-35), 26.13 (1C, C-14), 25.37 (2C, C-22+C-30);

MS analysis (TOF, ES$^+$) m/z for C$_{37}$H$_{58}$N$_4$O$_{13}$ (calculated=766.40): [MH$^+$]=767; [M+Na$^+$]=789.

2-[(N-4-Aminobutyramido)-3-(3,4-bis-(4-amino butyroyloxy)phenyl]propanoate methyl ester tri-hydrochloride (Compound 13) was obtained from Compound 12 as a white powder in quantitative yield.

Compound 13

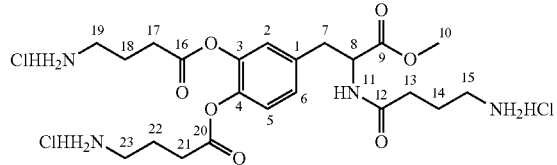

Melting point (mp): 87° C.;

$^1$H-NMR (300 MHz, D$_2$O) ppm: γ=7.26 (d, J=1.2 Hz, 2H, H-5+H-6), 7.19 (bt, J=1.2 Hz, 1H, H-2), 4.73 (m, 1H, H-8), 3.75 (s, 3H, H-10), 3.28 (dd, J=14, 5.8 Hz, 1H, H-7), 3.11 (bt, J=7.5 Hz, 4H, H-19+H-23), 3.03 (m, 1H, H-7), 2.88 (m, 2H, H-15), 2.82+2.81 (two overlapping t, J=7.5 Hz, 4H, H-17+H-21), 2.35+2.33 (two overlapping t, J=7.5 Hz, 2H, H-13), 2.07+2.06 (two overlapping quint, J=7.5 Hz, 4H, H-18+H-22), 1.84 (quint, J=7.5 Hz, 2H, H-14);

$^{13}$C-NMR (300 MHz, D$_2$O) ppm: δ=175.21 (1C, C-12), 173.82+173.26+173.15 (3C, C-9+C-16+C-20), 141.72 (1C, C-3 or C-4), 140.79 (1C, C-3 or C-4), 137.02 (1C, C-1), 128.84 (1C, C-6), 124.66 (1C, C-2 or C-5), 124.10 (1C, C-2 or C-5), 54.40 (1C, C-8 or C-10), 54.18 (1C, C-8 or C-10), 39.23+39.14 (3C, C-15+C-19+C-23), 36.43 (1C, C-7), 32.63 (1C, C-13), 30.91 (2C, C-17+C-21), 23.36 (1C, C-14), 22.51 (2C, C-18+C-22);

HRMS analysis (DCI, CH$_4$) m/z for C$_{22}$H$_{34}$N$_4$O$_7$ (calculated=466.243): [M]=466.242.

Preparation of Butyl Esters of mono-GABA-L-DOPA (BL-1023*, Compound 16), bis-GABA-L-DOPA (AN-490, Compound 21) and tri-GABA-L-DOPA (Compound 18)

Preparation of L-DOPA Butyl Ester:

A recent study reported by Reichman et al. showed that L-DOPA butyl ester has better skin permeability then other esters such as the ethyl or octyl esters. Hence the butyl ester of exemplary GABA-L-DOPA conjugates according to some embodiments of the invention, corresponding to the methyl esters Compound 8, Compound 11 and Compound 13 have been prepared.

Butyl-2-amino-3-(3,4-dihydroxyphenyl)propanoate hydrochloride (Compound 14) was obtained in quantitative yield as illustrated in Scheme 6 below.

Scheme 6

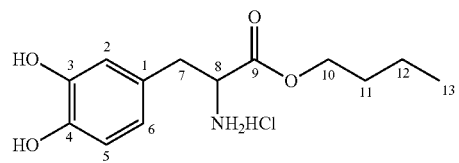

SOCl$_2$ (16.5 ml, 228.2 mmol) was added drop wise and under argon to an ice-cold and stirred suspension of L-DOPA (5 grams, 25.4 mmol) in n-BuOH (200 ml). The solution was stirred at room temperature for 20 hours and the solvent was evaporated under reduced pressure. The resulting oily residue was dissolved in water and the aqueous phase was washed three times with hexane, three times with ether and thereafter lyophilized under reduced pressure to afford Compound 12 as an amber solid in quantitative yield (7.3 grams).

Compound 14

$^1$H-NMR (300 MHz, D$_2$O) ppm: δ=6.87 (d, J=8.58 Hz, 1H, H-5), 6.75 (d, J=2.52 Hz, 1H, H-2), 6.66 (dd, J=8.58, 2.52 Hz, 1H, H-6), 4.32 (t, J=7.78 Hz, 1H, H-8), 4.18 (t, J=6.67 Hz, 2H, H-10), 3.11 (d, J=7.78 Hz, 2H, H-7), 1.54 (m, 2H, H-11), 1.22 (sex, J=8.31 Hz, 2H, H-12), 0.85 (t, J=8.31 Hz, 3H, H-13);

$^{13}$C-NMR (300 MHz, D$_2$O) ppm: δ=170.33 (1C, C-9), 144.84+144.21 (2C, C-3+C-4), 126.61 (1C, C-1), 122.29 (1C, C-6), 117.46+117.08 (2C, C-5+C-6), 67.68 (1C, C-10), 54.71 (1C, C-8), 35.71 (1C, C-7), 30.22 (1C, C-11), 18.96 (1C, C-12), 13.47 (1C, C-13);

MS analysis (TOF, ES$^+$) m/z for C$_{13}$H$_{19}$NO$_4$ (calculated=253.13): [MH$^+$]=254; [MH$^+$—NH$_3$]=237.

Preparation of mono- bis- and tri-GABA-L-DOPA Butyl Ester Derivatives (Compounds 16 (BL-1023*), 21 (AN-490) and 18 Respectively):

The mono-, bis- and tris-GABA-L-DOPA butyl ester derivatives, namely Compound 16, Compound 21 and Compound 18, were prepared as illustrated in Scheme 7 below and described hereinabove for the methyl esters.

41
42
Scheme 7
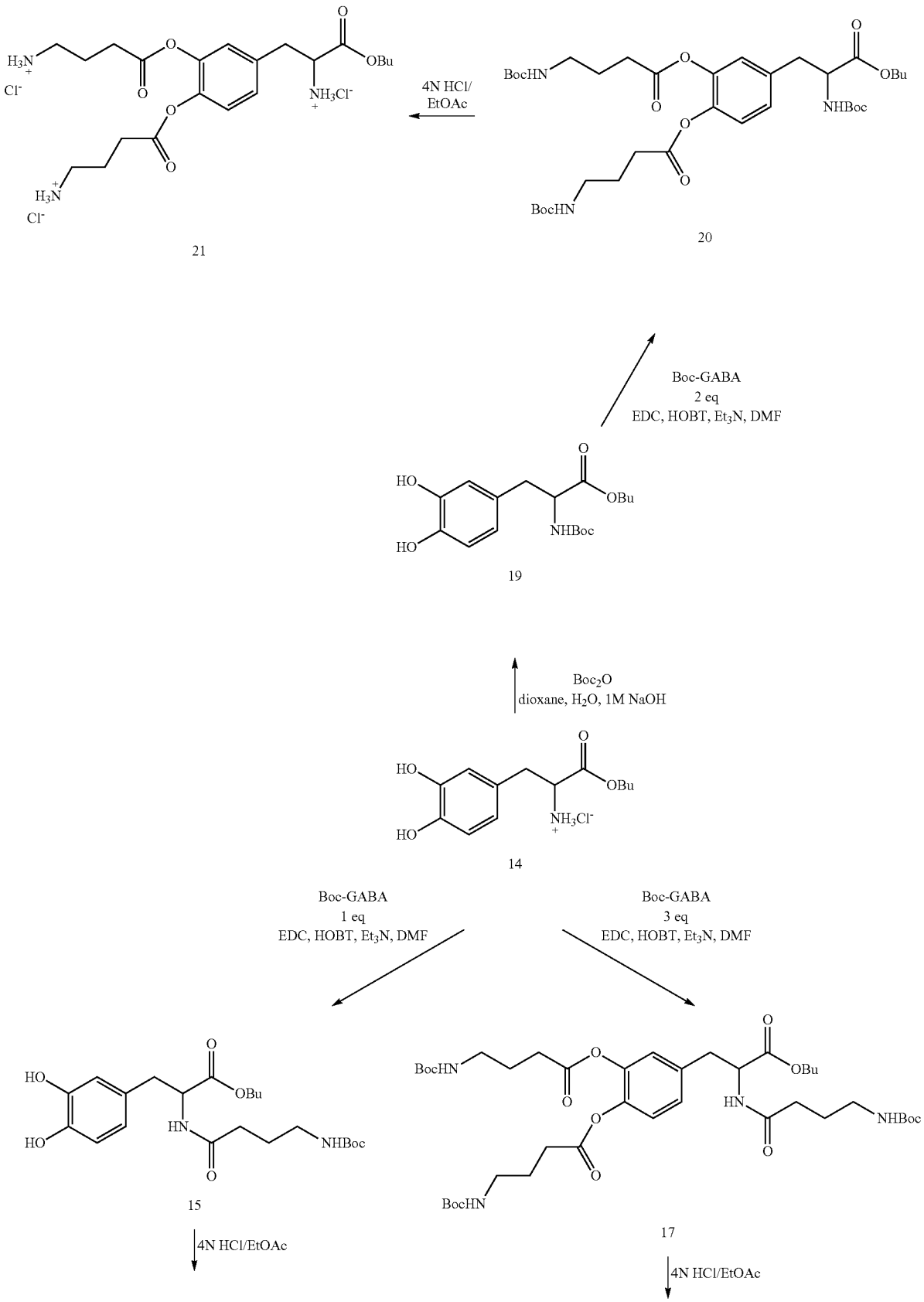

-continued

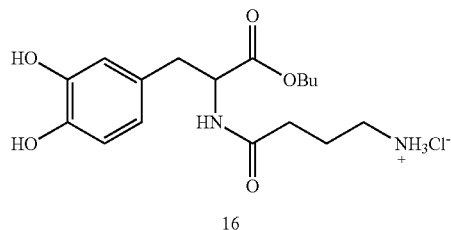

16

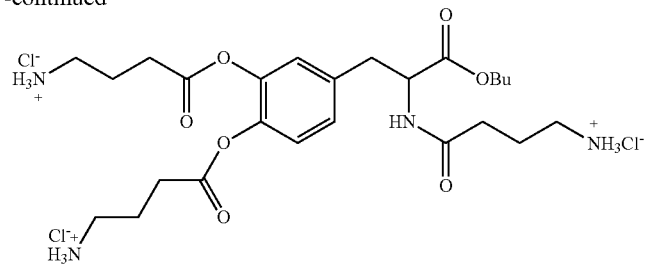

18

Butyl-2-(tert-butyl-3-carbamoylpropylcarbamate)-3-(3,4-dihydroxyphenyl)propanoate (Compound 15) was obtained as foam at 89% yield from Compound 14 and was used without further purification.

Compound 15 to afford a solid which was washed with ether and dried under reduced pressure. The solid was dissolved in water and washed three times with ether. The aqueous phase was evaporated and lyophilized to afford the Compound 16 as yellowish solid at 85% yield.

Compound 15

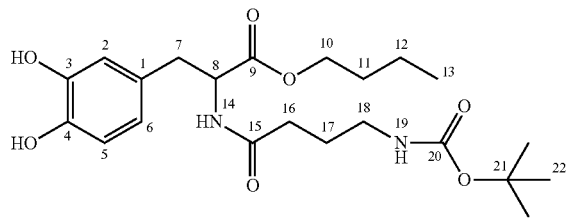

$^1$H-NMR (300 MHz, CDCl$_3$) ppm: δ=6.74 (d, J=7.87 Hz, 1H, H-5), 6.69 (bs, 1H, H-2), 6.47 (dd, J=7.87, 1.79 Hz, 1H, H-6), 5.00 (bs, 1H, phenol), 4.77 (dd, J=13, 6.6 Hz, 1H, H-8), 4.10 (t, J=6.5 Hz, 2H, H-10), 3.05 (m, 3H, H-7+H-18), 2.90 (dd, J=13, 6.6 Hz, 1H, H-7), 2.18 (m, 2H, H-16), 1.82-1.70 (m, 2H, H-17), 1.59 (m, 2H, H-11), 1.43 (s, 9H, H-22), 1.35 (m, 2H, H-12), 0.91 (t, J=7.5 Hz, 3H, H-13);

$^{13}$C-NMR (300 MHz, CDCl$_3$) ppm: δ=173.01 (1C, C-15), 172.00 (1C, C-9), 156.97 (1C, C-20), 144.27 (1C, C-3 or C-4), 143.78 (1C, C-3 or C-4), 127.85 (1C, C-1), 121.08 (1C, C-6), 116.42 (1C, C-2 or C-5), 115.33 (1C, C-2 or C-5), 80.07 (1C, C-21), 65.64 (1C, C-10), 53.76 (1C, C-8), 39.92 (1C, C-18), 37.21 (1C, C-7), 33.46 (1C, C-16), 30.59 (1C, C-11), 28.51 (3C, C-22), 26.07 (1C, C-17), 19.17 (1C, C-12), 13.76 (1C, C-13);

MS analysis (TOF, ES$^+$) m/z for C$_{22}$H$_{34}$N$_2$O$_7$ (calculated=438.24: [MH$^+$]=439; [M+Na$^+$]=461; [MH$^+$-Bu]=383; [MH$^+$-Bu-CO$_2$]=340.

Butyl-2-(4-Aminobutanamide)-3-(3,4-dihydroxyphenyl)propanoate hydrochloride (Compound 16) was obtained from Compound 16

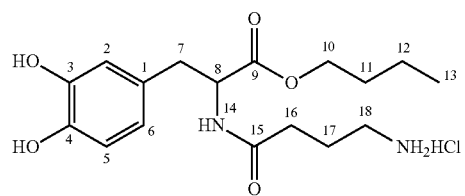

Melting point (mp): 77° C.;

$^1$H-NMR (300 MHz, D$_2$O) ppm: δ=6.84 (d, J=7.77 Hz, 1H, H-5), 6.74 (d, J=2.43 Hz, 1H, H-2), 6.64 (dd, J=7.77, 2.43 Hz, 1H, H-6), 4.55 (dd, J=8.78, 7.02 Hz, 1H, H-8), 4.08 (t, J=7.02 Hz, 2H, H-10), 3.00 (m, 1H, H-7), 2.92 (m, 3H, H-7+H-18), 2.34 (t, J=6.99 Hz, 2H, H-16), 1.85 (quint, J=6.99 Hz, 2H, H-17), 1.52 (m, 2H, H-11), 1.21 (sex, J=6.99 Hz, 2H, H-12), 0.84 (t, J=6.99 Hz, 3H, H-13);

$^{13}$C-NMR (300 MHz, D$_2$O) ppm: δ=175.12 (1C, C-15), 174.18 (1C, C-9), 144.46+143.47 (2C, C-3+C-4), 129.43 (1C, C-1), 122.01 (1C, C-6), 117.33+116.74 (2C, C-2+C-5), 66.76 (1C, C-10), 55.11 (1C, C-8), 39.18 (1C, C-16 or C-18), 36.58 (1C, C-16 or C-18), 32.52 (1C, C-7), 30.31 (1C, C-11), 23.39 (1C, C-17), 19.00 (1C, C-12), 13.44 (1C, C-13);

HRMS analysis (DCI, CH$_4$) m/z for C$_{17}$H$_{26}$N$_2$O$_5$ (calculated=338.184): [MH$^+$]=339.166.

2-[(N-4-Aminobutyramido)-3-(3,4-bis-(4-tert-butoxycarbonyl-aminobutyryloxy)phenyl]propionate butyl ester (Compound 17) was obtained as a white solid from Compound 16 after recrystallization from DCM:ether at 77% yield.

Compound 17

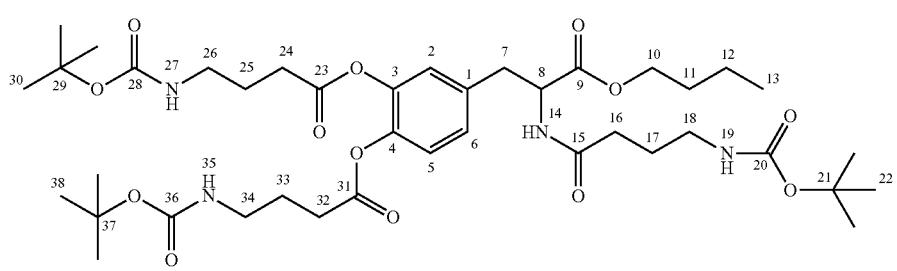

Melting point (mp): 125-126° C.;

$^1$H-NMR (300 MHz, CDCl$_3$) ppm: δ=7.08 (d, J=8.22 Hz, 1H, H-5), 7.01-6.98 (two broad peaks, 2H, H-2+H-6), 4.82 (m, 1H, H-8), 4.1 (td, J=6.02, 3 Hz, 2H, H-10), 3.2 (t, J=7.52 Hz, 4H, H-26+H-34), 3.13-3.00 (m, 4H, H-7+H-18), 2.58 (t, J=7.90 Hz, 4H, H-24+H-32), 2.20 (t, J=6.60 Hz, 2H, H-16), 1.90 (m, 4H, H-25+H-33), 1.74 (m, 2H, H-17), 1.60-1.53 (m, 2H, H-11), 1.44+1.41 (two s, 27H, H-22+H-30+H-38), 1.39-1.29 (m, 2H, H-12), 0.90 (t, J=6.60 Hz, 3H, H-13);

$^{13}$C-NMR (300 MHz, CDCl$_3$) ppm: δ=172.61 (1C, C-15), 171.54+170.59 (3C, C-9+C-23+C-31), 156.42+156.15+156.12 (3C, C-20+C-28+C-36), 141.69 (1C, C-3 or C-4), 140.83 (1C, C-3 or C-4), 135.03 (1C, C-1), 127.14 (1C, C-6), 124.40 (1C, C-2 or C-5), 123.30 (1C, C-2 or C-5), 79.13 (3C, C-21+C-29+C-37), 65.42 (1C, C-10), 53.02 (1C, C-8), 39.71 (3C, C-18+C-26+C-34), 37.03 (1C, C-7), 33.23 (1C, C-16), 31.20+30.41 (3C, C-11+C-24+C-32), 28.39 (9C, C-22+C-30+C-38), 26.03 (1C, C-17), 25.26 (2C, C-25+C-33), 18.99 (1C, C-12), 13.61 (1C, C-13);

MS analysis (TOF, ES$^+$) m/z for C$_{40}$H$_{64}$N$_4$O$_{13}$ (calculated=808.45): [MH$^+$]809; [MH$^+$-Boc]=709.

2-[(N-4-Aminobutyramido)-3-(3,4-bis-(4-amino-butyroyloxy)phenyl]propanoate butyl ester tri-hydrochloride (Compound 18) was obtained from Compound 17 as a yellowish solid in quantitative yields.

Compound 18

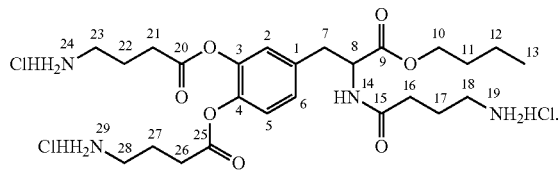

Melting point (mp): 74-75° C.;

$^1$H-NMR (300 MHz, D$_2$O) ppm: δ=7.27-7.16 (m, 3H, H-2+H-5+H-6), 4.68 (dd, J=9.0, 6.5 Hz, 1H, H-8), 4.10 (t, J=5.7 Hz, 2H, H-10), 3.24-2.87 (m, 8H, H-7+H18+H-23+H-28), 2.81 (td, J=7.4, 1.8 Hz, 4H, H-21+H-26), 2.34 (td, J=7.6, 2.0 Hz, 2H, H-16), 2.06 (m, 4H, H-22+H-27), 1.85 (quint, J=7.6 Hz, 2H, H-17), 1.53 (m, 2H, H-11), 1.27 (m, 2H, H-12), 0.86 (t, J=7.5 Hz, 3H, H-13);

$^{13}$C-NMR (300 MHz, D$_2$O) ppm: δ=175.18 (1C, C-15), 173.60 (1C, C-9), 173.17+173.06 (2C, C-20+C-25), 141.73 (1C, C-3 or C-4), 140.81 (1C, C-3 or C-4), 136.86 (1C, C-1), 128.78 (1C, C-6), 124.62 (1C, C-2 or C-5), 124.13 (1C, C-2 or C-5), 66.92 (1C, C-10), 54.50 (1C, C-8), 39.25+39.13 (3C, C-18+C-23+C-28), 36.47 (1C, C-7), 32.60 (1C, C-16), 30.91 (2C, C-21+C-26), 30.32 (1C, C-11), 23.38 (1C, C-17), 22.15 (2C, C-22+C-27), 19.05 (1C, C-12), 13.50 (1C, C-13);

HRMS analysis (DCI, CH$_4$) m/z for C$_{25}$H$_{40}$N$_4$O$_7$ (calculated=508.290): [M]=508.294; [C$_{17}$H$_{27}$N$_2$O$_5^+$]=339.187.

tert-Butyl-1-(butoxycarbonyl)-2-(3,4-dihydroxyphenyl)ethylcarbamate (Compound 19) was obtained at 85% yield from Compound 14 and the crude was used in the next step without further purification.

Compound 19

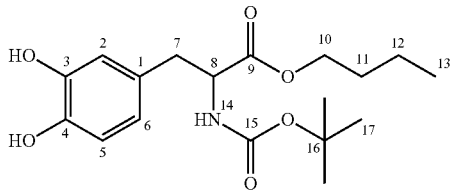

$^1$H-NMR (300 MHz, CDCl$_3$) ppm: δ=6.73 (d, J=8.1 Hz, 1H, H-5), 6.65 (bs, 1H, H-2), 6.49 (bd, J=8.1 Hz, 1H, H-6), 5.12 (d, J=8.4 Hz, 1H), 4.48 (m, 1H, H-8), 4.09 (t, J=6.30 Hz, 2H, H-10), 2.95 (m, 2H, H-7), 1.55 (m, 2H, H-11), 1.40 (s, 9H, H-17), 1.32 (m, 2H, H-12), 0.89 (t, J=7.2 Hz, H-13);

$^{13}$C-NMR (300 MHz, CDCl$_3$) ppm: δ=172.58 (1C, C-9), 155.70 (1C, C-15), 144.17 (1C, C-3 or C-4), 143.29 (1C, C-3 or C-4), 128.17 (1C, C-1), 121.41 (1C, C-6), 116.24 (1C, C-2 or C-5), 115.35 (1C, C-2 or C-5), 80.51 (1C, C-16), 65.55 (1C, C-10), 54.84 (1C, C-8), 37.89 (1C, C-7), 30.55 (1C, C-11), 28.36 (3C, C-17), 19.11 (1C, C-12), 13.72 (1C, C-13).

tert-Butyl-1-(butoxycarbonyl)-2-(3,4-[di-tert-butyl-4-butoxyphenyl carbamate])-dihydroxyphenyl)ethylcarbamate (Compound 20) was obtained from Compound 19 after recrystallization from DCM:ether which afforded a white solid, which was further filtered and recrystallized from ether: hexane to afford a second batch which wad combined to a total yield of 75%.

Compound 20

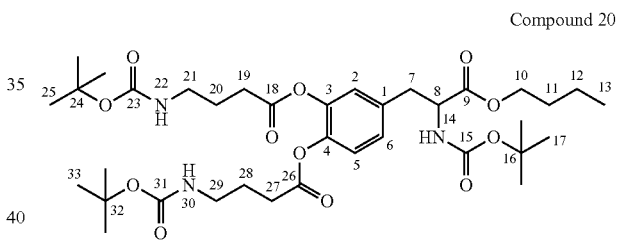

Melting point (mp): 85-86° C.;

$^1$H-NMR (300 MHz, CDCl$_3$) ppm: δ=7.10 (d, J=8.1 Hz, 1H, H-5), 7.01 (d, J=1.8 Hz, 1H, H-2), 6.98 (m, 1H, H-6), 5.05 (d, J=7.4 Hz, 1H), 4.91 (bs, 1H), 4.52 (m, 1H, H-8), 4.07 (t, J=6.6 Hz, 2H, H-10), 3.20 (t, J=6.8 Hz, 4H, H-21+H-29), 3.05 (m, 2H, H-7), 2.55 (t, J=7.4 Hz, 4H, H-19+H-27), 1.88 (quint, J=7.2 Hz, 4H, H-20+H-28), 1.54 (m, 2H, H-11), 1.42 (s, 18H, H-25+H-33), 1.40 (s, 9H, H-17), 1.30 (m, 2H, H-12), 0.88 (t, J=7.5 Hz, 3H, H-13);

$^{13}$C-NMR (300 MHz, CDCl$_3$) ppm: δ=171.73 (1C, C-9), 170.64+170.49 (2C, C-18+C-26), 156.17 (3C, C-15+C-23+C-31), 141.84 (1C, C-3 or C-4), 140.97 (1C, C-3 or C-4), 135.10 (1C, C-1), 127.39 (1C, C-6), 124.34 (1C, C-2 or C-5), 123.40 (1C, C-2 or C-5), 80.05+79.45 (2C, C-16+C-24+C-32), 65.47 (1C, C-10), 54.34 (1C, C-8), 39.93 (2C, C-21+C-29), 37.76 (1C, C-7), 31.33 (2C, C-19+C-27), 30.51 (1C, C-11), 28.49 (6C, C-25+C-33), 28.49 (3C, C-17), 25.42+25.39 (2C, C-20+C-28), 19.09 (1C, C-12), 13.70 (1C, C-13);

MS analysis (TOF, ES$^+$) m/z: for C$_{36}$H$_{57}$N$_3$O$_{12}$ (calculated=723.39): [MH$^+$]=724; [M+Na$^+$]=746; [MH$^+$-Boc]=624.

Butyl-2-amino-3-(3,4-phenyl-di[4-aminobutanoate])propanoate tri-hydrochloride (Compound 21) was obtained from Compound 20 after recrystallization from MeOH:ether to afford a white solid at 88% yield.

Compound 21

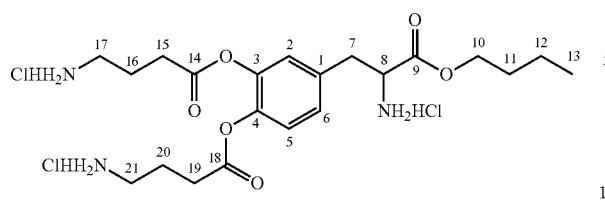

Melting point (mp): 175-176° C.;

$^1$H-NMR (300 MHz, D$_2$O) ppm: δ=7.36 (d, J=8.22 Hz, 1H, H-5), 7.33 (d, J=1.80 Hz, 1H, H-2), 7.29 (dd, J=8.22, 1.80 Hz, 1H, H-6), 4.46 (t, J=6.67 Hz, 1H, H-8), 4.24 (t, J=6.67 Hz, 2H, H-10), 3.34 (d, J=6.67 Hz, 2H, H-7), 3.15 (bt, 4H, H-17+H-21), 2.863+2.857 (t, J=7.19 Hz, 4H, H-15+H-19), 2.10 (quint, J=7.51 Hz, 4H, H-16+H-20), 1.60 (m, 2H, H-11), 1.29 (sex, J=7.78 Hz, 2H, H-12), 0.89 (t, J=7.78 Hz, 3H, H-13);

$^{13}$C-NMR (300 MHz, D$_2$O) ppm: δ=173.20 (2C, C-14+C-18), 169.98 (1C, C-9), 142.11+141.55 (2C, C-3+C-4), 134.37 (1C, C-1), 129.19 (1C, C-6), 125.11+124.82 (2C, C-2+C-5), 67.87 (1C, C-10), 54.42 (1C, C-8), 39.14 (2C, C-17+C-21), 35.57 (1C, C-7), 30.93 (2C, C-15+C-18), 30.21 (1C, C-11), 22.50 (2C, C-16+C-20), 19.00 (1C, C-12), 13.51 (1C, C-13);

HRMS analysis (DCI, CH$_4$) m/z: for C$_{21}$H$_{33}$N$_3$O$_6$ (calculated=423.237): [C$_{17}$H$_{27}$N$_2$O$_5$$^+$]=339.190 (no molecular peak, only fragments were detected).

Synthesis of C3 or C4 Mono GABA-L-DOPA Butyl Ester Derivative (Compounds 21a, and 21b)

The bis-GABA ester of L-DOPA butyl ester (compound 21, AN-490), contains three ammonium hydrochloride moieties, two of them belong to GABA moieties in the conjugate, and the other to L-DOPA. The compound, having three basic amino functionalities in the buffered in vivo environment, may be found in equilibrium with some protonated species which may be too polar in order to cross the BBB. The relatively high molecular weight of AN-490 (533 grams/mol) may also diminish the effectiveness of drug diffusion.

Therefore, mono-GABA-L-DOPA butyl ester derivatives, in which a single GABA moiety is linked to only one hydroxyl group of L-DOPA, either at the C-4 or at the C-3 position, yet leaving the n-butyl ester on the carboxylic moiety of L-DOPA unchanged, were synthesized. These compounds have a lower molecular weight (411 grams/mol), as compared to AN-490 and have only two basic amino groups, and are thus potentially more applicable for clinical use.

The synthetic strategy for a mono-GABA-L-DOPA butyl ester was similar to that used for preparing AN-490 (Compound 21) described hereinabove, with the required stoichiometric adjustments. Thus, N-protected L-DOPA n-butyl ester was reacted with one equivalent of carbodiimide-activated N-protected-GABA, as illustrated in Scheme 8 below.

Scheme 8

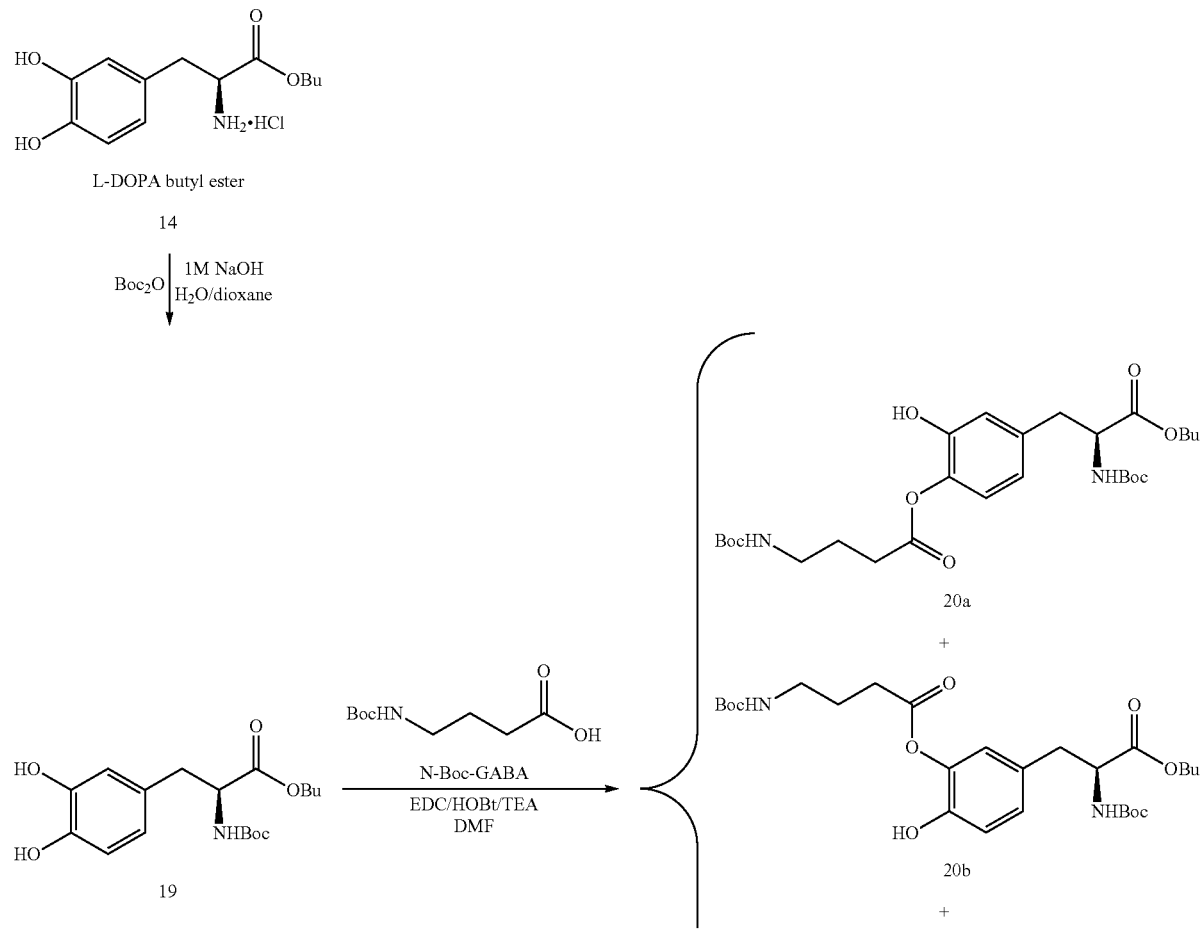

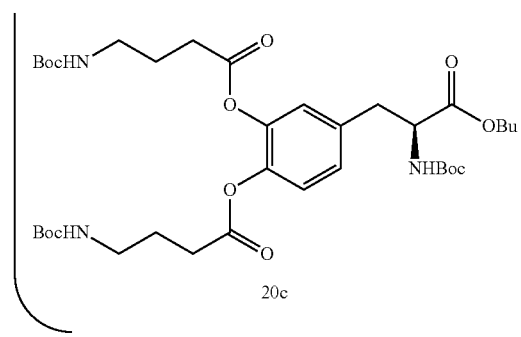

20c

L-DOPA was converted to the corresponding butyl ester 14 as described hereinabove, using thionyl chloride in n-butyl alcohol, and the obtained butyl ester was then N-protected by treatment with Boc.

The Boc protecting group was selected upon undesired results that were obtained while using N-carboxybenzyl (CBZ) protected Compound 14.

Thus, CBZ-protected Compound 14 was catalytically hydrogenated, via an addition-elimination reaction, so as to cleave the CBZ group and yield free L-DOPA and 2-pyrrolidone, the cyclic lactam of GABA.

Boc-protection of Compound 14 was performed by adding to a solution of L-DOPA alkyl ester (1 equivalent) in dioxane and water (2:1 v/v) 1 M NaOH solution (1 equivalent). After 10 minutes, di-tert-butyl dicarbonate (1 equivalent) was added and the reaction mixture was stirred at room temperature over night. The solvent was thereafter evaporated and the residue was diluted with water and EtOAc. The layers were separated and the organic layer was washed with 1 M $KHSO_4$ (×3), 1 M $NaHCO_3$ (×3) and brine (×3), dried over $Na_2SO_4$ and evaporated to give the crude Compound 19.

Compound 19

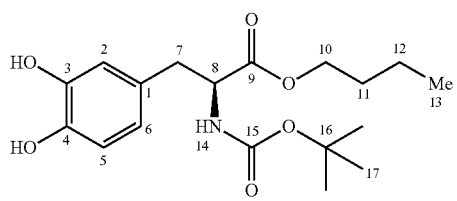

$^1$H NMR (300 MHz, $CDCl_3$) ppm: δ=0.84 (t, J=7.35 Hz, 3H, H-13), 1.27 (m, 2H, H-12), 1.37 (s, 9H, H-17), 1.52 (m, 2H, H-11), 2.76-2.96 (m, [AB of ABX system], 2H, H-7), 4.04 (m, 2H, H-10), 4.27-4.48 (m [X of ABX system], 1H, H-8), 5.23 (d, J=8.40 Hz, 1H, H-14), 6.46 (dd, $J_{ortho}$=8.10 Hz, $J_{meta}$=1.80 Hz, 1H, H-6), 6.64 (d, $J_{meta}$=1.80 Hz, 1H, H-2), 6.71 (d, $J_{ortho}$=8.10 Hz, 1H, H-5), 6.94 and 7.05 (two br s, 2H, 3-OH+4-OH);

$^{13}$C NMR (75 MHz, $CDCl_3$) ppm: δ=13.53 (C-13), 18.92 (C-12), 28.18 (C-17), 30.34 (C-11), 37.52 (C-7), 54.76 (C-8), 65.40 (C-10), 80.39 (C-16), 115.30 and 116.19 (C-2+C-5), 121.14 (C-6), 127.86 (C-1), 143.24 and 144.17 (C-3+C-4), 155.76 (C-15), 172.56 (C-9);

MS (CI+): m/z=354.194 ([MH]$^{·+}$, 4.66), 298.129 ([MH—$C_4H_8$]$^{·+}$, 31.85), 254.128 ([MH—$C_5H_8O_2$]$^{·+}$, 83.98), 236.090 ([$C_{13}H_{16}O_4$]$^{·+}$, 100.00);

HRMS calcd. for $C_{18}H_{28}NO_6$ ([MH]$^{·+}$, DCI, $CH_4$) 354.1917. found 354.1943.

The crude product was used in the next step without further purification.

The resulting N-Boc-protected butyl ester Compound 19 was mixed with EDC-activated N-Boc-GABA as follows:

To an ice-cold stirred solution of N-protected-GABA (1 equivalent) in DMF were added EDC (1.1 equivalent) and HOBt (1.1 equivalent). After 1 hour, the ice bath was removed and N-protected-L-DOPA butyl ester (Compound 19, 1 equivalent) and triethanolamine (TEA, 3 equivalents) were added. The mixture was stirred over night at room temperature, the solvent was thereafter evaporated, and the residue was dissolved in EtOAc and water. The layers were separated, and the organic phase was washed with 1 M $KHSO_4$ (×3), 1 M $NaHCO_3$ (×3), and brine (×3), dried over $Na_2SO_4$ and evaporated, to afford the "bis-ester" Compound 20c and an isomeric mixture of the mono-substituted 3-O- and 4-O-acylated catechols (Compounds 20a and 20b).

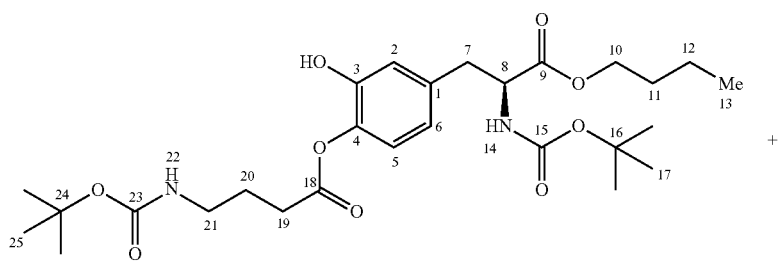

20a

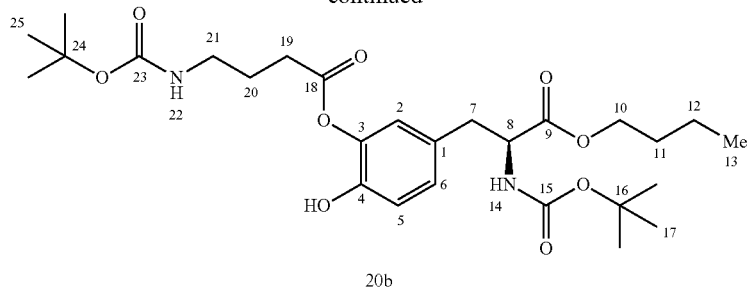

20b

The crude product was chromatographed twice (using as eluents $CHCl_3$:MeOH 80:1 v/v and then hexane:EtOAc 3:1 v/v), to provide a mixture of Compounds 20a and 20b as colorless oil in 37% yield. The ratio of the isomers in the mixture was determined based on $^1$H-NMR integrations of the H-2 in both isomers. The NMR data assignment was aided by several two-dimensional spectra including COSY, HMQC and HMBC analyses.

Unless otherwise indicated, the chemical shifts are assigned to both isomers. Superscript notations $^{a/b}$ refer to nuclei assigned to the corresponding isomers in the mixture.

$^1$H NMR (600 MHz, $CDCl_3$) ppm: δ=0.91 (t, J=7.20 Hz, 2.4H, H-13$^b$), 0.92 (t, J=7.50 Hz, 3H, H-13$^a$), 1.30-1.37 (m, ~4H, H-12), 1.42 and 1.43 (two overlapping singlets, ~16H, H-17), 1.46 (s, ~16H, H-25), 1.53-1.63 (m, ~4H, H-11), 1.85 (br quint, 3.6H, H-20), 2.62-2.64 (m, 3.6H, H-19), 2.82-3.06 (m, 3.6H, H-7), 3.28 (br q, 3.6H, H-21), 4.09 (t, J=6.60 Hz, 1.6H, H-10$^b$), 4.11 (t, J=6.30 Hz, 2H, H-10$^a$), 4.50 (br q, ~0.8H, H-8$^b$), 4.53 (br q, 1H, H-8$^a$), 4.79 (br t, 1.8H, H-22), 5.00 (br d, ~1.8H, H-14), 6.63 (dd, $J_{ortho}$=8.40 Hz, $J_{meta}$=1.80 Hz, 1H, H-6$^a$), 6.76 (br s, 0.8H, H-2$^b$), 6.82 (br s, 1H, H-2$^a$), 6.88 (m, 0.8H, H-6$^b$), 6.89 (d, $J_{ortho}$=8.40 Hz, 1H, H-5$^a$), 6.95 (d, $J_{ortho}$=7.80 Hz, 0.8H, H-5$^b$).

$^{13}$C NMR (determined by HMBC analysis; 150 MHz, $CDCl_3$) ppm: δ=13.66 (C-13), 13.05 (C-12$^b$), 19.07 (C-12$^a$), 25.99 (C-20), 28.32 (C-17), 28.40 (C-25), 29.99 (C-19), 30.52 (C-11), 37.44 (C-7$^b$), 37.85 (C-7$^a$), 38.20 (C-21), 54.38 (C-8$^a$), 54.53 (C-8$^b$), 65.25 (C-10$^b$), 65.29 (C-10$^a$), 79.90, 80.30 and 81.97 (C-16+C-24), 117.87 (C-5$^b$), 118.79 (C-2$^a$), 120.75 (C-6$^a$), 122.64 (C-5$^a$), 123.48 (C-2$^b$), 127.93 (C-6$^b$), 135.16 (C-1$^a$), 136.9 (C-4$^a$), 137.81 (C-3$^b$), 147.5 (C-4$^b$), 148.5 (C-3$^a$), 155.19 (C-15), 156.94 (C-23), 171.27 (C-18), 171.96 (C-9).

MS (CI+): m/z=539.296 ([MH]$^{·+}$, 4.23), 483.131 ([MH—$C_4H_8$]$^{·+}$, 4.46), 427.080 ([MH—$C_4H_8$—$C_4H_8$]$^{·+}$, 10.81), 383.107 (MH—$C_4H_8$—$C_5H_8O_2$]$^{·+}$, 71.89).

HRMS calcd. for $C_{27}H_{43}N_2O_9$ ([MH]$^{·+}$, DCI, $CH_4$) 539.2969. found 539.2961.

Removal of the N-Boc protecting groups of compounds 20a and 20b was performed as follows (see, Scheme 9 below): To an ice-cold solution of the obtained mixture of Compounds 20a and 20b as well as the undesired Compound 20c in EtOAc, a freshly prepared solution of 4 N HCl in EtOAc was added (obtained by addition of a known amount of acetyl chloride to an ice cold solution of an equivalent amount of EtOH in EtOAc). The ice bath was removed after 1 hour, and the solution was allowed to warm to room temperature. Once the reaction was completed (as monitored by TLC for complete consumption of Compounds 20a and 20b, the solvent was evaporated to give Compounds 21a and 21b.

Scheme 9

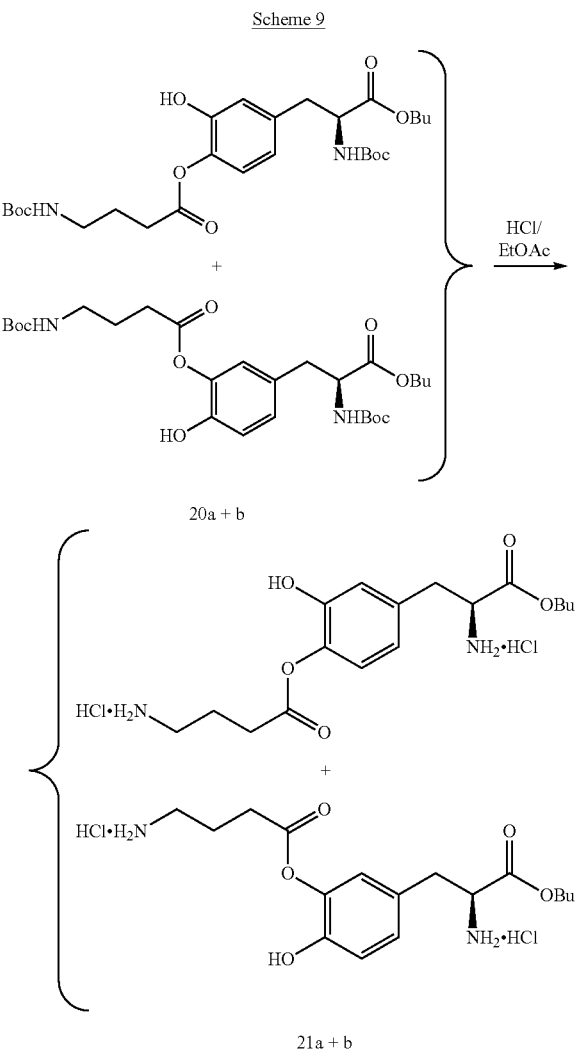

Remnants of the starting Boc-protected L-DOPA (Compound 19) were removed by flash chromatography. Subsequently, the monoesters' mixture of Compounds 21a and 21b was isolated from the bis-ester Compound 21c in 37% yield by a consecutive column chromatography in a different eluent.

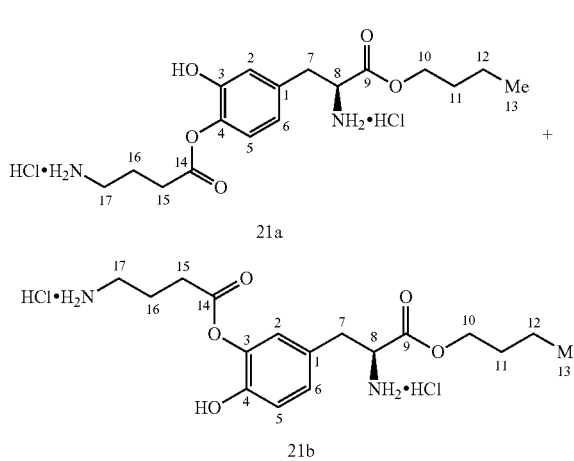

21a

21b

¹H NMR analysis of an aliquot in D$_2$O showed about 91% of the isomers mixture of Compounds 21a and 21b in an approximately 1.16:1 ratio, respectively (as presented hereinafter), along with about 4.5% L-DOPA butyl ester hydrochloride (Compound 14) and about 4.5% GABA.

The ratio of isomers was determined based on ¹H-NMR integrations of the H-2 in both isomers. Unless otherwise indicated, the chemical shifts are assigned to both isomers. Superscript notations $^{a/b}$ refer to nuclei assigned to the corresponding isomers in the mixture.

¹H NMR (300 MHz, D$_2$O) ppm: δ=0.87 (t, J=7.35 Hz, 5.6H, H-13), 1.23-1.33 (m, ~4H, H-12), 1.53-1.63 (m, 3.7H, H-11), 2.10 (quint, J=7.43 Hz, 3.7H, H-16), 2.85 (t, J=7.20 Hz, 3.7H, H-15), 3.14 (m, 3.7H, H-17), 3.24 (m, 3.7H, H-7), 4.22 (t, J=6.60 Hz, 1.7H, H-10$^b$), 4.23 (t, J=6.60 Hz, 2H, H-10$^a$), 4.37 (t, J=6.90 Hz, 0.9H, H-8$^b$), 4.41 (t, J=6.90 Hz, 1H, H-8$^a$), 6.88 (dd, J$_{ortho}$=8.10 Hz, J$_{meta}$=1.80 Hz, 1H, H-6$^a$), 6.94 (d, J$_{meta}$=1.80 Hz, 1H, H-2$^a$), 7.03 (d, J$_{meta}$=1.80 Hz, 0.9H, H-2$^b$), 7.05 (d, J$_{ortho}$=8.10 Hz, 1H, H-5$^a$), 7.11 (dd, J$_{ortho}$=8.10 Hz, J$_{meta}$=1.80 Hz, 0.9H, H-6$^b$), 7.13 (d, J$_{ortho}$=8.10 Hz, 0.9H, H-5$^b$).

¹³C NMR (75 MHz, D$_2$O) ppm: δ=13.50 (C-13), 19.05 (C-12), 22.63 (C-16), 30.31 (C-15), 31.02 (C-11), 35.45 (C-7$^b$), 35.97 (C-7$^a$), 54.64 (C-8$^a$), 54.72 (C-8$^b$), 67.90 (C-10), 118.41, 118.69, 122.45, 124.29 and 124.51 (Ar—CH), 127.08 (C-1$^{a\,or\,b}$), 129.37 (Ar—CH), 134.30 (C-1$^{a\,or\,b}$), 138.27 and 138.75 (C-4$^a$+C-3$^b$), 147.63 and 148.26 (C-3$^a$+C-4$^b$), 170.33 (C-9), 174.37 (C-14).

MS (CI+): m/z=337.172 ([M-H]$^{·+}$, 8.17), 254.142 ([ArCH$_2$CH(NH$_3$)CO$_2$Bu]$^{·+}$, 100.00), 86.053 ([NH$_2$(CH$_2$)$_3$CO]$^{·+}$, 42.65).

HRMS calcd. for C$_{17}$H$_{25}$N$_2$O$_5$ ([M—H]$^{·+}$, DCI, CH$_4$) 337.1763. found 539.1721.

Preparation of Benzenesulfonic Acid Addition Salts

The hydrochloride salts of Compounds 6, 8a, 11, 13, 14, 16, 18 and 21 were identified as hygroscopic. Hence, a corresponding benzenesulfonate addition salt (Compound 22) was prepared as illustrated in Scheme 10 as a model to evaluate its hygroscopicity. The basis for this assumption was that the addition salt of an aromatic acid would be less hygroscopic than that of the corresponding hydrochloric acid addition salt. Thus, the butyl ester, Compound 20 was Boc-deprotected with 3 equivalents of benzenesulfonic acid in 1,2-dichloromethane.

The isolated salt, Compound 22, was found to be much less hygroscopic than the hydrochloride salt.

Scheme 10

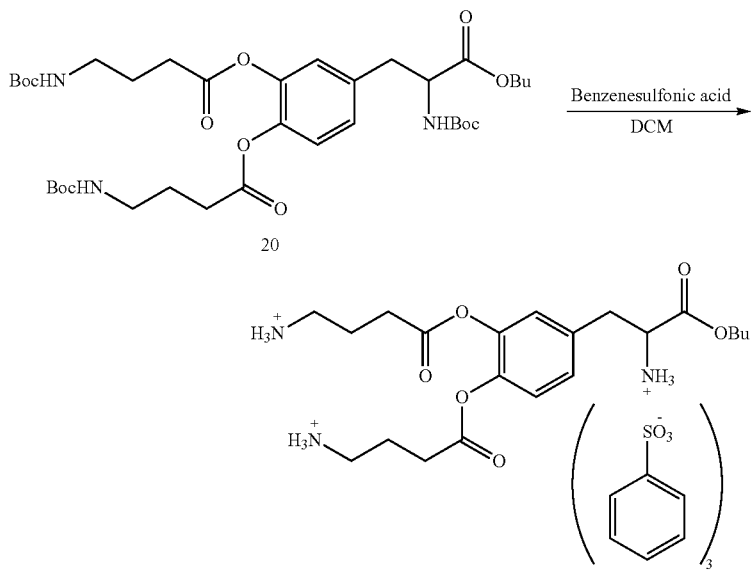

Butyl-2-amino-3-(3,4-phenyl-di[4-aminobutanoate])propanoate tri-benzenesulfonate salt (Compound 22) was prepared by adding benzenesulfonic acid (496 mg, 3.14 mmol) to a stirred solution of Compound 20 (751 mg, 1.04 mmol) in dry DCM (30 ml). After 4 hours water was added and the aqueous phase was separated, washed with DCM and evaporated to dryness. Recrystallization from MeOH:ether afforded Compound 22 as a brownish solid (707 mg, 76% yield).

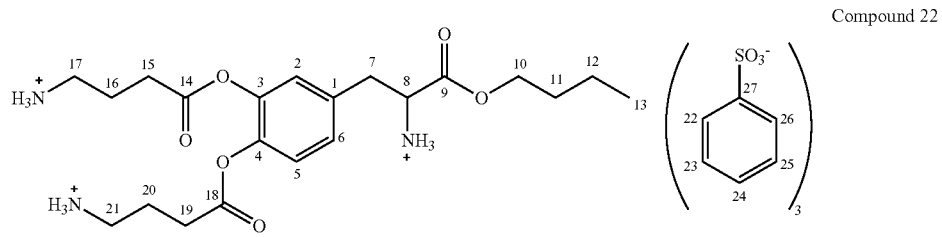

Compound 22

Melting point (mp): 128° C.;

$^1$H-NMR (300 MHz, $D_2O$) ppm: δ=7.81-7.77 (m, 6H, H-22+H-26), 7.57+7.47 (m, 9H, H-23+H-24+H-25), 7.26-7.14 (m, 3H, H-2+H-5+H-6), 4.35 (t, J=7.1 Hz, 1H, H-8), 4.14 (t, J=6.3 Hz, 2H, H-10), 3.24 (d, J=7.1 Hz, 1H, H-7), 3.02 (m, 4H, H-17+H-21), 2.73 (t, J=7.2 Hz, 3H, major rotamer, H-15+H-19), 2.47 (t, J=7.2 Hz, 1H, minor rotamer, H-15+H-19), 2.05-1.89 (m, 4H, H-16+H-21), 1.50 (m, 2H, H-11), 1.20 (m, 2H, H-12), 0.82 (t, J=7.5 Hz, 3H, H-13);

$^{13}$C-NMR (300 MHz, $D_2O$) ppm: δ=173.05 (2C, C-14+C-18), 169.93 (1C, C-9), 142.86 (3C, C-27), 141.99+141.43 (2C, C-3+C-4), 134.28 (1C, C-1), 132.10 (3C, C-24), 129.52 (6C, C-23+C-25), 129.06 (1C, C-6), 125.87 (6C, C-22+C-26), 124.96+124.70 (2C, C-3+C-4), 67.77 (1C, C-10), 54.32 (1C, C-8), 39.04 (2C, C-17+C-21), 35.56 (1C, C-7), 30.78 (2C, C-15+C-18), 30.13 (1C, C-11), 22.42 (2C, C-16+C-20), 18.93 (1C, C-12), 13.42 (1C, C-13);

HRMS analysis (DCI, $CH_4$): m/z for $C_{21}H_{33}N_3O_6$ (calculated=423.503): [MH$^+$]=422.231.

Preparation of L-DOPA-OCH$_2$O-GABA Derivative (Compound 33)

An alternative approach to couple GABA with L-DOPA, is by taking advantage of the carboxylic acid functionality of L-DOPA for the purpose of acylation, rather than its hydroxyls. While in the L-DOPA mono-GABA ester Compounds 21a and 21b the carboxylic acid moiety of L-DOPA was esterified with n-butanol to reduce the hydrophilicity, the acyloxymethyl derivative 33 (see, Scheme 11 below) encompasses the carboxylic moieties of L-DOPA and GABA attached via a labile —OCH$_2$O— linker. Linking L-DOPA and GABA via an oxyalkylester linkage, such as oxymethylester linkage, further advantageously provides conjugate that can release formaldehyde as an additional metabolite upon in vivo hydrolytic cleavage of the acyloxymethyl ester derivative, alongside of L-DOPA and GABA (see, Scheme 11). Formaldehyde was shown to exhibit beneficial therapeutic effect.

Scheme 11

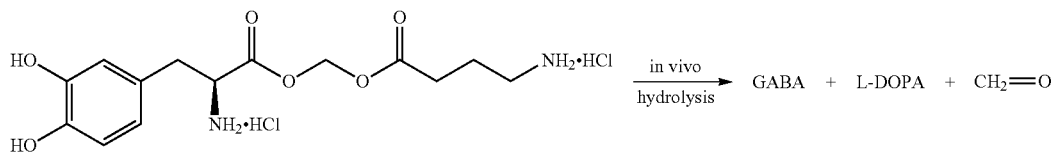

33

The following synthetic pathway for preparing Compound 33 was devised (see, Scheme 12 below), while taking into consideration the effect and removal selectivity of the selected protecting groups.

L-DOPA was converted into its corresponding alkyl ester, followed by Boc-protection of the amino moiety. Dibenzylation of the L-DOPA hydroxyls was thereafter efficiently accomplished, and was followed by hydrolysis of the alkyl ester so as to uncovers the free acid functionality. Base-mediated acyloxymethylation with N-Boc-GABA-OCH$_2$Cl was then performed, followed by deprotection of the L-DOPA and amino functions by hydrogenolysis and acidification, respectively, so as to afford the desired product.

Scheme 12

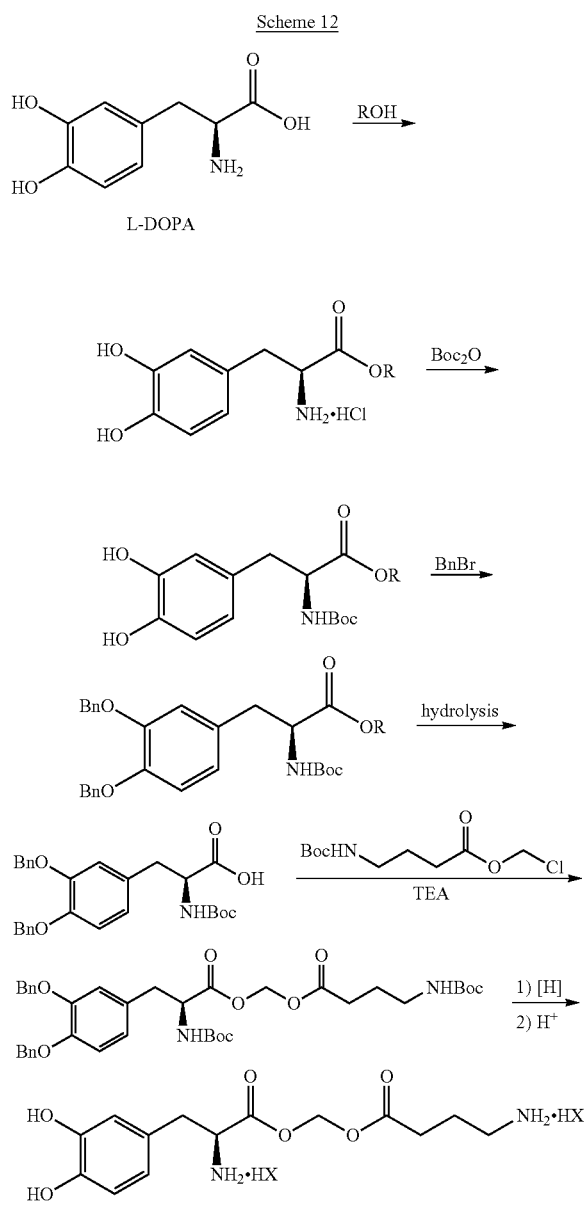

L-DOPA methyl ester hydrochloride (Compound 6) was prepared from L-DOPA using thionyl chloride in methanol. N-Boc-protection of Compound 6, employing di-tert-butyl dicarbonate in the presence of aqueous NaOH solution led to a mixture of Compound 26 and two N,O-Boc isomers Compounds 27a and 27b (see, Scheme 13), resulting from a further acylation of one of the L-DOPA hydroxyl groups. The N-Boc-protection of Compound 6 was performed as follows: To a solution of L-DOPA methyl ester (Compound 6, 1 equivalent) in dioxane and water (2:1 v/v) was added 1 M NaOH solution (1 equivalent). After 10 minutes, di-tert-butyl dicarbonate (1 equivalent) was added and the reaction was stirred at room temperature overnight. The solvent was thereafter evaporated and the residue was diluted with water and EtOAc. The layers were separated and the organic layer was washed with 1 M KHSO$_4$ (×3), 1 M NaHCO$_3$ (×3) and brine (×3), dried over Na$_2$SO$_4$ and evaporated to give the crude product Compound 26 and the two N,O-Boc isomers Compounds 27a and 27b. The crude product was chromatographed (using hexane:EtOAc 2:1 v/v as eluent, R$_f$=0.12), to remove the isomeric N,O-Boc-protected by-products, giving Compound 26 as a white solid (30% yield).

An alternative synthesis method for obtaining Compound 26 was also successfully performed. To a solution of Compound 6 (4.00 grams, 16.15 mmol) in water (35 ml) were added NaHCO$_3$ (2.71 grams, 32.30 mmol). After a few minutes, a solution of di-tert-butyl dicarbonate (3.52 grams, 16.15 mmol) in THF (36 ml) was added. The mixture was stirred at room temperature for 19 hours, and thereafter concentrate under vacuum to remove THF. Water and EtOAc were added and the layers were separated. The organic phase was washed with 1 N HCl (×2) and water (×2), dried over Na$_2$SO$_4$ and evaporated to give the crude product (4.58 grams), of which 1.86 grams were purified by chromatography (using hexane:EtOAc 2:1 v/v as eluent) to give Compound 26 as a white solid (1.29 gram, 69% chromatographic yield).

Compound 26

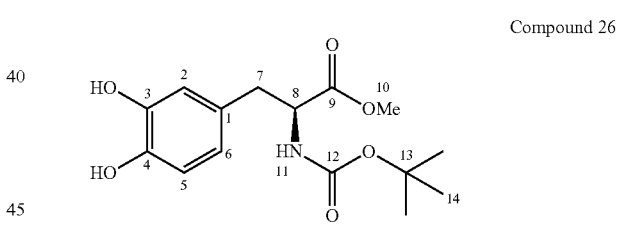

$^1$H NMR (300 MHz, CDCl$_3$) ppm: δ=1.36 (s, 9H, H-14), 2.78-2.96 (m [AB of ABX system], 2H, H-7), 3.64 (s, 3H, H-10), 4.46 (m [X of ABX system], 1H, H-8), 5.22 (br d, J=8.40 Hz, 1H, H-11), 6.65 (br dd, J$_{ortho}$=8.10 Hz, 1H, H-6), 6.75 (br d, 1H, H-2), 6.87 (d, J$_{ortho}$=8.10 Hz, 1H, H-5), 6.98 (br s, 2H, 3-OH+4-OH);

$^{13}$C NMR (75 MHz, CDCl$_3$) ppm: δ=28.25 (C-14), 37.58 (C-7), 52.35 (C-10), 54.72 (C-8), 80.51 (C-13), 115.38 and 116.17 (C-2+C-5), 122.24 (C-6), 127.94 (C-1), 143.32 and 144.22 (C-3+C-4), 155.76 (C-12), 172.90 (C-9);

MS (CI+): m/z=312.143 ([MH]$^{•+}$, 55.43), 256.069 ([MH—C$_4$H$_8$]$^{•+}$, 73.31), 212.093 ([MH—C$_5$H$_8$O$_2$]$^{•+}$, 100.00);

HRMS calcd. for C$_{15}$H$_{22}$NO$_6$ ([MH]$^{•+}$, DCI, CH$_4$) 312.1447. found 312.1431.

Reagents and conditions: (a) SOCl$_2$, MeOH, 0° C. to rt; (b) Boc$_2$O, 1 M NaOH, H$_2$O/dioxane, rt; (c) Boc$_2$O, NaHCO$_3$, H$_2$O/THF, rt.

Scheme 13

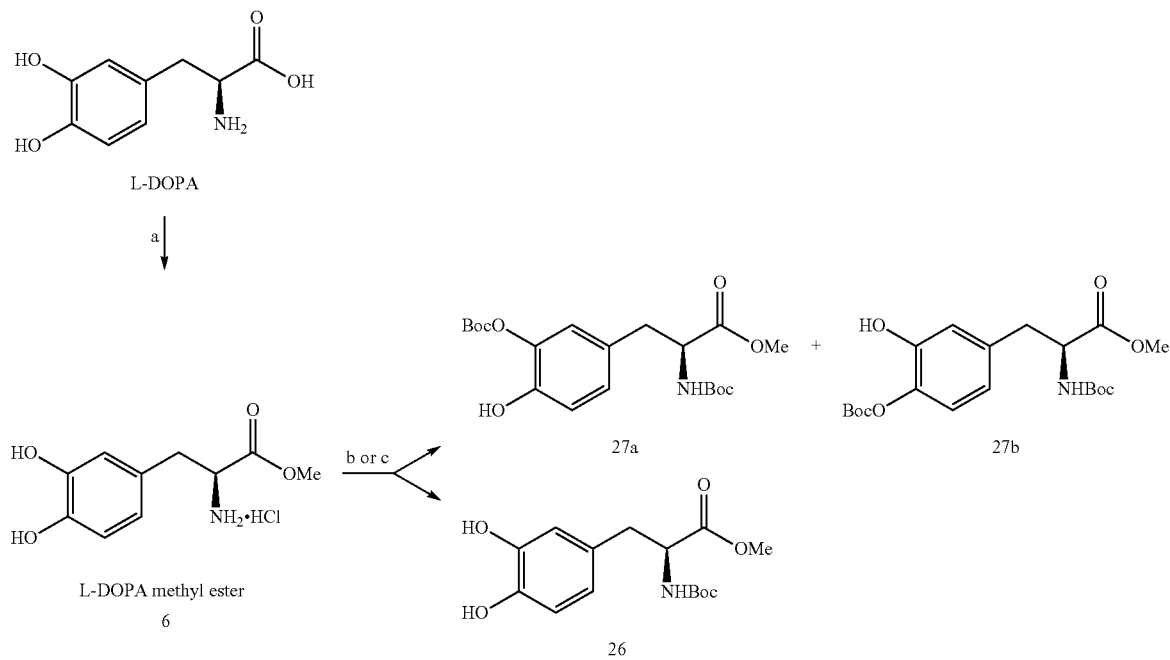

Reagents and conditions: (a) SOCl₂, MeOH, 0° C. to rt; (b) Boc₂O, 1M NaOH, H₂O/dioxane, rt; (c) Boc₂O, NaHCO₃, H₂O/THF, rt.

Replacement of NaOH by NaHCO₃ (see, b or c in Scheme 13) resulted in a fewer amount of side-products, so that the crude product consisted almost exclusively of the N-protected Compound 26. The variation in product distribution reflects the competition between N- and O-acylation, as derived from the relative proximity of the acidity constants predicted for the ammonium and first phenolic ionizations (it is noted that L-DOPA exhibits two overlapping acidity constants at 0.16 ionic strength and 25° C.: $pK_{OH}$=8.97, $pK_{NH3}$=9.42). However, the base strength seems to play a significant role in the product distribution: in a weak basic medium (NaHCO₃) the N-Boc product predominates, whereas in a strong alkaline medium (NaOH) the formation of a phenolate anion becomes more favorable, hence leading to the N,O-Boc product. In any case, the amino group takes precedence over the phenolate regarding tert-butoxycarbonylation, due to its better nucleophilicity.

Subsequently, the N-Boc-L-DOPA methyl ester, Compound 26, was treated with K₂CO₃, NaI, an excess of benzyl bromide and a catalytic amount of n-Bu₄N⁺Br⁻ under reflux to afford Compound 28 (see, scheme 14 below).

Scheme 14

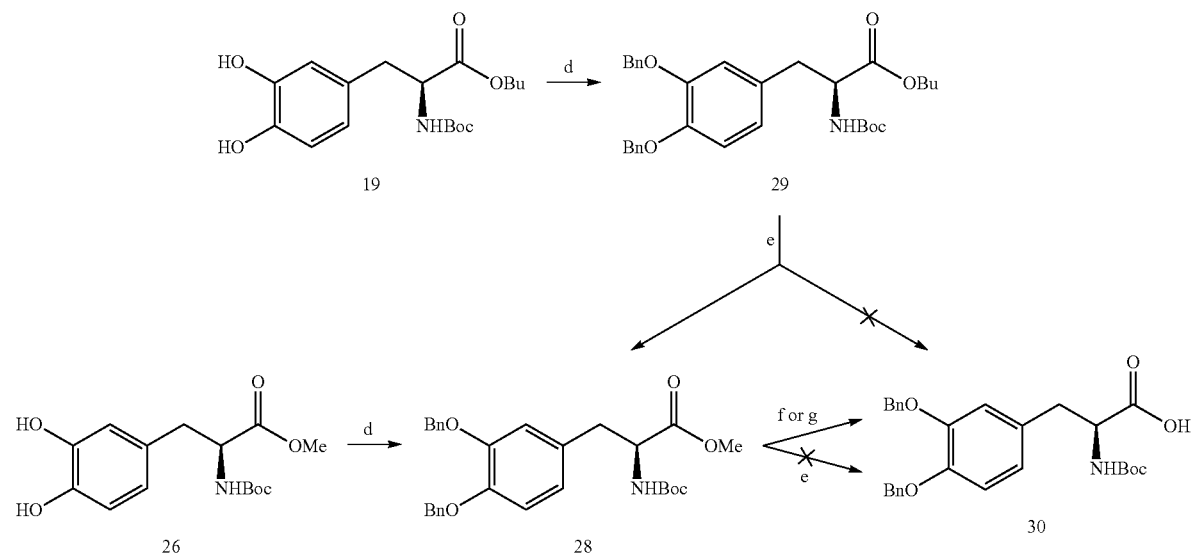

Reagents and conditions: (d) BnBr, K₂CO₃, NaI, n-Bu₄N⁺Br⁻ (cat.), acetone, reflux; (e) 1M NaOH, THF/MeOH, rt; (f) 1M LiOH, THF/H₂O, rt; (g) K₂CO₃, H₂O/MeOH, rt.

The dibenzylation of Compound 26 was successfully performed as follows: To a solution of N-Boc-L-DOPA methyl ester (Compound 26, 1 equivalent) in dry acetone under $N_2$ atmosphere were added $K_2CO_3$ (2.2 equivalents), NaI (0.2 equivalents), n-$Bu_4N^+Br^-$ (0.2 equivalents) and benzyl bromide (3 equivalents). The reaction mixture was refluxed for 4 hours and thereafter evaporated under vacuum. Dichloromethane (DCM) and water were added, the layers separated and the aqueous phase was washed to with DCM (×2). The combined organic layer was washed with water (×2), dried over $Na_2SO_4$ and evaporated to give the crude product Compound 28.

Compound 28

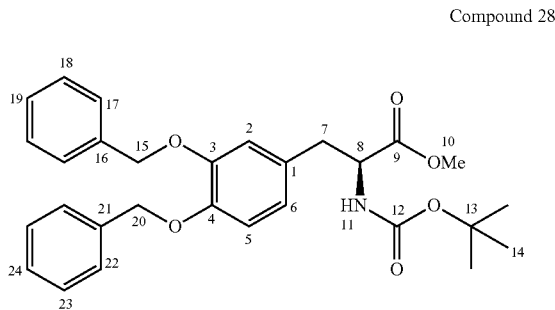 [SMILES: COC(=O)[C@H](Cc1ccc(OCc2ccccc2)c(OCc2ccccc2)c1)NC(=O)OC(C)(C)C]

The crude product was purified by column chromatography (using hexane:EtOAc 4:1 v/v as eluent, $R_f$=0.20) to afford the desired Compound 28 as a white solid (72% yield).

Melting point (mp): 102-105° C. [lit.[4] mp 112° C.].

$^1$H NMR (300 MHz, $CDCl_3$) ppm: δ=1.44 (s, 9H, H-14), 2.93-3.05 (m [AB of ABX system], 2H, H-7), 3.65 (s, 3H, H-10), 4.54 (m [X of ABX system], 1H, H-8), 4.98 (br d, J=8.10 Hz, 1H, H-11), 5.13 (s, 4H, H-15+H-20), 6.65 (dd, $J_{ortho}$=8.10 Hz, $J_{meta}$=1.80 Hz, 1H, H-6), 6.75 (d, $J_{meta}$=2.10 Hz, 1H, H-2), 6.87 (d, $J_{ortho}$=8.10 Hz, 1H, H-5), 7.29-7.47 (m, 10H, H-17+H-18+H-19+H-22+H-23+H-24);

$^{13}$C NMR (75 MHz, $CDCl_3$) ppm: δ=28.42 (C-14), 37.88 (C-7), 52.24 (C-10), 54.52 (C-8), 71.44 (C-15+C-20), 80.02 (C-13), 115.23 and 116.31 (C-2+C-5), 122.40 (C-6), 127.37, 127.43, 127.86, 127.92, 128.55 and 128.58 (C-17+C-18+C-19+C-22+C-23+C-24), 129.35 (C-1), 137.29 and 137.40 (C-16+C-21), 148.21 and 149.01 (C-3+C-4), 155.17 (C-12), 172.43 (C-9);

MS (CI+): m/z=491.230 ([M]$^{•+}$, 11.02), 392.176 ([MH—$C_5H_8O_2$]$^{•+}$, 22.28);

HRMS calcd. for $C_{29}H_{33}NO_6$ ([M]$^{•+}$, DCI, $CH_4$) 491.2308. found 491.2351.

Dibenzylated N-Boc-L-DOPA butyl ester, Compound 29, was prepared from Compound 19, similarly to the methyl ester analog, and was subjected to saponification under the same conditions, but also afforded the methyl ester Compound 28.

Compound 29

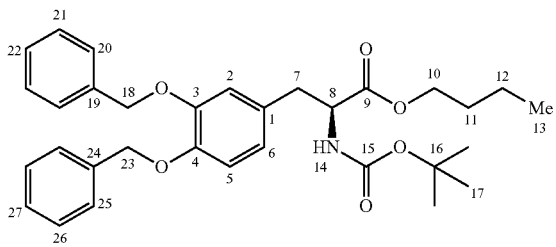

The crude product was chromatographed (using hexane:EtOAc 4:1 v/v as eluent, $R_f$=0.32) to give Compound 29 as a white solid (63% yield).

Melting point (mp): 96-98° C.

$^1$H NMR (300 MHz, $CDCl_3$) ppm: δ=0.91 (t, J=7.35 Hz, 3H, H-13), 1.24-1.38 (m, 2H, H-12), 1.42 (s, 9H, H-17), 1.46-1.65 (m, 2H, H-11), 2.99 (d, J=5.40 Hz, 2H, H-7), 3.96-4.12 (m, 2H, H-10), 4.44-4.58 (m [X of ABX system], 1H, H-8), 4.95 (br d, J=12.00 Hz, 1H, H-14), 5.12 (s, 4H, H-18+H-23), 6.65 (dd, $J_{ortho}$=8.10 Hz, $J_{meta}$=1.80 Hz, 1H, H-6), 6.75 (d, $J_{meta}$=1.80 Hz, 1H, H-2), 6.86 (d, $J_{ortho}$=8.10 Hz, 1H, H-5), 7.26-7.46 (m, 10H, H-20+H-21+H-22+H-25+H-26+H-27);

$^{13}$C NMR (75 MHz, $CDCl_3$) ppm: δ=13.81 (C-13), 19.19 (C-12), 28.47 (C-17), 30.66 (C-11), 38.01 (C-7), 54.60 (C-8), 65.32 (C-10), 71.52 (C-18+C-23), 80.00 (C-16), 115.29 and 116.43 (C-2+C-5), 122.51 (C-6), 127.40, 127.50, 127.90, 127.95 and 128.61 (C-20+C-21+C-22+C-25+C-26+C-27), 129.53 (C-1), 137.34 and 137.49 (C-19+C-24), 148.28 and 149.09 (C-3+C-4), 155.23 (C-15), 172.12 (C-9);

MS (CI+): m/z=533.277 ([M]$^{•+}$, 4.06), 478.591 ([MH—$C_4H_8$]$^{•+}$, 2.61), 434.267 ([MH—$C_5H_8O_2$]$^{•+}$, 14.19), 91.129 ([$C_7H_7$]$^{•+}$, 100.00);

HRMS calcd. for $C_{32}H_{39}NO_6$ ([M]$^{•+}$, DCI, $CH_4$) 533.2777. found 533.2772.

Anal. calcd for $C_{32}H_{39}NO_6$: C, 72.02; H, 7.37; N, 2.62. Found: C, 71.48; H, 7.46; N, 2.17.

Compound 30 was obtained from Compound 28 as follows: To a solution of Compound 28 (0.23 gram, 0.47 mmol) in 5.29 ml THF and 3.30 ml water was added 1 N LiOH solution (0.55 ml, 0.55 mmol) at 0° C. The solution color turned immediately into yellow, and the solution was allowed to warm to room temperature and stirred for 7.5 hours. Monitoring the reaction Using TLC (hexane:EtOAc 2:1 v/v as eluent) indicated a presence of the starting material Compound 28, and therefore additional 0.55 ml of 1 N LiOH solution were added, and the solution was further stirred at room temperature overnight. Upon reaction completion, as indicated by TLC analysis, the solution was concentrated under vacuum to remove THF. The residue was acidified with 1 M $KHSO_4$ solution to obtain pH of about 1 and the solution was extracted with EtOAc (×3). The organic layer was washed with brine (×3), dried over $Na_2SO_4$, filtered and evaporated to afford Compound 30 as a white solid (0.17 gram, 76% yield).

Since the strongly basic medium could possibly give rise to epimerization at the α-carbon (resulting in racemization), the optical activity of Compound 30 was determined and found to be dextrorotatory with specific rotation of $[α]_D^{24}$=+12.0 (c 0.0057, MeOH), in good accordance with the value reported in literature.

In an alternative synthetic pathway, $K_2CO_3$ in $H_2O$—MeOH solution was used as follows: $K_2CO_3$ (0.88 gram, 6.40 mmol) was added to a solution of Compound 28 (0.90 gram, 1.83 mmol) in 28.73 ml MeOH and 3.93 ml water. The suspension was stirred at room temperature overnight. Water was thereafter added, and the aqueous solution was acidified with 1 M $KHSO_4$ solution until a pH of about 2 was obtained and was thereafter extracted with DCM. The organic phase was washed with brine, dried over $Na_2SO_4$, filtered and evaporated to give Compound 30 as a white solid (0.85 gram, 97% yield).

Compound 30

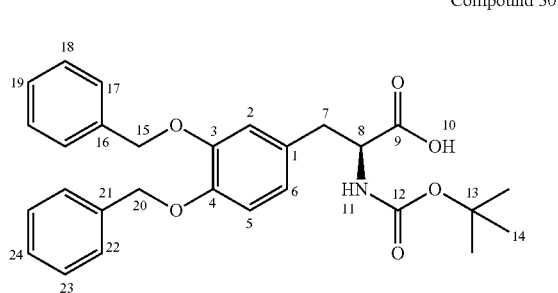

¹H NMR (300 MHz, CDCl₃) ppm: δ=1.43 (s, 9H, H-14), 2.96 (dd, ²J$_{H-7,H-7'}$=13.80 Hz, ³J$_{H-7\ or\ H-7',H-8}$=6.30 Hz, 1H, H-7 or H-7'), 3.08 (dd, ²J$_{H-7,H-7'}$=13.80 Hz, ³J$_{H-7\ or\ H-7',H-8}$=4.80 Hz, 1H, H-7 or H-7'), 4.55 (m [X of ABX system], 1H, H-8), 4.94 (br d, J=7.50 Hz, 1H, H-11), 5.11 (two overlapping singlets, 4H, H-15+H-20), 6.69 (br dd, 1H, H-6), 6.80 (br d, 1H, H-2), 6.85 (d, J$_{ortho}$=8.40 Hz, 1H, H-5), 7.27-7.45 (m, 10H, H-17+H-18+H-19+H-22+H-23+H-24);

¹³C NMR (75 MHz, CDCl₃) ppm: δ=28.43 (C-14), 37.35 (C-7), 54.41 (C-8), 71.46 (C-15+C-20), 80.43 (C-13), 115.27 and 116.46 (C-2+C-5), 122.51 (C-6), 127.41, 127.55, 127.89, 127.93, 128.58 and 128.60 (C-17+C-18+C-19+C-22+C-23+C-24), 129.08 (C-1), 137.33 and 137.42 (C-16+C-21), 148.27 and 149.00 (C-3+C-4), 155.54 (C-12), 176.19 (C-9);

The TEA salt of the obtained acid, Compound 30, was then alkylated with N-Boc-GABA-OCH₂Cl, Compound 23, in DMF, under heat, to afford the acyloxymethyl ester Compound 31 in 45% yield after purification by flash chromatography (see, Scheme 15 below).

ture for 18 hours. Subsequently, water was added to the mixture, the layers were separated and the aqueous phase was washed with DCM (×3). The combined organic layer was washed with 5% NaHCO₃ (×3) and brine (×3), dried over Na₂SO₄, filtered and evaporated. The crude product was purified by flash chromatography (using hexane:EtOAc 5:1 v/v as eluent, R$_f$=0.21) to afford Compound 23 as a colorless oil (59% yield).

¹H NMR (300 MHz, CDCl₃) ppm: δ=1.45 (s, 9H, Me₃C), 1.86 (quint, J=7.05 Hz, 2H, CH₂CH₂CH₂), 2.47 (t, J=7.35 Hz, 2H, CH₂CO₂), 3.18 (br t, J=6.75 Hz, 2H, CH₂NH), 5.73 (br s, 1H, NH), 5.55 (s, 2H, OCH₂Cl);

¹³C NMR (75 MHz, CDCl₃) ppm: δ=24.73 (CH₂CH₂CH₂), 28.13 (Me₃C), 30.93 (CH₂CO₂), 39.39 (CH₂NH), 68.46 (OCH₂Cl), 78.81 (CMe₃), 155.92 (NHCO₂), 171.12 (CO₂CH₂);

MS (CI+): m/z=252.102, 254.099 ([MH]$^{•+}$, 33.13, 11.24), 196.019, 198.019 ([MH—C₄H₈]$^{•+}$, 100.00, 32.35), 152.005, 154.002 ([MH—C₅H₈O₂]$^{•+}$, 54.07, 16.69), 130.052 ([C₆H₁₂NO₂]$^{•+}$, 43.31);

HRMS calcd. for C₁₀H₁₉ClNO₄ ([MH]$^{•+}$, DCI, CH₄) 252.1003, 254.0973. found

Conjugation of Compound 30 and Compound 23 to thereby obtain Compound 31 was successfully performed as follows: To a solution of Compound 30 (124 mg, 0.26 mmol) and Compound 23 (55 mg, 0.22 mmol) in DMF, under N₂ atmosphere, was added TEA (0.1 ml, 0.72 mmol). The mixture was stirred and heated at about 70° C. for 4.5 hours. Upon reaction completion, as monitored by TLC, as complete consumption of Compound 23, the solvent was evaporated to remove DMF, and the residue was taken up in EtOAc. The Scheme 15

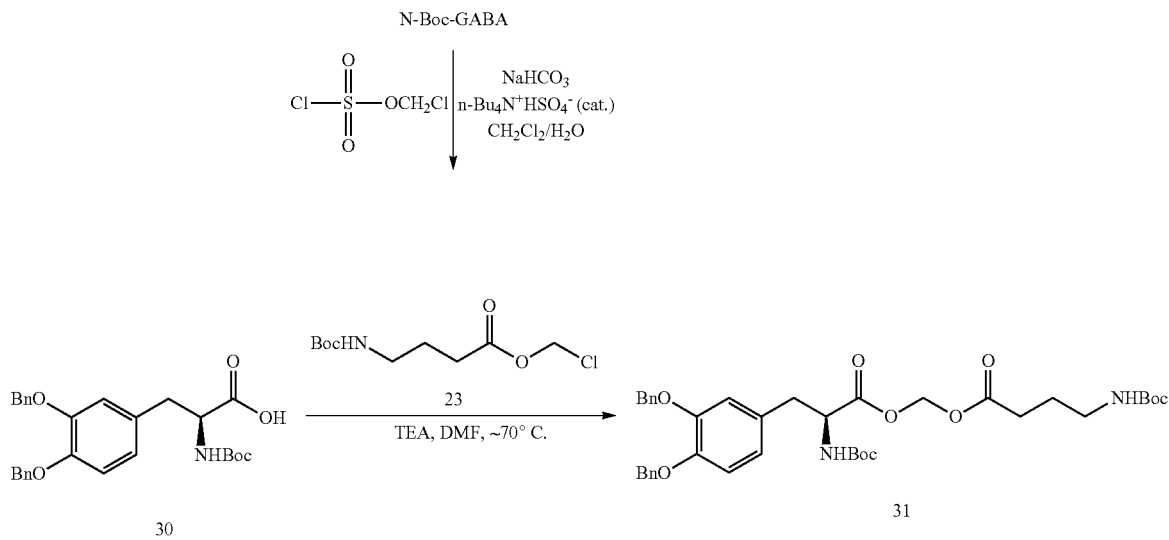

Compound 23 was prepared from N-Boc-GABA as follows: To a solution of N-Boc-GABA (1 equivalent) in water/DCM (1:1 v/v) were added NaHCO₃ (4 equivalents), chloromethyl chlorosulfate (1.2 equivalent) and n-Bu₄N⁺HSO₄⁻ (catalytic amount). The mixture was stirred at room temperaorganic phase was washed with 5% NaHCO₃ (×3) and brine (×3), dried over Na₂SO₄, filtered and evaporated to give the crude product. Column chromatography (using hexane:EtOAc 3:1 v/v as eluent) afforded Compound 31 as a white solid (68 mg, 45% yield).

Compound 31

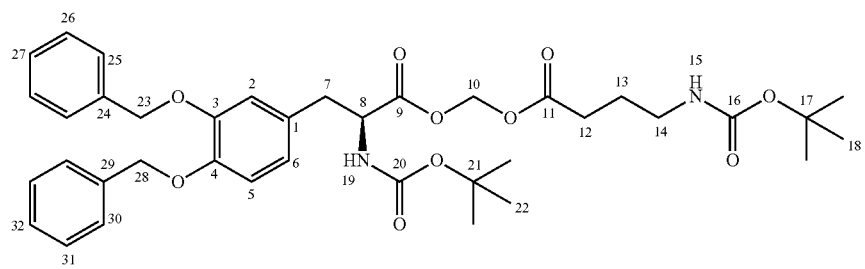

$^1$H NMR (300 MHz, CDCl$_3$) ppm: δ=1.42 and 1.43 (two singlets, 18H, H-18+H-22), 1.79 (quint, J=6.98 Hz, 2H, H-13), 2.38 (t, J=7.20 Hz, 2H, H-12), 2.91-3.07 (m [AB of ABX system], 2H, H-7), 3.12 (br q, J=6.00 Hz, 2H, H-14), 4.54 (br q, J=6.90 Hz, 1H, H-8), 4.72 (br s, 1H, H-15), 4.96 (br d, J=6.60 Hz, 1H, H-19), 5.13 (s, 4H, H-23+H-28), 5.68 (d, J=5.40 Hz, 1H, H-10), 5.75 (d, J=5.40 Hz, 1H, H-10'), 6.66 (dd, J$_{ortho}$=8.10 Hz, J$_{meta}$=1.80 Hz, 1H, H-6), 6.76 (d, J$_{meta}$=1.80 Hz, 1H, H-2), 6.86 (d, J$_{ortho}$=8.10 Hz, 1H, H-5), 7.28-7.45 (m, 10H, H-25+H-26+H-27+H-30+H-31+H-32);

$^{13}$C NMR (75 MHz, CDCl$_3$) ppm: δ=25.07 (C-13), 28.40 and 28.50 (C-18+C-22), 31.17 (C-12), 37.34 (C-7), 39.71 (C-14), 54.37 (C-8), 71.43 and 71.53 (C-23+C-28), 79.69 (C-10), 80.256 (C-17+C-21), 115.30 and 116.47 (C-2+C-5), 122.49 (C-6), 127.39, 127.48, 127.91, 127.96, 128.59 and 128.59 (two overlapping signals, C-25+C-26+C-27+C-30+C-31+C-32), 128.91 (C-1), 137.26 and 137.35 (C-24+C-29), 148.36 and 149.06 (C-3+C-4), 155.19 and 156.08 (C-16+C-20), 170.94 and 171.83 (C-9+C-11);

MS (CI+): m/z=692.331 ([M]$^{·+}$, 32.03), 593.419 ([MH—C$_5$H$_8$O$_2$]$^{·+}$, 100.00), 537.385 ([MH—C$_5$H$_8$O$_2$—C$_4$H$_8$]$^{·+}$, 53.81), 493.369 ([MH—C$_5$H$_8$O$_2$—C$_5$H$_8$O$_2$]$^{·+}$, 20.75);

HRMS calcd. for C$_{38}$H$_{48}$N$_2$O$_{10}$ ([M]$^{·+}$, DCI, CH$_4$) 692.3309. found 692.3315.

The final stage required removal of the hydroxy and amino protecting groups, as depicted in Scheme 16 below.

Scheme 16

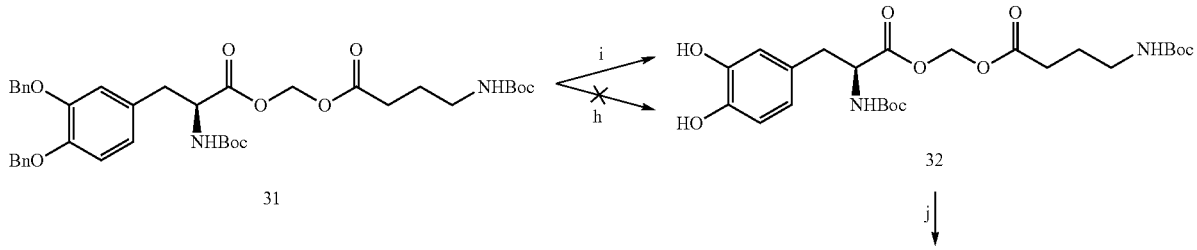

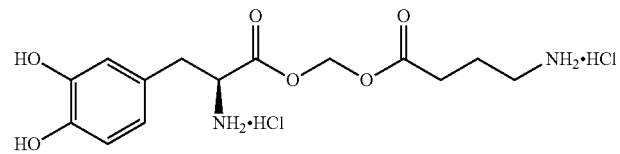

Reagents and conditions: (h) HCO$_2^-$NH$_4^+$, 10% Pd/C, EtOH, reflux; (i) 50 psi H$_2$, 10% Pd/C, MeOH, 2.5 h, rt; (j) 4N HCl/EtOAc, rt.

Hydrogenolysis using 10% Pd catalyst in a Parr shaker apparatus at 50 psi and room temperature furnished the free Compound 32 within 2.5 hours. Thus, hydrogenolysis was successfully performed as follows: To a solution of Compound 31 (99 mg, 0.14 mmol) in MeOH was added 10% Pd/C (10 mg). The suspension was then hydrogenated in a Parr apparatus under 50 psi of $H_2$ for 2.5 hours. The obtained mixture was filtered and evaporated, to give the desired product as a yellowish oil (60 mg, 82% yield). The compound was used in the next step without further purification.

Compound 32

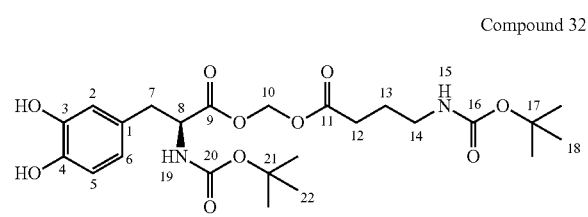 [SMILES: CC(C)(C)OC(=O)NCCCC(=O)OCOC(=O)[C@H](Cc1ccc(O)c(O)c1)NC(=O)OC(C)(C)C]

$^1$H NMR (300 MHz, CDCl$_3$) ppm: δ=1.42 and 1.43 (two singlets, 18H, H-18+H-22), 1.79 (quint, J=6.98 Hz, 2H, H-13), 2.38 (t, J=7.20 Hz, 2H, H-12), 2.91-3.07 (m [AB of ABX system], 2H, H-7), 3.12 (br q, J=6.00 Hz, 2H, H-14), 4.54 (br q, J=6.90 Hz, 1H, H-8), 4.72 (br s, 1H, H-15), 4.96 (br d, J=6.60 Hz, 1H, H-19), 5.13 (s, 4H, H-23+H-28), 5.68 (d, J=5.40 Hz, 1H, H-10), 5.75 (d, J=5.40 Hz, 1H, H-10'), 6.66 (dd, J$_{ortho}$=8.10 Hz, J$_{meta}$=1.80 Hz, 1H, H-6), 6.76 (d, J$_{meta}$=1.80 Hz, 1H, H-2), 6.86 (d, J$_{ortho}$=8.10 Hz, 1H, H-5), 7.28-7.45 (m, 10H, H-25+H-26+H-27+H-30+H-31+H-32);

$^{13}$C NMR (75 MHz, CDCl$_3$) ppm: δ=25.02 (C-13), 28.39 and 28.50 (C-18+C-22), 31.15 (C-12), 37.40 (C-7), 39.89 (C-14), 54.44 (C-8)$^1$, 79.64 (C-10), 80.14 and 80.50 (C-17+C-21), 115.42 and 116.38 (C-2+C-5), 121.44 (C-6), 127.50 (C-1), 14$^2$3.56 and 144.46 (C-3+C-4), 155.46 and 156.72 (C-16+C-20), 171.12 and 171.92 (C-9+C-11).

The two N-Boc moieties were deprotected as follows: To an ice-cold solution of Compound 32 in EtOAc a freshly prepared solution of 4 N HCl in EtOAc was added (obtained by addition of a known amount of acetyl chloride to an ice-cold solution of an equivalent amount of EtOH in EtOAc). The ice bath was removed after 1 hour, and the solution was allowed to warm to room temperature. After TLC analysis had shown complete consumption of the Boc-protected Compound 32, the solvent was evaporated to give the desired Compound 33 as a dihydrochloride salt in a quantitative yield.

Compound 33

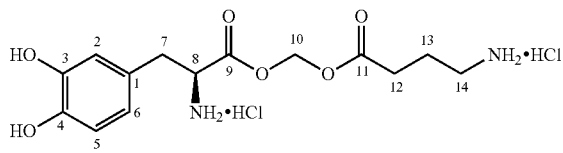

$^1$H NMR (200 MHz, CD$_3$OD) ppm: δ=0.91 (t, 3H, J=7.20 Hz, H-13), 1.32 (m, 2H, H-12), 1.62 (m, 2H, H-11), 1.97 (quint, J=7.50 Hz, 2H, H-13), 2.57 (t, J=7.10 Hz, 2H, H-12), 3.01 (t, J=7.70 Hz, 2H, H-14), 3.09 (d, J=6.40 Hz, 2H, H-7), 4.32 (t, J=6.60 Hz, 1H, H-8), 5.80 (d, J=5.80 Hz, 1H, H-10), 5.89 (d, J=5.80 Hz, 1H, H-10'), 6.59 (dd, J$_{ortho}$=8.00 Hz, J$_{meta}$=2.00 Hz, 1H, H-6), 6.70 (d, J$_{meta}$=2.00 Hz, 1H, H-2), 6.76 (d, J$_{ortho}$=8.00 Hz, 1H, H-5);

$^{13}$C NMR (50 MHz, CD$_3$OD) ppm: δ=23.27 (C-13), 31.17 (C-12), 36.50 (C-7), 39.86 (C-14), 55.11 (C-8), 81.21 (C-10), 116.79 and 117.40 (C-2+C-5), 121.94 (C-6), 125.93 (C-1), 146.07 and 146.65 (C-3+C-4), 169.16 and 172.36 (C-9+C-11).

Example 2

Effect of L-DOPA-GABA Conjugate (BL-1023; Compound 5) on MPTP-Induced Parkinson's Disease Model in Mice Parkinson's disease (PD) is a neurodegenerative disorder characterized by reduction in striatal dopamine (DA) content caused by the loss of dopaminergic neurons in the Substantia Nigra pars compacta (SNpc) and their projections to the striatum. MPTP is an effective dopaminergic neurotoxin in mouse. MPTP administration lead to bilateral marked loss of Tyrosin-Hydroxilase (TH) immunoreactive cell bodies in the SNpc.

Materials:

BL-1023 conjugate was synthesized as described in Example 1 hereinabove and was dissolved in saline to achieve equimolar doses of 20 mg/kg and 40 mg/kg L-DOPA. The solutions were freshly prepared prior to administration.

L-DOPA (Sigma Cat. No. D9628) was dissolved in saline to achieve a concentration of doses of 20 mg/kg and 40 mg/kg. The doses were freshly prepared prior to administration.

Solution of 1-Methyl-4-phenyl-1,2,3,6-tetrahydropyridine hydrochloride (MPTP; Sigma (Cat. No. M0896) was freshly prepared prior to each injection session by dissolving the lyophilized powder in saline to achieve a final injected concentration of 4 mg/ml, appropriate for the selected dose of 20 mg/kg and dose volume of 5 ml/kg.

Rabbit antibody against Tyrosine Hydroxylase (TH) was purchased from Calbiochem and was stored at −80° C. following receipt until being used.

Gout anti Rabbit antibody was purchased from Pharmatraide and was stored at −80° C. following receipt until being used.

Assay Protocol:

Young adult (7-8 weeks old) male mice strain C57/bl were acclimated for one week prior to MPTP initiation. During acclimation and throughout the entire study duration, animals were housed within a limited access rodent facility and kept in groups of maximum 5 mice in polypropylene cages (23×17×14 cm), fitted with solid bottoms and filled with wood shavings as bedding material. Animals were provided ad libitum a commercial rodent diet and free access to drinking water, supplied to each cage via polyethylene bottles with stainless steel sipper tubes.

Automatically controlled environmental conditions were set to maintain temperature at 20-24° C. with a relative humidity (RH) of 30-70%, a 12:12 hour light:dark cycle and 15-30 air changes per hour in the study room.

Animals were given a unique animal identification tail mark. This number also appears on a cage card, visible on the front of each cage. The cage card also contained the study and group numbers, route of administration, gender, strain and all other details relevant to the treatment group. During the acclimation period, animals were randomly assigned to experimental groups.

Mice were administered IP with 4 injections of MPTP (each injection contained 20 mg/kg, 5 ml/kg) in saline or saline alone (control) at 2 hours interval on day 0. Mice were then grouped as described in Table 3 below and were administered subcutaneously (cuss.) with test solutions by once daily repeated dosing sessions throughout 8 successive treatment days (Days 0-7), as illustrated in FIG. 1.

TABLE 3

| Test Material | Group size | Route | Dose Level (mg/kg/admin) | Volume dosage (ml/kg) | Regime |
|---|---|---|---|---|---|
| Naïve | N = 3 | | | | |
| Vehicle control | n = 10 | S.C | 0 | 20 | Once daily from day 0 |
| Positive Control L-DOPA (40 mg/kg) | n = 10 | S.C | 40 mg/kg | 20 | Once daily from day 0 |
| BL-1023 equimolar to 40 mg/kg | n = 10 | S.C | equimolar to 40 mg/kg L-DOPA | 20 | Once daily from day 0 |

Seven days following MPTP administration animals are euthanized and their brains were removed for immunohistochemistry analysis of IR TH cells at the level of the SNpc.

Brains are fixed by cardiac perfusion with 4% Paraformaldehyde followed by fixation by immersion with the same fixative for at least 72 hours. Brains were then washed with PBS and transferred to 30% sucrose in PBS until they sank. Brains were then frozen using the craryostat special fast freezing (−60° C.). Brains were then crayosectioned (20 µm) at the level of the striatum and at the level of the substantia nigra (SN).

Immunohistochemistry staining was performed using Rabbit anti tyrosin hydroxylase (1:100). Slides were stained using DAB detection kit (Pharmatraide). Quantitative analysis was effected by counting of immunoreactive cells at the widest dimension of the SNpc lateral to the roots of the third cranial nerve separating medial and lateral SNpc at the level of interpreduncular nucleus.

Results:

As can be seen in Table 4 below, the number of TH immunoreactive cell bodies in the Substantia Nigra pars compacta (SNpc) of mice which were treated with BL-1023, was 41.0% higher than in the SNpc of mice treated with L-DOPA and 77.4% higher than in the SNpc of vehicle treated (control) mice.

Without being bound to any particular theory, it is suggested that the higher efficiency of BL-1023, as compared with an equimolar dose of L-DOPA, may be attributed to higher amount of available dopamine in the SNpc. Since L-DOPA is partially metabolized to dopamine in peripheral tissues by aromatic-L-amino-acid decarboxylase, and since dopamine per se is incapable of crossing the blood-brain barrier (BBB), the amount of dopamine eventually reaching the SNpc is substantially diminished. On the other hand, since BL-1023 is likely not metabolized by aromatic-L-amino-acid decarboxylase until after crossing the BBB, the amount of dopamine reaching the SNpc via systemic administration of BL-1023 is substantially higher.

Hence, these results clearly indicate that systemically administered BL-1023 is substantially more effective than L-DOPA in protecting against the loss of dopaminergic neurons in the Substantia Nigra pars compacta of Parkinson's model animals.

TABLE 4

| Treatment | Number of TH Cells | Standard Error |
|---|---|---|
| Naïve | 101 | 8 |
| Vehicle control | 31 | 16 |
| L-DOPA (40 mg/kg) | 39 | 10 |
| BL-1023 (equimolar to 40 mg/kg L-DOPA) | 55 | 4 |

Example 3

Effect of L-DOPA-GABA Conjugate (BL-1023* and AN-490) on MPTP-Induced Parkinson's Disease Model in Mice The protective effect of L-DOPA-GABA conjugates BL-1023* and AN-490 was tested using the 1-Methyl-4-phenyl-1,2,3,6-tetrahydropyridine (MPTP) mice model.

Materials and Methods:

Male C57/bl mice were obtained from Harlan, Israel and were housed in controlled conditions for one week prior to the experiments. All animal experiments were conducted according to the NIH Laboratory Animal Care Guidelines and with the approval of the Tel Aviv University Committee for Animal Experimentation (permit M-08-073).

Mice Model of MPTP Induced Parkinson:

Acute model: On day 1, C57/BL mice received 4× subcutaneous injections of 20 mg/kg MPTP-HCl (Sigma), dissolved in saline solution, at 2 hours intervals.

Subacute model: Once a day, for five consecutive days, the animals received a subcutaneous injection of 20 mg/kg MPTP-HCl.

Tests Used to Monitor the Treatment Effects:

Motor behavior: The effect of the treatment on motor behavior was assessed in the RotoRod and open-field tests, as follows.

RotoRod Test: The test measures and records motor coordination of rats and mice using the natural fear of falling motivation. RotoRod (San Diego Industries, San Diego, Calif., USA) was set on 16 rpm speed and accelerated to maximum speed of 25 rpm. The time until the mouse fall was measured up to maximum 4 minutes. The measurements were performed three times for each mouse and the average was calculated. Four animals were placed on the rod on individual lanes in the RotoRod enclosure. Photo beams were embedded in each of the four lanes of the enclosure. When the animal falls from the rotating rod, the photo beams were broken and the Rota-Rod recorded the animal's latency to fall. When the photo beams in all four lanes have been broken, the rod stopped rotating.

The Open Field Test:

The open field test measures behavioral responses, locomotor activity, hyperactivity, and exploratory behaviors. Open field test is also used as a measure of anxiety. Mice tend to avoid brightly illuminated, novel, open spaces, so the open field environment acts as an anxiogenic stimulus and allows for measurement of anxiety-induced locomotor activity and exploratory behaviors. The apparatus for the open field test is a square (0.5×0.5 meter) made of white melamine. All activities were recorded by a video camera mounted above the open field and scored in real-time by a motion-recognition software package (Noldus, Holland) that detects and analyzes the movements of the animals. The video image of the open field arena was partitioned into equal-size squares zone. Total distance, average speed, rearing/elongation behavior, and time spent in various parts of the field (e.g. the border areas vs. mid-area) were measured. Testing was carried out in a temperature, noise and light controlled room.

Tyrosine Hydroxylase Immunohistochemistry:

Animals under deep anesthesia were perfused through the aorta with phosphate-buffered saline (PBS), followed by a cold fixative consisting of 4% paraformaldehyde, 0.35% glutaraldehyde and 0.2% picric acid in phosphate buffer. After perfusion, the brain were removed and fixed in 4% paraformaldehyde for 24 hours, washed with PBS, dehydrated in increasing alcohol concentrations and embedded in paraffin. Paraffin-embedded tissues were processed as described [Rephaeli et al. Int J Cancer. 2005 Aug. 20; 116:226-35]. The avidin-biotin nonspecific binding was prevented by a blocking kit according to the manufacturer's protocol (Vector, USA). The sections were further incubated at 4° C. overnight with the primary antibody mouse monoclonal tyrosine hydroxylase (Visionbiosystem, Newcastle, UK, diluted 1:50). The secondary antibody was biotin conjugated goat anti-mouse IgG (Santa Cruz). Slides were then stained with ABC peroxidase system, developed with diaminobenzidine (DAB), chromogene substrate (Vector Laboratories, Inc. The slides were examined using an Olympus BX52 light microscope and images were taken with Olympus DP50 digital camera system. Images were analyzed by the ImagePro Plus 5.1 software. At least 12 different fields in each experimental group were analyzed. The Mean density±SEM was calculated for the striatum and the mean cell number±SEM was calculated for the SN.

Measurement of Dopamine and Catecholamines Content in the Brain:

The mice were killed by decapitation. Brains were rapidly removed and immediately frozen in liquid nitrogen, and stored at −80° C. until analyzed. For the assay, the thawed brain was homogenized on ice in 2 ml of 0.2 M perchloric acid. After centrifugation (10 000×g for 15 minutes at 4° C.), the supernatant was filtered and centrifuged through polypropylene Spin-X® centrifuge tube filter 0.22 µm nylon (Costar, Corning, N.Y., USA). Determination of the level of catecholamines under good laboratory practice was performed in the chemical laboratory of Rabin medical center. An aliquot of filtrate was injected into the HPLC system (Waters, Milford, Mass., USA) equipped with a C18 reverse phase, 3-µ LUNA column (100 mm×2 mm, Phenomenex, Torrance, Calif., USA). High-performance liquid chromatography (HPLC) with electrochemical detection was used to measure dopamine. Results were validated by co-elution with CA standards under various buffer conditions and detector settings. Results were validated using catecholamines (dopamine, L-DOPA, norepinephrine) standards. The samples of the Naïve and MPTP control groups were pooled from Experiments 1 and 3, as described hereinbelow.

Experiment 1: Protective Effect of AN-490 HCl Salt (Compound 21) in MPTP Acute Model Mice: 60 Males C57/BL/6J mice, 11 weeks old, weighing 22-25.5 grams.

All compounds were dissolved in saline. The concentration of the AN-490 compound was not corrected for purity.

MPTP administration: 4 IP injections of MPTP (Sigma)×20 mg/kg every 2 hours on day 0.

AN-490, as an HCl salt (shown below), was synthesized as described in Example 1 hereinabove and stored in desiccator in the cold room, and was brought to room temperature prior to weighing and dissolving it in saline. The volume of administration was 10 ml/kg.

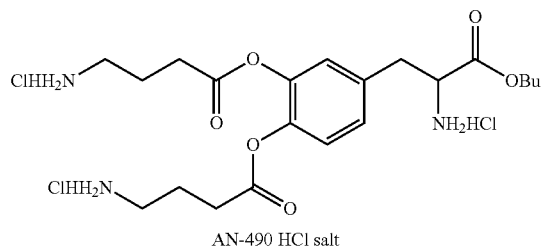

AN-490 HCl salt

Treatment groups (6 mice per group):
- Group 1—Control, saline treated mice
- Group 2—L-DOPA 25 mg/kg (per os)
- Group 3—AN-490 67.5 mg/kg (equimolar dose to 25 mg/kg L-DOPA)
- Group 4—MPTP only
- Group 5—MPTP+L-DOPA
- Group 6—MPTP+AN-490 67.5 mg/kg Treatment schedule: Days: 0, 1, 2, 3, 6, 7, 13, 16 by oral gavage.

Open field: was performed on days: 3, 6, 8, 16 (performed 90 minutes after treatment). Distance moved, velocity, immobility, strong mobility were measured.

Rota-Rod: was performed on days: 1, 3, 6 (performed 180 minutes after treatment)

Catecholamines biochemistry: Brains for dopamine were taken on day 20 and kept frozen in −70° C.

Experiment 2: Protective Effect of AN-490 HCl Salt (Compound 21) in MPTP Sub-Acute Model Mice: 60 C57/BL/6J mice (Harlan, Israel), 9-12 weeks old weighing 22-25.5 grams.

MPTP administration: Once a day, IP injection of 20 mg/kg for 5 consecutive days.

Treatment groups: 6 groups (10 mice per group):
- Group 1: Control, vehicle treated mice
- Group 2: MPTP+saline per os
- Group 3: MPTP+GABA.HCl 18.4 mg/kg (equimolar dose to 30 mg/kg L-DOPA) per os
- Group 4: MPTP+L-DOPA 30 mg/kg per os
- Group 5: MPTP+L-DOPA 30 mg/kg+GABA 18.4 mg/kg per os
- Group 6: MPTP+AN-490 81 mg/kg per os Treatment schedule: Starting from day 13, every day for 6 days and in the second week, due to observational signs of toxicity, the treatment was reduced to three times a week.

Behavioral studies: Open field test was performed 90 minutes prior to treatment, on days 11, 20 and 27 (during treatment) and Rota-Rod test was performed on day 24.

Immunohystochemistry (IHC): At termination, on days 29-30 of the treatment, the mice were perfused and the brains were taken for IHC staining for tyrosine hydroxylase.

Experiment 3: Protective Effect of BL-1023* (Compound 16) in MPTP Acute Model

BL-1023*, as an HCl salt (shown below) was prepared as described in Example 1 hereinabove. MW: 318.75 grams/mol. Appearance: brown powder. Purity: 90.12%. The concentration of the BL-1023* compound was not corrected for purity.

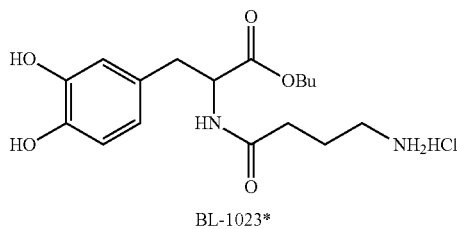

BL-1023*

Mice: 60 C57/BL/6J (Harlan, Israel) 9 weeks old weighing 22-25.5 grams.

MPTP administration: 4 imp injections of MPTP×20 mg/kg every 2 hours on day 1.

Treatment groups: 6 groups (10 mice per group):
  Group 1: Control, saline treated mice
  Group 2: MPTP+saline per os
  Group 3: MPTP+L-DOPA (30 mg/kg L-DOPA) per os
  Group 4: MPTP+GABA 18.4 mg/kg (equimolar)+L-DOPA (30 mg/kg per os)
  Group 5: MPTP+BL-1023* 48.4 mg/kg (equimolar to 30 mg/kg L-DOPA) per os
  Group 6: MPTP+BL-1023* 24.2 mg/kg (equimolar to 15 mg/kg L-DOPA) per os Treatment schedule: Starting at day 7 and then after 9, 11 and 13 days (total of 4 treatments)

Behavioral studies: Open field—day 13.
  Rotarod—on day 6 prior to treatment
  Rotarod—on day 12 (after two treatments).

Immunohystochemistry and catecholamine concentrations:
  Samples for IHC (3 mice per group) and for determination of catecholamines (3 mice per group) were taken on days 14-15.

Results:

Experiment 1: AN490-Acute Model

Four parameters of mice behavior in the open field paradigm were followed: distance moved, velocity, immobility and strong mobility. The results are presented in FIGS. 2A-2H.

In mice that were not treated with MPTP, L-DOPA (25 mg/kg per os) induced a tendency toward increase in motility compared to naïve mice or mice treated with equimolar dose of AN-490. This was evident by increase in distance moved, velocity and strong mobility, and a decrease in the time spent immobile behavior (see, FIG. 2). MPTP and L-DOPA treatment lower the motility of the mice Compared to all other treated groups and control naïve mice. The immobility and strong mobility of MPTP+L-DOPA vs. MPTP+AN-490 was significant ($p<0.05$). Interestingly, it can be seen that MPTP as well as MPTP+L-DOPA treatments induced an initial increase (day 3-6) in motility. On day 8, decreased motility and recovery on day 16 were observed. In the MPTP+AN-490 group, a continuous increase in motor activity was noted during the period of the study. Since it is likely that the MPTP treatment collapsed the BBB, GABA released by AN-490 evidently reaches the brain and imparted its protective activity.

It is important to mention that the test was not full established since none of the tested parameters was significantly reduced in the MPTP group relatively to the naïve group.

Consistent with the open field observations, it was found that in the Rotarod all the MPTP groups showed a tendency towards shorter latency time (see, FIG. 3).

The data obtained for changes in body weight as a parameter of toxicity show that the lowest average body weight was of the mice treated with MPTP+L-DOPA (see, FIG. 4).

In the study described herein the mice received MPTP and at the same day and thereafter they also were given the other treatments. This schedule of treatment is not reported in the literature. In most studies after the administration of MPTP the mice allow to recover for a week or more. The simultaneous treatment could account for the toxicity observed with L-DOPA.

Experiment 2: AN490-MPTP Sub-Acute Model

In this study the effect of treatments with AN-490, L-DOPA, GABA and L-DOPA+GABA on mice treated subchronically with MPTP was evaluated. The results on the Rotarod performed on day 24 and the behavior parameters in the open field test performed on days 11, 20 and 27 of the study, show no differences among the treated groups and the placebo animals (see, FIG. 5). AN-490 treated mice showed reduced vitality signs (fur appearance; see, Table 5 and FIG. 7), which was presumably attributed to hydrolysis of the conjugate.

As shown in FIG. 8, the IHC staining of brain demonstrated the disappearance of TH positively staining in the substantia nigra and striatum in mice treated with MPTP and protection or restoration of the normal morphology by GABA, GABA and L-DOPA and AN-490.

TABLE 5

| | Observation Observed parameters | | | | | | | |
|---|---|---|---|---|---|---|---|---|
| | observer 1 | | observer 2 | | observer 3 | | observer 4 | |
| Group | Vitality | Fur | Vitality | Fur | Vitality | Fur | Vitality | Fur |
| Control | +++ | +++ | +++ | +++ | +++ | +++ | +++ | +++ |
| MPTP | ++ | +++ | ++ | +++ | +++ | +++ | ++ | +++ |
| MPTP + GABA | +++ | +++ | +++ | ++ | +++ | +++ | +++ | +++ |
| MPTP + L-DOPA | ++ | +++ | ++ | +++ | +++ | +++ | +++ | +++ |
| MPTP + GABA + Dopa | ++ | +++ | ++ | ++ | +++ | +++ | +++ | +++ |
| MPTP + AN-490 | +++ | + | +++ | + | +++ | ++ | +++ | ++ |

Split fur +
Shiny fur +++
slow motions +
normal motion +++

These data suggest that MPTP could interfere with the intactness of the BBB, thus allowing the penetration of GABA to the brain, where it exhibits a neuroprotective effect. These data further show that AN-490 also exhibits TH protective activity, which could possibly be due to the release of GABA.

Experiment 3: MPTP Acute Model with BL-1023*

Behavioral parameters: In this experiment a protective effect of BL1023* against the shorter latency in the rotarod test, induced by MPTP treatment, was observed. The results are presented in FIG. 9, and show that this latency was not attenuated by L-DOPA or by the combination of L-DOPA and GABA. The behavioral signal was found in the rotarod, but not in the open field (see, FIG. 10), supporting the view that the open field test is not sufficiently indicative of anti-Parkinson activity in this model.

The level of catecholamines: As shown in FIG. 12, the level of dopamine in the brains of all MPTP treated mice was significantly lower than the level in the brains of naïve mice, regardless of the treatment used. In all MPTP treated mice the level of L-DOPA was higher than in the naïve mice, suggesting that MPTP blocks the synthesis of catecholamines after TH.

The level of norepinephrine in the MPTP treated group was significantly lower than the naïve group. The level of norepinephrine in MPTP+L-DOPA or in MPTP+L-DOPA and GABA treated mice was similar to that of naïve mice, suggesting that treatment with L-DOPA results in a higher level of this catecholamine. Treatment with BL-1023* did not restore the norepinephrine levels.

Staining for TH in the striatum and the substantia nigra: Along with the protective effect of BL1023* in the rotarod, IHC staining for TH in the striatum, exhibited a marked neuroprotective effect, expressed by a significant higher TH levels in the BL-1023* treated animals as compared to MPTP or MPTP combined with L-DOPA or with L-DOPA and GABA (see, FIGS. 13-16). Overall it can be concluded that BL-1023* and GABA protect the TH positive cells.

Example 4

Specific Binding of BL-1023 (Compound 5) to Various Proteins and Receptors Using Radioligand Binding Assay The binding of BL-1023 to the following proteins/receptors was assessed: Adenosine $A_1$, Adenosine $A_{2A}$, Adenosine $A_3$, Adrenergic $\alpha_1$ Non-Selective, Adrenergic $\alpha_2$ Non-Selective, Adrenergic $\beta_1$, Adrenergic $\beta_2$, Angiotensin $AT_1$, Bradykinin $B_2$, Chemokine CCR1, Chemokine CXCR2 (IL-8$R_B$), Dopamine $D_1$, Dopamine $D_{2L}$, Dopamine $D_{2S}$, Dopamine $D_3$, Dopamine $D_{4.2}$, Dopamine $D_{4.4}$, Dopamine $D_{4.7}$, Dopamine $D_5$, Endothelin $ET_A$, Endothelin $ET_B$, $GABA_A$-Chloride Channel-TBOB, $GABA_A$, -Chloride Channel-TBPS, $GABA_A$-Muscimol-Central, $GABA_A$-Ro-15-1788-Cerebellum, $GABA_A$-Ro-15-1788-Hippocampus, $GABA_{B1A}$, $GABA_{B1B}$, Histamine H1, Histamine H2, Histamine H3, Muscarinic M1, Muscarinic M2, Muscrinic M3, Neuropeptide YY1, Neuropeptide YY2, Neurotensin NT1, Opiate δ (OP1, DOP), Opiate κ (OP2, KOP), Opiate μ (OP3, MOP), Serotonin 5-$HT_{1A}$, Serotonin 5-$HT_{1B}$, Serotonin 5-$HT_{2A}$, Serotonin 5-$HT_{2B}$, Serotonin 5-$HT_3$, Serotonin 5-$HT_{5A}$, Serotonin 5-$HT_6$, Serotonin 5-$HT_7$, Sigma $\sigma_1$, Sigma $\sigma_2$, Sodium channel, site 2, Somatostatin sst1, Somatostatin sst2, Somatostatin sst3, Somatostatin sst4, Somatostatin sst5, Tachykinin NK1, Tachykinin NK2, Dopamine Transporter (DAT), Norepinephrin Transporter (NET), Vasoactive Intestinal Peptide ($VIP_1$), and Vasopressin $V_{1A}$.

Radioligand Assay:

The binding of BL-1023 to the various proteins/receptors was determined using a radioligand assay. In the radioligand assay the binding affinity of BL-1023 to a specific receptor/protein target was determined by assessing the percent of inhibition of the binding of a well-known radiolabeled ligand to the specific protein/receptor target in the presence of BL-1023. Reference standards were run as an integral part of each assay to ensure the validity of the results obtained.

The IC50 values were determined by a non-linear, least squares regression analysis using MathIQ™ (ID Business Solutions Ltd., UK) and inhibition constants (Ki) were calculated using the equation of Cheng and Prusoff (Cheng, Y., Prusoff, W. H., *Biochem. Pharmacol.* 22:3099-3108, 1973) using the observed IC50 of the tested compound, the concentration of radioligand employed in the assay, and the historical values for the $K_D$ of the ligand.

The significance criteria were a>50% stimulation or inhibition of the radioligand binding to its target protein/receptor.

Results:

BL-1023, at concentrations up to 10 μM, was not found to significantly inhibit/stimulate the binding of any of the radioligands to the tested proteins/receptors. These results therefore suggest that the extent of binding of BL-1023 to the tested protein/receptors is relatively low.

Example 5

Therapeutic Potential of BL-1023 (Compound 5) After Development of MPTP Lesion: Up Scaled Study The study assess the potential of BL-1023 to correct locomotor deficits, restore DA levels in the striata, and induce TH sprouting of neurons after lesion development. For these studies mice are first intoxicated with acute doses of MPTP (4 injections of 18 mg/kg, IP) which induces strong microglial inflammatory responses with virtual complete loss of striatal TH termini and robust nigral neurodegeneration with approximates 70%. The study is developed into 2 parts:

Part 1. Mice are treated with BL-1023 and L-DOPA 24 hours prior to and 12 hours following MPTP intoxication. Daily administration continues until day 6, in order to allow for metabolism and excretion of the majority of the MPTP and MPP+. This staggered initiation precludes the possibility that excess dopamine either from BL-1023 or L-DOPA may inhibit MPP+ uptake by neuronal dopamine transporters. The intent is to give the drug before and at the time the lesion is developing to exert the therapeutic effect for that time. The purpose of giving the drug at 12 hours post MPTP is to initiate drug as soon as possible after MPTP without the drug interfering with the metabolism of MPTP to MPP+ and limiting inhibition of MPP+ uptake by DA neurons via competition with excess drug-derived dopamine in the brain. Computerized spreadsheets containing mouse ear tag number, date of birth, date of death or sacrifice, dose and treatment schedule, body weight and behavioral data are maintained. All animal procedures follow the guidelines established by the National Institutes of Health guidelines and be approved by the Institutional Animal Care and Use Committee of the University of Nebraska Medical Center.

Part 2. At day 6 post MPTP treatment, one set of mice are sacrificed and the extent of MPTP lesion and DA loss is assessed. Drug treatment (L-DOPA and BL-1023) is administered daily from day 7 and proceed until day 35 (28 days post-MPTP). During that time, mice are assessed for locomotor function by overall rotarod performance and grip strength. On days 14, 21, 28 and 35, striatal catecholamine levels and the extent of TH sprouting by any remaining dopaminergic neurons is assessed. In addition, mice are monitored for rotarod performance twice every week and are pre-conditioned for 3 days prior to testing. Mice are placed on a partitioned rotating rod (Rotamex Rota-rod apparatus, Columbus Instruments, Columbus, Ohio) and tested at a 5 10, and 15 rpm for a maximum of 90 seconds at each speed with a minimum of 5 minutes rest between attempts. The overall rotarod performance (ORP) is calculated as the area under the curve using Prism (version 4, Graphpad Software, San Diego, Calif.) from the plot of the time that the animal remained on the rod as a function of the rotation speed. Grip strength of hind limbs of mice is assessed each week. Each mouse is placed on the wire-lid of a conventional housing cage and gently shaken to prompt the mouse to hold on to the grid. The lid is turned upside down and the duration determined until the mouse released both hind limbs. Each mouse is given three attempts with a maximum duration of 90 seconds and the longest latency is recorded. All animals are assessed every 3 days for body weight and weekly for signs of motor deficit: 4 points if normal (no sign of motor dysfunction), 3 points if hind limb weakness is evident when suspended by the tail, 2 points if gait abnormalities are present, and 1 point for dragging of at least one hind limb.

Mice were divided to the following treatment groups (20-60 mice per group):
1 PBS Control
1 MPTP Control
3 40 mg/kg BL-1023 in the post-MPTP treatment schedule: administered 24 hours before MPTP intoxication and 12 hours post MPTP intoxication. Administration continues until day 6.
4 24.8 mg/kg L-DOPA in the post-MPTP treatment schedule: administered 24 hours before MPTP intoxication and 12 hours post MPTP intoxication. Administration continues until day 6.
5 40 mg/kg BL-1023 in the post-MPTP treatment schedule: administered 6 days post MPTP intoxication for 28 days.
6 24.8 mg/kg L-DOPA in the post-MPTP treatment schedule: administered 6 days post MPTP intoxication for 28 days.

Material and Methods:

Animals:

Male 6-7 week old, WT C57BU6J (stock 000664) are purchased from Jackson Laboratories (Bar Harbor, Me.). All animal procedures are performed in accordance with National Institutes of Health (NIH) guidelines and approved by the Institutional Animal Care and Use Committee (IACUC) of the University of Nebraska Medical Center (UNMC).

Drug Treatments:

Mice are administered daily IP doses of BL-1023 (40 mg/kg) or L-DOPA (24.8 mg/kg, the equivalent amount of L-DOPA contained in BL-1023) beginning one day before the MPTP intoxication (groups 3 and 4) and 7 days after MPTP intoxication (groups 5 and 6). Daily administration of the drug during the 6 days (groups 3 and 4) is to maintain drug during lesion development.

The effect of drug given during the 28 days after lesion development (groups 5 and 6) is also examined as well as the therapeutic efficacy of the drug after lesion development by testing recovery of locomotion during that time and dopaminergic termini sprouting at the end of that period (day 35 post MPTP).

MPTP Intoxication:

For acute intoxications, mice receive 4 subcutaneous injections, one injection every 2 hours, of either vehicle (PBS, 10 ml/kg) or MPTP-HCl/PBS (Sigma-Aldrich, St. Louis, Mo.) [18 mg/kg in 10 ml/kg, based on free base]. MPTP handling and safety measures are performed in accordance with published guidelines.

At appropriate time points following MPTP intoxication, mice are terminally anesthetized and transcardially perfused with 4% paraformaldehyde (PFA) in 0.1 M PBS using 0.9% saline as vascular rinse. The sacrificing is done on the same group of animals who undergo the behavioral tests. Brains are post-fixed in 4% PFA overnight, kept in 30% sucrose for 2 days, snap frozen, embedded in O.C.T compound, and 30 µm sections cut with a cryostat (CM1900, Leica, Bannockburn, Ill.). The sections are collected in PBS with sodium azide and processed free-floating for staining of striatal and nigral TH expression by dopaminergic neurons and MAC-1 expression by nigral microglia. Primary antibodies for immunohistochemistry include rabbit anti-TH antibody (1:2000; Calbiochem/EMD Biosciences, Inc., San Diego, Calif.) and rat anti-mouse CD11b or MAC-1 (1:1,000; Serotec, Raleigh, N.C.).

Immunostaining is visualized in the substantia nigra and striatum using diaminobenzidine (Sigma-Aldrich) as the chromogen and mounted on slides. Immunostained brain sections is then counterstained with thionin (Sigma-Aldrich). Fluoro-Jade C (Chemicon International, Inc., Temecula, Calif.) is used to stain degenerating neurons in substantia nigra after day 2 post MPTP and is detected as green fluorescence by fluorescence microscopy with FITC filter (Eclipse E800, Nikon, Inc., Melville, N.Y.). To assess reactive microglia, midbrain sections (30 µm) from 5-7 mice per treatment group (12 sections per animal), numbers of amoeboid MAC-1$^+$ cells per mm$^2$ is obtained within the SN and averaged for each animal.

Measurement of Striatal Catecholamines and TH-Positive Neurons and Termini:

Striatal dopamine and its metabolites, dihydroxyphenylacetic acid, and homovanillic acid (HVA), is analyzed 6, 14, 21, 28 and 35 days after MPTP intoxication by reverse-phase HPLC using electrochemical detection. Briefly, striata are harvested and sonicated in 50 volumes (w/v) 0.1 M perchloric acid/10$^{-7}$ M ascorbic acid containing 50 ng/ml dihydrobenzylamine as internal standard. After centrifugation at 15,000 g for 15 minutes at 4° C., 20 µl of supernatant is injected onto a C18-reverse-phase HR-80 catecholamine column (ESA, Bedford, Mass.) at 25° C. The mobile phase consists of 90% 50 mM sodium phosphate/0.2 mM EDTA/1.2 mM heptanesulfonic acid (pH 3.2) solution and 10% methanol and is pumped at 1.0 ml per minute. Peaks are detected at +750 mA using an electrochemical detector (BAS, West Lafayette, Ind.) with a glassy carbon working electrode and a Ag/AgCl reference electrode; peak area is compared to the internal standard peak area. Data are collected and processed using the EZ Start data analysis software (Shimadzu Scientific, Columbia, Md.). Catecholamine levels are quantitated by comparison of peak areas to those of known standards of various concentrations spiked into control matrix. Stock solutions of catecholamines are made in 100% methanol at a concentration of 1.0 mg/ml and stored for up to 3 months at −20° C. Catecholamines are weighed on a Fisher Scientific accu-124 analytical balance (verified with reference weights) and an appropriate amount of HPLC-grade methanol is added to the measured standard to achieve a concentration of 1.0 mg/ml. The minimum weighing is of 100 mg. Catecholamine standard curves are made up in 0.1 M perchloric acid/10$^{-7}$ M ascorbic acid containing 50 ng/ml dihydrobenzylamine. The highest standard contains 300 ng/ml dopamine, 100 ng/ml dihydroxyphenylacetic acid, and 75 ng/ml HVA, and serial dilutions are made to 75%, 40%, 20%, and 10% of the highest standard mix. A 0% standard is also included for a total of 6 standards. Linear regression analysis of standard concentration vs. peak area is performed to determine analyte concentration in the experimental samples. Triplicate injections of each standard and sample are used and the results from the triplicate injections are averaged. Calibration (standard) curves is run with each sample set to account for daily variation in the HPLC system. Calibration standards is run at the beginning of a sample set and interspersed with the samples to determine variation in the sampling method over the course of analysis of a sample set. System suitability is checked daily by 5 replicate injections of a control sample spiked with dopamine, dihydroxyphenylacetic acid and HVA. Variations in peak area and retention time of less than 2% (for biological samples) are considered acceptable.

Total numbers of Nissl- and TH-stained neurons throughout the entire Substantia Nigra are counted stereologically in a blinded fashion with Stereo Investigator software (MicroBrightfield, Williston, Vt.) using the Optical Fractionator probe module. Quantitation of striatal termini is determined by TH immunostaining and digital image analysis (Scion, Frederick, Md.).

Behavioral Analysis: The behavioral tests are performed with 12 mice per group every week. The rest of the groups are administered drugs and do not undergo behavioral tests. Mice are monitored for rotarod performance and pre-conditioned for 3 days prior to initiation of testing. In brief, mice are placed on a partitioned rotating rod (Rotamex Rota-rod apparatus, Columbus Instruments, Columbus, Ohio) and tested at a 5, 10, and 15 rpm for a maximum of 180 seconds at each speed with a minimum of 5 minutes rest between attempts. Overall rotarod performance (ORP) is calculated as the area under the curve using Prism (version 4, Graphpad Software, San Diego, Calif.) from the plot of the time that the animal remains on the rod and the function of the rotation speed. Learned motor skills in the rotarod beyond that of pre-conditioned skills are evident from significant increases in ORP and/or diminished variances within the PBS control group. Grip strength is assessed by the paw grip endurance (PaGE) test. For PaGE analysis each mouse is placed on the wire-lid of a conventional housing cage and gently shaken to prompt the mouse to hold on to the grid. The lid is turned upside down and the duration until the mouse release both hind limbs is determined. Each mouse is given three attempts with a maximum duration of 90 seconds and the longest latency recorded.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having the general formula I:

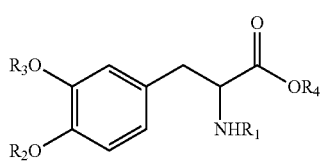

Formula I wherein:
$R_2$ and $R_3$ are each 4-amino-butyryl (GABA) and $R_1$ is selected from the group consisting of hydrogen and 4-amino-butyryl (GABA); and
$R_4$ is selected from the group consisting of hydrogen, alkyl, butyryloxyalkyl and 4-amino butyryloxyalkyl,
or a pharmaceutically acceptable acid addition salt thereof.

2. The compound of claim 1, wherein $R_1$ is hydrogen.
3. The compound of claim 2, wherein $R_4$ is alkyl.
4. The compound of claim 3, wherein said alkyl is butyl.
5. The compound of claim 4, being in a form of said a pharmaceutically acceptable acid addition salt.
6. The compound of claim 5, wherein said acid addition salt is a benzenesulfonic acid addition salt (besylate).
7. The compound of claim 1, wherein each of $R_1$-$R_3$ is 4-amino-butyryl (GABA).
8. The compound of claim 7, wherein $R_4$ is alkyl.
9. The compound of claim 8, wherein said alkyl is butyl.
10. The compound of claim 8, wherein said alkyl is methyl.
11. The compound of claim 1, wherein:
$R_1$ and $R_2$ are each 4-amino-butyryl (GABA);
$R_1$ is hydrogen; and
$R_4$ is butyl,
or a benzenesulfonic acid addition salt (besylate) thereof.
12. The compound of claim 1, wherein:
$R_1$, $R_2$ and $R_3$ are each 4-amino-butyryl (GABA); and
$R_4$ is butyl.
13. The compound of claim 1, wherein:
$R_1$, $R_2$ and $R_3$ are each 4-amino-butyryl (GABA); and
$R_4$ is methyl.
14. The compound of claim 1, wherein said acid addition salt is selected from the group consisting of hydrochloric acid addition salt, acetic acid addition salt, ascorbic acid addition salt, benzenesulfonic acid addition salt (besylate), naphthylsulfonic acid addition salt (napsylate), camphorsulfonic acid addition salt, citric acid addition salt, maleic acid addition salt, methanesulfonic acid addition salt (mesylate), oxalic acid addition salt, phosphoric acid addition salt, succinic acid addition salt, sulfuric acid addition salt and tartaric acid addition salt.
15. A pharmaceutical composition comprising, as an active ingredient, the compound of claim 1 and a pharmaceutically acceptable carrier.
16. An article-of-manufacturing comprising the pharmaceutical composition of claim 15, the composition being packaged in a packaging material and identified in print, on or in said packaging material, for use in the treatment of a neurodegenerative disease or disorder.
17. The article-of-manufacturing of claim 16, wherein said neurodegenerative disease or disorder is Parkinson's disease.
18. A method of treating a neurodegenerative disease or disorder, the method comprising administering to a subject in need thereof a therapeutically effective amount of the compound of claim 1, thereby treating the neurodegenerative disease or disorder disease.
19. The method of claim 18, wherein said neurodegenerative disease or disorder is Parkinson's disease.
20. A pharmaceutical composition comprising, as an active ingredient, the compound of claim 11 and a pharmaceutically acceptable carrier.
21. An article-of-manufacturing comprising the pharmaceutical composition of claim 20, the composition being packaged in a packaging material and identified in print, on or in said packaging material, for use in the treatment of a neurodegenerative disease or disorder.
22. The article-of-manufacturing of claim 21, wherein said neurodegenerative disease or disorder is Parkinson's disease.
23. A method of treating a neurodegenerative disease or disorder, the method comprising administering to a subject in need thereof a therapeutically effective amount of the compound of claim 11, thereby treating the neurodegenerative disease or disorder disease.
24. The method of claim 23, wherein said neurodegenerative disease or disorder is Parkinson's disease.
25. A pharmaceutical composition comprising, as an active ingredient, the compound of claim 12 and a pharmaceutically acceptable carrier.
26. An article-of-manufacturing comprising the pharmaceutical composition of claim 12, the composition being packaged in a packaging material and identified in print, on or in said packaging material, for use in the treatment of a neurodegenerative disease or disorder.

27. The article-of-manufacturing of claim 26, wherein said neurodegenerative disease or disorder is Parkinson's disease.

28. A method of treating a neurodegenerative disease or disorder, the method comprising administering to a subject in need thereof a therapeutically effective amount of the compound of claim 12, thereby treating the neurodegenerative disease or disorder disease.

29. The method of claim 28, wherein said neurodegenerative disease or disorder is Parkinson's disease.

30. A pharmaceutical composition comprising, as an active ingredient, the compound of claim 13 and a pharmaceutically acceptable carrier.

31. An article-of-manufacturing comprising the pharmaceutical composition of claim 30, the composition being packaged in a packaging material and identified in print, on or in said packaging material, for use in the treatment of a neurodegenerative disease or disorder.

32. The article-of-manufacturing of claim 31, wherein said neurodegenerative disease or disorder is Parkinson's disease.

33. A method of treating a neurodegenerative disease or disorder, the method comprising administering to a subject in need thereof a therapeutically effective amount of the compound of claim 13, thereby treating the neurodegenerative disease or disorder disease.

34. The method of claim 33, wherein said neurodegenerative disease or disorder is Parkinson's disease.

* * * * *